US011999932B2

(12) United States Patent
Hinojosa et al.

(10) Patent No.: US 11,999,932 B2
(45) Date of Patent: Jun. 4, 2024

(54) MICROFLUIDIC CONTROL

(71) Applicant: EMULATE, Inc., Boston, MA (US)

(72) Inventors: Christopher David Hinojosa, Malden, MA (US); Grace Ahn, Medford, MA (US)

(73) Assignee: EMULATE, INC., Boston, MA (US)

( * ) Notice: Subject to any disclaimer, the term of this patent is extended or adjusted under 35 U.S.C. 154(b) by 919 days.

(21) Appl. No.: 17/036,652

(22) Filed: Sep. 29, 2020

(65) Prior Publication Data

US 2021/0024866 A1 Jan. 28, 2021

Related U.S. Application Data

(63) Continuation of application No. PCT/US2019/025449, filed on Apr. 2, 2019.

(60) Provisional application No. 62/652,032, filed on Apr. 3, 2018.

(51) Int. Cl.
| | |
|---|---|
| *C12M 3/06* | (2006.01) |
| *C12M 1/00* | (2006.01) |
| *C12M 1/02* | (2006.01) |
| *C12M 1/12* | (2006.01) |

(52) U.S. Cl.
CPC ............ *C12M 23/16* (2013.01); *C12M 23/26* (2013.01); *C12M 25/02* (2013.01); *C12M 29/00* (2013.01); *C12M 41/18* (2013.01)

(58) Field of Classification Search
CPC ...... C12M 23/16; C12M 23/26; C12M 25/02; C12M 29/00; C12M 41/18
See application file for complete search history.

(56) References Cited

U.S. PATENT DOCUMENTS

| | | | | |
|---|---|---|---|---|
| 3,756,459 | A | * | 9/1973 | Bannister ............... G01N 35/08 604/141 |
| 7,303,727 | B1 | | 12/2007 | Dubrow et al. ............. 422/503 |
| 8,647,861 | B2 | | 2/2014 | Ingber et al. .............. 435/289.1 |
| 2004/0178879 | A1 | | 9/2004 | Mitra et al. .................... 338/34 |
| 2005/0042144 | A1 | | 2/2005 | Hubbard ...................... 422/400 |
| 2010/0041128 | A1 | * | 2/2010 | Banes ..................... C12M 23/16 435/297.1 |
| 2012/0107805 | A1 | | 5/2012 | Neas et al. ..................... 435/6.1 |
| 2015/0299641 | A1 | * | 10/2015 | Galliher .................. F16L 11/04 383/105 |
| 2016/0208207 | A1 | * | 7/2016 | Sugiura .................. C12M 23/38 |

(Continued)

FOREIGN PATENT DOCUMENTS

WO WO/2015/138034 9/2015

OTHER PUBLICATIONS

Breslauer, D. N. et al. (2006) "Microfluidics-based systems biology," *Molecular BioSystems* 2(2), 97-112.

(Continued)

*Primary Examiner* — Matthew D Krcha
*Assistant Examiner* — Tingchen Shi
(74) *Attorney, Agent, or Firm* — Medlen & Carroll, LLP

(57) ABSTRACT

The present invention is related to the field of fluidic devices, and in particular, microfluidic cell culture systems. The present invention provides pumping, recirculation and sampling for a microfluidic device or devices. The present invention provides solutions to the control of microfluidics for both terrestrial and space applications, including the control over the movement of fluids in zero gravity or microgravity.

50 Claims, 37 Drawing Sheets

(56) References Cited

U.S. PATENT DOCUMENTS

2017/0058243 A1  3/2017  Levner et al. ............... 422/502
2017/0349871 A1  12/2017  Ingber et al. ................. 435/29

OTHER PUBLICATIONS

Hamon, M. et al. (2013) "New tools and new biology: Recent miniaturized systems for molecular and cellular biology," *Molecules and Cells* 36(6), 485-506.

Park, J. W. et al. (2006) "Microfluidic culture platform for neuroscience research," *Nature Protocols* 1(4), 2128-2136.

Taylor, A. M. et al. (2006) "Microfluidic Chambers for Cell Migration and Neuroscience Research," in *Microfluidic Techniques: Reviews and Protocols* (Minteer, S. D., Ed.), pp. 167-177, Humana Press, Totowa, NJ.

PCT International Search Report of International Application No. PCT/US2019/025449 dated Jul. 26, 2019.

\* cited by examiner

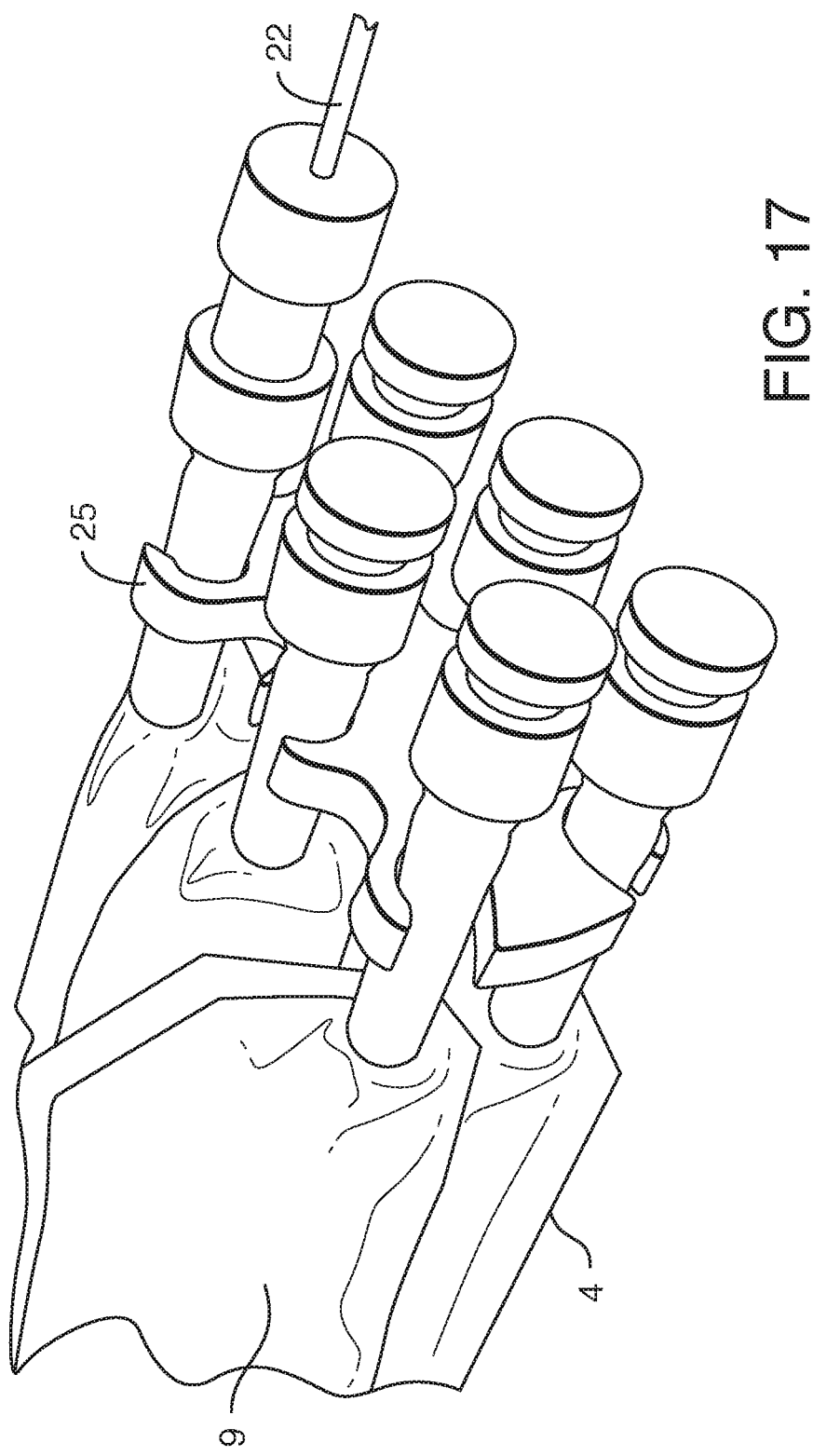

Figure 32

| Cylinder | | |
|---|---|---|
| T_inf, 1 (Liquid Inside Reservoir) | 4 | 277.15 |
| T_inf, 2 (Air Outside Reservoir) | 37 | 310.15 |
| | | |
| R_inf_H2O (Conv Inside) | | 1.175 |
| R_1 (Vessel Wall Thickness) | | 0.31 |
| R_2 (Vessel Insulation) | | 2.04 |
| R_inf_Air (Conv, low-g) | | 11.58 |
| | | |
| q_r (cylinder) | | 2.19 |

| Property | english | metric |
|---|---|---|
| t_1-2 (vessel) | 0.125 | 0.003175 |
| t_2-3 (insulation) | 0.125 | 0.003175 |
| | | |
| d_1 (ID vessel) | 2 | 0.0508 |
| d_2 (ID vessel + wall) | 2.25 | 0.05715 |
| d_3 (ID vessel + wall + insulation) | 2.5 | 0.0635 |
| | | |
| r_1 | 1 | 0.0254 |
| r_2 | 1.125 | 0.028575 |
| r_3 | 1.25 | 0.03175 |
| | | |
| L | 12 | 0.3048 |
| | | |
| k_1-2 @ ~4C (Acrylic) | | 0.2 |
| k_2-3 @ ~20C (Insulation) | | 0.027 |
| | | |
| h_inf_Air | | 1.48 |
| h_inf_H2O | | 15 |

| Cylinder Endcaps | | |
|---|---|---|
| T_inf, 1 | 4 | 277.15 |
| T_inf, 2 | 37 | 310.15 |
| | | |
| R_inf_H2O (Conv Inside) | | 27.85 |
| R_1 (Endcap Wall Thickness) | | 6.19 |
| R_2 (Endcap Insulation) | | 45.84 |
| R_inf_Air (Conv, low-g) | | 274.53 |
| | | |
| q_e (Both Endcap Walls) | | 0.20 |

| Property | english | metric |
|---|---|---|
| t_e (endcap thickness) | 0.125 | 0.003175 |
| | | |
| d_e (OD endcap) | 2.25 | 0.05715 |
| r_e (radius endcap) | 1.125 | 0.028575 |
| | | |
| k_1-2 @ ~4C (Acrylic) | | 0.2 |
| k_2-3 @ ~20C (Insulation) | | 0.027 |
| | | |
| h_inf_Air | | 1.48 |
| h_inf_H2O | | 15 |

| Tubing | | |
|---|---|---|
| T_inf, 1 | 0 | 273.15 |
| T_inf, 2 | 37 | 310.15 |
| | | |
| R_inf_H2O (Conv Inside) | | 3.29 |
| R_1 (Tube Wall) | | 0.613840 |
| R_2 (Insulation) | | 0.00 |
| R_inf_Air (Conv, low-g) | | 64.34 |
| | | |
| q_t (Single Cold Tubing Line) | | 0.54 |

| Property | english | metric |
|---|---|---|
| t_1-2 (vessel) | 0.1 | 0.00254 |
| t_2-3 (insulation) | 0 | 0 |
| | | |
| d_1 (ID Tube) | 0.25 | 0.00635 |
| d_2 (ID Tube + Wall) | 0.45 | 0.01143 |
| d_3 (ID Tube + Wall + Insulation) | 0.45 | 0.01143 |
| | | |
| r_1 | 0.125 | 0.003175 |
| r_2 | 0.225 | 0.005715 |
| r_3 | 0.225 | 0.005715 |
| | | |
| L | 12 | 0.3048 |
| | | |
| k_1-2 @ ~4C (Plastic) | | 0.5 |
| k_2-3 @ ~20C (Insulation) | | 0.027 |
| | | |
| h_inf_Air | | 1.48 |
| h_inf_H2O | | 50 |

MICROFLUIDIC CONTROL

FIELD OF THE INVENTION

The present invention is related to the field of fluidic devices, and in particular, microfluidic cell culture systems. The present invention provides pumping, recirculation and sampling for a microfluidic device or devices. The present invention provides solutions to the control of microfluidics for both terrestrial and space applications, including the control over the movement of fluids in zero gravity or microgravity.

BACKGROUND

Microfluidics provides a new technological platform, based on the flow of liquids in channels of micrometer size. Hamon et al., "New tools and new biology: recent miniaturized systems for molecular and cellular biology" Mol. Cells. 36:485-506 (2013); Park et al., "Microfluidic culture platform for neuroscience research" Nat. Protoc. 1:2128-2136 (2006); and Taylor et al., "Microfluidic chambers for cell migration and neuroscience research" Methods Mol. Biol. 321:167-177 (2005).

This new technology offers useful experimental tools for studying cells ex vivo. Compared with conventional culture systems, a microfluidic device can provide a physiologically more relevant cellular environment, by generating fluid flows which can maintain a more constant and soluble microenvironment. Breslauer et al., "Microfluidics-based systems biology" Mol. Biosyst. 2:97-112 (2006).

However, control over microfluidics is difficult, particularly if it is desired to explore questions beyond terrestrial conditions, such as those found in space. What is needed in the art is an improved microfluidics technology to provide such control.

SUMMARY OF THE INVENTION

The present invention is related to the field of fluidic devices, and in particular, microfluidic cell culture systems. The present invention provides pumping, recirculation and sampling for a microfluidic device or devices. The present invention provides solutions to the control of microfluidics for both terrestrial and space applications, including the control over the movement of fluids in zero gravity or microgravity.

In one embodiment, the present invention provides, an assembly, comprising a) one or more reservoirs contained within b) a container, said container comprising a working fluid (liquid or gas), said reservoirs i) in fluidic communication (e.g. via conduits) with c) one or more fluidic devices (including but not limited to microfluidic devices), ii) comprising a least one deformable portion (or being completely deformable), and ii) comprising liquid (e.g. media), wherein there is no mixing of said working fluid with said liquid (e.g. media). It is not intended that the present invention be limited by the nature or shape of the internal reservoir(s). In one embodiment, the internal reservoir(s) can take a form similar to a syringe, whether generally rigid overall or flexible, with a moveable plunger. For example, a syringe is a simple reciprocating pump consisting of a plunger or piston that fits tightly within a cylindrical tube called a barrel (which can be rigid, semi-rigid, or flexible). The plunger can be linearly pulled and pushed along the inside of the tube, allowing the syringe to take in and expel liquid or gas through a discharge orifice at the front (open) end of the tube (or other conduit). In one embodiment, the said one or more reservoirs are flexible. In one embodiment, said at least one deformable portion comprises a plunger. In one embodiment, said one or more reservoirs comprise plastic bags similar to IV bags, that can be compressed (e.g. with pressure from the working fluid) so that the fluid in the bag exits the bag through tubing (or other conduit). A variety of bag volumes is contemplated (e.g. between 1 ml and 1000 ml, more typically, between 5 ml and 100 ml, and more preferably between 10 ml and 20 ml). In one embodiment, 6 flexible bags of approximately 18 ml in volume fit inside a 2-inch diameter rigid container. Whether fluid exits the bag can be controlled further with a valve. Where there is more than one internal reservoir, each internal reservoir can comprise a valve to control fluid flow (e.g. in one position the valve blocks the fluid, while in another position the valve permits fluid flow). One or more pressure sensors can be added to the assembly so that clogging of a conduit can be detected and remedied.

It is not intended that the present invention be limited by the nature of the fluidic device. In one embodiment, the fluidic device comprises a microfluidic device. In one embodiment, the microfluidic device comprises one or more microfluidic channels. In one embodiment, the microfluidic device comprises inlet and outlet ports, said inlet and outlet ports in fluidic communication with said one or more microfluidic channels. In one embodiment, said microfluidic channels comprise cells. In one embodiment, said cells are on a membrane.

It is also not intended that the present invention be limited by the nature of the container or number of containers. In one embodiment, said container is rigid. In one embodiment, said container is flexible. In one embodiment, said container is collapsible (e.g. a lighter and collapsible container so as to take up a smaller volume during shipping). In one embodiment, there is a series of containers. In one embodiment a container maintains a preferred interior environment, such as with the use of insulation. In one embodiment a container comprises multiple vacuum insulated walls (e.g. 2, 3, 4, etc.) In one embodiment a container is insulated with a material such as foam, reflective material, etc. In one embodiment a container is insulated with a fluid layer, either a gas or liquid. In one embodiment, an insulated container is housed within another container. In one embodiment, an insulated container houses another container. In one embodiment, the rigid, insulated or uninsulated container, houses reservoirs. In a preferred embodiment, the container is rigid and the reservoir(s) within the container are flexible (a type of "bag in a box" design). In a preferred embodiment the rigid container comprises two vacuum insulated walls, separated by a space of vacuum, much like that of a commercial off-the-shelf (COTS) drink thermos. In a preferred embodiment, wherein said container is sealed such that said working fluid can only enter or exit the container through conduits. In one embodiment, the working fluid surrounds at least one internal reservoir. In one embodiment, the working fluid surrounds a plurality of internal reservoirs. In one embodiment, there is more than one container, each container containing working fluid surrounding at least one internal reservoir.

In one embodiment, the container is used to cool the working fluid. In one embodiment, the working fluid is used to cool. In yet another embodiment, the working fluid is cooled using a cooling conduit (surrounding the container, outside the container, internal to the container, or a combination of both) comprising a cooling fluid, wherein said cooling fluid does not mix with said working fluid or with said liquid of the internal reservoirs (e.g. with the media). It is not intended that the present invention be limited by the nature of the cooling conduit. In one embodiment, said cooling conduit comprises stainless steel tubing. In any event, cooling is useful to preserve the integrity of the liquid of the internal reservoirs (or at least components of the liquid). For example, where the liquid is culture media containing ingredients that degrade (e.g. Vitamin C), keeping the media cool allows for a longer shelf life. It also useful to work with degassed media.

In one embodiment, the container (or portion thereof) can be compressed so as to apply pressure on one or more internal reservoirs, causing liquid to be displaced and move out of said one or more internal reservoirs (e.g. via one or more conduits). In one embodiment, said container is in fluidic communication with a pump and a working fluid reservoir (e.g. via conduits). In a preferred embodiment, said pump and working fluid reservoir are positioned outside of said container. It is not intended that the present invention be limited by the nature of the pump. In one embodiment, the pump is selected from the group consisting of a volumetric pump, a pressure pump, a peristaltic pump and a syringe pump. In one embodiment, said pump is a displacement pump.

It is believed that the assembly discussed above can be used generally for fluidic devices. However, it has a particularly beneficial use where said fluidic devices comprise microfluidic devices. It is not necessary that the microfluidic devices be positioned within the container. In a preferred embodiment, said one or more microfluidic devices are outside said container, such as an embodiment, wherein said one or more microfluidic devices are housed in a manifold (e.g. along with one or more valves, such as diaphragm valves, and fluidic connectors, connecting to external fluid conduits, so that the microfluidic devices on the manifold are in fluidic communication with the reservoirs internal to the container, as well as in fluidic communication with any sampling conduits or recirculation pathways). In one embodiment, the manifold comprises pins to align or even to attach the microfluidic devices to the manifold. The manifold can comprise a plurality of microfluidic devices, each with their own associated valves and fluidic connections. In one embodiment, the manifold is configured to heat liquid prior to the liquid entering one or more microfluidic devices (one example of "just in time" heating). In one embodiment, said liquid is heated after it is displaced and while it begins flowing into said one or more fluidic devices (another example of "just in time" heating). In one embodiment, a long tube is used to heat a small volume. In one embodiment, a micromachined heater is used. In one embodiment, the manifold is temperature controlled. In one embodiment, the manifold is temperature controlled by enclosing the manifold in an incubator (allowing for the microfluidic devices to be exposed to temperatures consistent with cell growth and viability, such as 37° C.+/−2 degrees, as well as proper humidity and $CO_2$ levels). In one embodiment, the incubator or the manifold comprises a temperature sensor. In one embodiment, resistance to flow is introduced through tubing (e.g. capillary tubing) connecting the flexible reservoirs to the manifold. In one embodiment, resistance can be manipulated by changing the cross-sectional diameter of the capillary tubing. By applying resistance to flow, greater control over flow is achieved. More specifically, by providing resistance one can achieve equal flow rates across multiple chips. By increasing resistance, one can reduce flow rate variability across multiple microfluidic devices.

It is not intended that the present invention be limited by the precise design of the microfluidic devices, which can have microfluidic channels (e.g. channels wherein one or more dimensions are 1 mm or smaller, and more typically 0.1 mm or smaller) and (optionally) membranes (as well as inlet and outlet ports so that liquid can enter and exit the microfluidic channels). In one embodiment, said one or more microfluidic devices comprise living cells on a surface. In one embodiment, said surface is a microfluidic channel or portion thereof. In one embodiment, said surface is a membrane.

It is not intended that the present invention be limited by the nature of the liquid in the internal reservoirs. However, in a preferred embodiment, the liquid is a media for conveying one or more substances. In a particularly preferred embodiment, said media comprises cell culture media (preferably degassed media). Importantly, it is preferred that there is no contact between the working fluid and the culture fluid, i.e. they are separated, e.g. by the walls of the internal reservoirs.

It is not intended that the present invention be limited by the nature of the working fluid. In one embodiment, said working fluid comprises an oil. In one embodiment, said working fluid comprises a gas. It is also not intended that the present invention be limited by the number of working fluids. In one embodiment, said container comprises first and second working fluids. For example, in one embodiment, said first working fluid is a gas and said second working fluid is a liquid. One can introduce or remove a second working fluid from the container to change the pressure on the internal reservoirs. In one embodiment, one can pump gas into the container to impart pressure on the other working fluid.

In yet another embodiment, the present invention contemplates an assembly, comprising a) one or more (or a plurality of) flexible reservoirs contained within b) a container, said container i) in fluidic communication with c) a pump and d) a working fluid reservoir and ii) comprising a working fluid (liquid or gas), said flexible reservoirs i) in fluidic communication with e) one or more fluidic devices (including but not limited to microfluidic devices) and ii) comprising cell culture media, wherein there is no mixing of said working fluid with said cell culture media (preferably degassed media). Again, it is not intended that the present invention be limited to nature or type of container or nature or type of internal reservoirs. In one embodiment, said container is rigid. In one embodiment, said container is flexible. In one embodiment, said container is collapsible. In one embodiment, said container is insulated or placed within a second container that is insulated. In one embodiment, the insulation comprises foam. In one embodiment, the insulation comprises reflective material. In one embodiment, the insulation comprises vacuum sealing. In one embodiment, said insulation is achieved via spaces of vacuum pressure between container walls. In one embodiment, multiple the insulation comprises vacuum pressure between multiple container walls (2, 3, 4, etc.) In one embodiment, the insulation is achieved via double-walled vacuum insulation. In one embodiment, said container is sealed such that said working fluid can only enter or exit the container through conduits. In one embodiment, the working fluid surrounds at least one internal reservoir. In one embodiment, the working fluid surrounds a plurality of internal reservoirs. In one embodiment, there is more than one container, each container containing working fluid surrounding at least one internal reservoir. In one embodiment, said container is rigid and said flexible reservoirs can be compressed (e.g. with pressure via a working fluid) so that the fluid in the bag exits the bag through tubing (or other conduit). Whether fluid exits the bag can be controlled further with a valve. Where there is more than one internal reservoir, each internal reservoir can comprise a valve to control fluid flow (e.g. in one position the valve blocks the fluid, while in another position the valve permits fluid flow). One or more pressure sensors can be added to the assembly so that clogging of a conduit can be detected and remedied.

It is not intended that the present invention be limited to the positioning of the microfluidic devices. In a preferred embodiment, said one or more microfluidic devices are outside said container. In one embodiment, said one or more microfluidic devices are housed in a manifold (e.g. along with one or more valves, such as diaphragm valves, and fluidic connectors, connecting to external fluid conduits, so that the microfluidic devices on the manifold are in fluidic communication with the reservoirs internal to the container, as well as in fluidic communication with any sampling conduits or recirculation pathways). In one embodiment, the manifold comprises pins to align or even to attach the microfluidic devices to the manifold. The manifold can comprise a plurality of microfluidic devices, each with their own associated valves and fluidic connections. In one embodiment, the manifold is configured to heat liquid prior to the liquid entering one or more microfluidic devices (one example of "just in time" heating). In one embodiment, said liquid is heated after it is displaced and while it begins flowing into said one or more fluidic devices (another example of "just in time" heating). In one embodiment, the manifold is temperature controlled. In one embodiment, the manifold is temperature controlled by enclosing the manifold in an incubator (allowing for the microfluidic devices to be exposed to temperatures consistent with cell growth and viability, such as 37° C.+/−2 degrees, as well as proper humidity and $CO_2$ levels). In one embodiment, the incubator or the manifold comprises a temperature sensor. In one embodiment, resistance to flow is introduced through tubing (e.g. capillary tubing) connecting the flexible reservoirs to the manifold. In one embodiment, resistance can be manipulated by changing the cross-sectional diameter of the capillary tubing. By applying resistance to flow, greater control over flow is achieved. More specifically, by providing resistance one can achieve equal flow rates across multiple chips. By increasing resistance, one can reduce flow rate variability across multiple microfluidic devices.

It is not intended that the present invention be limited by the precise design of the fluidic or microfluidic devices. In one embodiment, the microfluidic devices have one or more microfluidic channels (e.g. channels wherein one or more dimensions are 1 mm or smaller, and more typically 0.1 mm or smaller) and (optionally) membranes (as well as inlet and outlet ports so that liquid can enter and exit the microfluidic channels). In one embodiment, said one or more microfluidic devices comprise living cells on a surface. In one embodiment, said surface is a microfluidic channel or portion thereof. In one embodiment, said surface is a membrane.

In one embodiment, the present invention contemplates valves to control the flow of said culture media (preferably degassed media) out of said flexible reservoirs. In one embodiment, valves control the flow of working fluid into or out of the container housing the reservoirs. In one embodiment, said pump and working fluid reservoir are outside of said container. In one embodiment, said pump is a displacement pump. In one embodiment, said pump is selected from the group consisting of a volumetric pump, a pressure pump, a peristaltic pump and a syringe pump. In one embodiment, each microfluidic device is in fluidic communication with a sampling conduit and a waste reservoir. In one embodiment, there is no contact between the working fluid and the culture fluid.

In one embodiment, said working fluid comprises an oil. In one embodiment, said working fluid comprises a gas. In one embodiment, said container comprises first and second working fluids. In one embodiment, said first working fluid is a gas and said second working fluid is a liquid. It is also not intended that the present invention be limited by the number of working fluids. One can introduce or remove a second working fluid from the container to change the pressure on the internal reservoirs. In one embodiment, one can pump gas into the container to impart pressure on the other working fluid.

In one embodiment, the container is used to cool the working fluid. In one embodiment, the working fluid is used to cool (e.g. the internal reservoirs). In yet another embodiment, the working fluid is cooled using a cooling conduit (surrounding the container, outside the container, internal to the container, or a combination of both) comprising a cooling fluid, wherein said cooling fluid does not mix with said working fluid or with said liquid of the internal reservoirs (e.g. with the media). It is not intended that the present invention be limited by the nature of the cooling conduit. In one embodiment, said cooling conduit comprises stainless steel tubing. In any event, cooling is useful to preserve the integrity of the liquid of the internal reservoirs (or at least components of the liquid). For example, where the liquid is culture media containing ingredients that degrade (e.g. Vitamin C), keeping the media cool allows for a longer shelf life. It also useful to work with degassed media.

In yet another embodiment, the present invention contemplates an assembly where there are two or more internal reservoirs in a single container, but where different liquid is in at least one reservoir (i.e. different from at least one other reservoir). For example, in one embodiment, the present invention contemplates an assembly, comprising a) one or more flexible cell culture media reservoirs and b) one or more flexible reagent reservoirs contained within c) a container, said container i) in fluidic communication with d) a pump and e) a working fluid reservoir and ii) comprising a working fluid, said flexible cell culture reservoirs i) in fluidic communication with d) one or more fluidic devices (including but not limited to) microfluidic devices and ii) comprising cell culture media (preferably degassed media), said one or more flexible reagent reservoirs i) in fluidic communication with said one or more fluidic devices (including but not limited to microfluidic devices) and ii) comprising reagent, wherein there is no mixing of said working fluid with said cell culture media. Again, it is not intended that the present invention be limited by the type or nature of the container(s) or reservoir(s). In one embodiment, said container is rigid. In one embodiment, said container is flexible. In one embodiment, said container is collapsible. In one embodiment, said container is insulated or placed within a second container that is insulated. In one embodiment, the insulation comprises foam. In one embodiment, the insulation comprises reflective material. In one embodiment, the insulation comprises vacuum sealing. In one embodiment, said insulation is achieved via spaces of vacuum pressure between container walls. In one embodiment, multiple the insulation comprises vacuum pressure between multiple container walls (2, 3, 4, etc.) In one embodiment, the insulation is achieved via double-walled vacuum insulation. In one embodiment, said container is sealed such that said working fluid can only enter or exit the container through conduits. In one embodiment, the working fluid surrounds at least one internal reservoir. In one embodiment, the working fluid surrounds a plurality of internal reservoirs. In one embodiment, there is more than one container, each container containing working fluid surrounding at least one internal reservoir. In one embodiment, said one or more fluidic devices are outside said container. In one embodiment, said one or more fluidic devices are microfluidic devices housed in a manifold. In one embodiment, the manifold is configured to heat liquid prior to the liquid entering one or more microfluidic devices (one example of "just in time" heating). In one embodiment, said liquid is heated after it is displaced and while it begins flowing into said one or more fluidic devices (another example of "just in time" heating). In one embodiment, the manifold is temperature controlled. In one embodiment, the manifold is temperature controlled by enclosing the manifold in an incubator (allowing for the microfluidic devices to be exposed to temperatures consistent with cell growth and viability, such as 37° C.+/−2 degrees, as well as proper humidity and $CO_2$ levels). In one embodiment, the incubator or the manifold comprises a temperature sensor. In one embodiment, resistance to flow is introduced through tubing (e.g. capillary tubing) connecting the flexible reservoirs to the manifold. In one embodiment, resistance can be manipulated by changing the cross-sectional diameter of the capillary tubing. By applying resistance to flow, greater control over flow is achieved. More specifically, by providing resistance one can achieve equal flow rates across multiple chips. By increasing resistance, one can reduce flow rate variability across multiple microfluidic devices. In one embodiment, said one or more microfluidic devices comprise living cells on a surface. In one embodiment, said surface is a microfluidic channel (e.g. channel wherein one or more dimensions are 1 mm or smaller, and more typically 0.1 mm or smaller) or portion thereof. In one embodiment, said surface is a membrane. In one embodiment, the microfluidic device comprises inlet and outlet ports, said inlet and outlet ports in fluidic communication with said one or more microfluidic channels. In one embodiment, said microfluidic channels comprise cells. In one embodiment, said cells are on a membrane. In one embodiment, the assembly further comprises valves to control the flow of said culture media out of said flexible reservoirs. In one embodiment, said pump and working fluid reservoir are outside of said container. In one embodiment, said pump is a displacement pump. In one embodiment, said pump is selected from the group consisting of a volumetric pump, a pressure pump, a peristaltic pump and a syringe pump. In one embodiment, each microfluidic device is in fluidic communication with a sampling conduit and a waste reservoir. In one embodiment, there is no contact between the working fluid and the culture fluid. In one embodiment, said working fluid comprises an oil. In one embodiment, said working fluid comprises a gas. In one embodiment, said container comprises first and second working fluids. In one embodiment, said first working fluid is a gas and said second working fluid is a liquid. In one embodiment, the assembly further comprises a cooling conduit (surrounding the container, outside the container, internal to the container, or a combination of both) comprising a cooling fluid, wherein said cooling fluid does not mix with said working fluid or with said media. In one embodiment, the container is used to cool the working fluid. In one embodiment, the working fluid is used to cool. In one embodiment, said cooling conduit comprises stainless steel tubing. It is not intended that the present invention be limited by the nature of the reagent in the reagent reservoir. In one embodiment, said reagent is selected from the group consisting of a lysate reagent, a fixative reagent and a staining reagent. In one embodiment, the assembly further comprises a flow rate sensor configured to detect the flow rate of culture fluid. In one embodiment, the assembly further comprises a pressure sensor configured to detect clogging and or blocking of flow of the culture fluid.

The present invention also contemplates methods, including (but not limited to) methods of movement of fluids in zero gravity or microgravity. In one embodiment, the present invention contemplates a method of moving liquid, comprising: 1) providing an assembly, comprising a) one or more reservoirs contained within b) a container, said container i) in fluidic communication with c) a pump and d) a working fluid reservoir and ii) comprising a working fluid (liquid or gas), said reservoirs i) in fluidic communication with e) one or more fluidic devices (including but not limited to one or more microfluidic devices), and ii) comprising liquid, wherein there is no mixing of said working fluid with said liquid; and 2) pumping said working fluid into said container with said pump under conditions that said liquid in said one or more reservoirs is displaced and flows into said one or more fluidic devices, thereby moving said liquid. In one embodiment, said liquid is moved in zero gravity or microgravity. In one embodiment, said working fluid is pumped into said container at a flow rate and the displaced liquid flows into said one or more fluidic devices at a flow rate. In one embodiment, the flow rate of the working fluid is the same as the flow rate of the liquid. In one embodiment, the flow rate of the working fluid is the not the same as the flow rate of the liquid. In one embodiment, resistance to flow is introduced through tubing (e.g. capillary tubing) connecting the flexible reservoirs to the one or more fluidic devices (or a manifold containing the one or more fluidic devices). In one embodiment, resistance can be manipulated by changing the cross-sectional diameter of the capillary tubing. By applying resistance to flow, greater control over flow is achieved. More specifically, by providing resistance one can achieve equal flow rates across multiple chips. By increasing resistance, one can reduce flow rate variability across multiple microfluidic devices. In one embodiment, wherein said assembly comprises valves to control the flow out of the reservoirs (e.g. the method can comprise controlling the valves, such as by opening or closing valves so as to permit or block flow, respectively).

Again, a variety of container types are contemplated. In one embodiment, said container is rigid. In one embodiment, said container is flexible. In one embodiment, said container is collapsible. In one embodiment, said container is insulated or placed within a second container that is insulated. In one embodiment, the insulation comprises foam. In one embodiment, the insulation comprises reflective material. In one embodiment, the insulation comprises vacuum sealing. In one embodiment, said insulation is achieved via spaces of vacuum pressure between container walls. In one embodiment, multiple the insulation comprises vacuum pressure between multiple container walls (2, 3, 4, etc.) In one embodiment, the insulation is achieved via double-walled vacuum insulation. In one embodiment, said container is sealed such that said working fluid can only enter or exit the container through conduits. In one embodiment, the working fluid surrounds at least one internal reservoir. In one embodiment, the working fluid surrounds a plurality of internal reservoirs. In one embodiment, there is more than one container, each container containing working fluid surrounding at least one internal reservoir. Again, a variety of reservoir types are contemplated. In one embodiment, said one or more reservoirs are flexible. In one embodiment, said one or more reservoirs are flexible and said container is rigid. In one embodiment, said one or more reservoirs comprise at least one deformable portion. In one embodiment, the method further comprises cooling said working fluid. In one embodiment, said working fluid is cooled with a cooling conduit (surrounding the container, outside the container, internal to the container, or a combination of both) comprising a cooling fluid, wherein said cooling fluid does not mix with said working fluid or with said liquid. In one embodiment, said cooling conduit comprises stainless steel tubing. In one embodiment, said liquid is heated after it is displaced but prior to it flowing into said one or more fluidic devices (one example of "just in time" heating). In one embodiment, said liquid is heated after it is displaced and while it begins flowing into said one or more fluidic devices (another example of "just in time" heating).

It is not intended that the present invention be limited by the nature of the fluidic device. In one embodiment, the fluidic device comprises a microfluidic device. In one embodiment, the microfluidic device comprises one or more microfluidic channels. In one embodiment, the microfluidic device comprises inlet and outlet ports, said inlet and outlet ports in fluidic communication with said one or more microfluidic channels. In one embodiment, said microfluidic channels comprise cells. In one embodiment, said cells are on a membrane.

In yet another embodiment, the present invention contemplates a method of moving liquid, comprising: 1) providing an assembly, comprising a) one or more reservoirs contained within b) a container, said container i) in fluidic communication with c) a working fluid reservoir and ii) comprising a working fluid (liquid or gas), said reservoirs i) in fluidic communication with d) one or more fluidic devices (including but not limited to microfluidic devices), and ii) comprising liquid, wherein there is no mixing of said working fluid with said liquid; and 2) applying a force to said container under conditions that said liquid in said one or more reservoirs is displaced and flows into said one or more fluidic devices, thereby moving said liquid. In one embodiment, said liquid is moved in zero gravity or microgravity. In one embodiment, at least a portion of said container is deformable. In one embodiment, said container is flexible. In one embodiment, said container is collapsible. In one embodiment, said container is insulated or placed within a second container that is insulated. In one embodiment, the insulation comprises foam. In one embodiment, the insulation comprises reflective material. In one embodiment, the insulation comprises vacuum sealing. In one embodiment, said insulation is achieved via spaces of vacuum pressure between container walls. In one embodiment, multiple the insulation comprises vacuum pressure between multiple container walls (2, 3, 4, etc.) In one embodiment, the insulation is achieved via double-walled vacuum insulation. In one embodiment, said container is sealed such that said working fluid can only enter or exit the container through conduits. In one embodiment, the working fluid surrounds at least one internal reservoir. In one embodiment, the working fluid surrounds a plurality of reservoirs. In one embodiment, there is more than one container, each container containing working fluid surrounding at least one internal reservoir. In one embodiment, said one or more reservoirs are flexible. In one embodiment, said one or more reservoirs comprise at least one deformable portion. In one embodiment, applying a force comprises compressing at least a portion of said container. In one embodiment, the method further comprises cooling said working fluid. In one embodiment, said working fluid is cooled with a cooling conduit (surrounding the container, outside the container, internal to the container, or a combination of both) comprising a cooling fluid, wherein said cooling fluid does not mix with said working fluid or with said liquid. In one embodiment, said cooling conduit comprises stainless steel tubing. In one embodiment, the method comprises heating said liquid after it is displaced but prior to it flowing into said one or more fluidic devices. In one embodiment, said assembly comprises valves to control the flow out of the reservoirs (e.g. the method can comprise controlling the valves, such as by opening or closing valves so as to permit or block flow, respectively).

It is not intended that the present invention be limited by the nature of the fluidic device. In one embodiment, the fluidic device comprises a microfluidic device. In one embodiment, the microfluidic device comprises one or more microfluidic channels. In one embodiment, the microfluidic device comprises inlet and outlet ports, said inlet and outlet ports in fluidic communication with said one or more microfluidic channels. In one embodiment, said microfluidic channels comprise cells. In one embodiment, said cells are on a membrane.

In still another embodiment, the present invention contemplates a method of moving liquid, comprising: 1) providing an assembly, comprising a) one or more liquid reservoirs contained within b) a container, said container i) in fluidic communication with c) a first working fluid reservoir and d) a second working fluid reservoir, said first working fluid reservoir comprising a first working fluid, said second working fluid reservoir comprising a second working fluid, said container further comprising a portion of said second working fluid, said one or more liquid reservoirs i) in fluidic communication with e) one or more fluidic devices (including but not limited to one or more microfluidic devices), and ii) comprising liquid, wherein there is no mixing of said working fluid with said liquid; and 2) introducing said first working fluid from said first working fluid reservoir into said container under conditions that said pressure is imparted on said second working fluid such that liquid in said one or more reservoirs is displaced and flows into said one or more fluidic devices, thereby moving said liquid. In one embodiment, said liquid is moved in zero gravity or microgravity. In one embodiment, said first working fluid is pumped into said container at a flow rate and the displaced liquid flows into said one or more fluidic devices at a flow rate. In one embodiment, the flow rate of the working fluid is the same as the flow rate of the liquid. In one embodiment, the flow rate of the working fluid is the not the same as the flow rate of the liquid. In one embodiment, resistance to flow is introduced through tubing (e.g. capillary tubing) connecting the flexible reservoirs to the one or more fluidic devices (or a manifold containing the one or more fluidic devices). In one embodiment, resistance can be manipulated by changing the cross-sectional diameter of the capillary tubing. By applying resistance to flow, greater control over flow is achieved. More specifically, by providing resistance one can achieve equal flow rates across multiple chips. By increasing resistance, one can reduce flow rate variability across multiple microfluidic devices. In one embodiment, said assembly comprises valves to control the flow out of the reservoirs (e.g. the method can comprise controlling the valves, such as by opening or closing valves so as to permit or block flow, respectively).

Again, a variety of container types is contemplated. In one embodiment, said container is rigid. In one embodiment, said container is flexible. In one embodiment, said container is collapsible. In one embodiment, said container is insulated or placed within a second container that is insulated. In one embodiment, the insulation comprises foam. In one embodiment, the insulation comprises reflective material. In one embodiment, the insulation comprises vacuum sealing. In one embodiment, said insulation is achieved via spaces of vacuum pressure between container walls. In one embodiment, multiple the insulation comprises vacuum pressure between multiple container walls (2, 3, 4, etc.) In one embodiment, the insulation is achieved via double-walled vacuum insulation. In one embodiment, said container is sealed such that said working fluid can only enter or exit the container through conduits. In one embodiment, the working fluid surrounds at least one internal reservoir. In one embodiment, the working fluid surrounds a plurality of internal reservoirs. In one embodiment, there is more than one container, each container containing working fluid surrounding at least one internal reservoir. Again, a variety of reservoir types is contemplated. In one embodiment, said one or more reservoirs are flexible. In one embodiment, said one or more reservoirs comprise at least one deformable portion. In one embodiment, said first working fluid comprises a liquid. In one embodiment, said first working fluid comprises a gas. In one embodiment, the method further comprises cooling said first or second working fluid, or both. In one embodiment, said working fluid is cooled with a cooling conduit (surrounding the container, outside the container, internal to the container, or a combination of both) comprising a cooling fluid, wherein said cooling fluid does not mix with said working fluid(s) or with said liquid. In one embodiment, said cooling conduit comprises stainless steel tubing. In one embodiment, said liquid is heated after it is displaced but prior to it flowing into said one or more fluidic devices (one example of "just in time" heating). In one embodiment, said liquid is heated after it is displaced and while it begins flowing into said one or more fluidic devices (another example of "just in time" heating).

It is not intended that the present invention be limited by the nature of the fluidic device. In one embodiment, the fluidic device comprises a microfluidic device. In one embodiment, the microfluidic device comprises one or more microfluidic channels. In one embodiment, the microfluidic device comprises inlet and outlet ports, said inlet and outlet ports in fluidic communication with said one or more microfluidic channels. In one embodiment, said microfluidic channels comprise cells. In one embodiment, said cells are on a membrane.

In still another embodiment, the present invention contemplates a method of perfusing cells in microfluidic devices, comprising: 1) providing an assembly, comprising a) one or more flexible reservoirs contained within b) a container, said container i) in fluidic communication with c) a pump and d) a working fluid reservoir and ii) comprising a working fluid (liquid or gas), said flexible reservoirs i) in fluidic communication with e) one or more microfluidic devices comprising cells on a surface, and ii) comprising cell culture media (preferably degassed media), wherein there is no mixing of said working fluid with said cell culture media; and 2) pumping said working fluid into said container with said pump under conditions that the culture media in the flexible reservoirs is displaced and flows into said one or more microfluidic devices, thereby perfusing said cells. In one embodiment, said cells are perfused in zero gravity or microgravity. In one embodiment, said surface is a microfluidic channel or portion thereof. In one embodiment, said surface is a membrane. In one embodiment, said working fluid is pumped into said container at a flow rate and the displaced liquid flows into said one or more fluidic devices at a flow rate. In one embodiment, the flow rate of the working fluid is the same as the flow rate of the liquid. In one embodiment, the flow rate of the working fluid is the not the same as the flow rate of the liquid. In one embodiment, resistance to flow is introduced through tubing (e.g. capillary tubing) connecting the flexible reservoirs to the one or more fluidic devices (or a manifold containing the one or more fluidic devices). In one embodiment, resistance can be manipulated by changing the cross-sectional diameter of the capillary tubing. By applying resistance to flow, greater control over flow is achieved. More specifically, by providing resistance one can achieve equal flow rates across multiple chips. By increasing resistance, one can reduce flow rate variability across multiple microfluidic devices. In one embodiment, said assembly comprises valves to control the flow out of the reservoirs (e.g. the method can comprise controlling the valves, such as by opening or closing valves so as to permit or block flow, respectively).

Again, a variety of container types is contemplated. In one embodiment, said container is rigid. In one embodiment, said container is flexible. In one embodiment, said container is collapsible. In one embodiment, said container is insulated or placed within a second container that is insulated. In one embodiment, the insulation comprises foam. In one embodiment, the insulation comprises reflective material. In one embodiment, the insulation comprises vacuum sealing. In one embodiment, said insulation is achieved via spaces of vacuum pressure between container walls. In one embodiment, multiple the insulation comprises vacuum pressure between multiple container walls (2, 3, 4, etc.) In one embodiment, the insulation is achieved via double-walled vacuum insulation. In one embodiment, said container is sealed such that said working fluid can only enter or exit the container through conduits. In one embodiment, the working fluid surrounds at least one internal reservoir. In one embodiment, the working fluid surrounds a plurality of reservoirs. In one embodiment, there is more than one container, each container containing working fluid surrounding at least one internal reservoir. In one embodiment, said one or more microfluidic devices are outside said container. In one embodiment, said one or more microfluidic devices are housed in a manifold. In one embodiment, the manifold is configured to heat liquid prior to the liquid entering one or more microfluidic devices (one example of "just in time" heating). In one embodiment, said liquid is heated after it is displaced and while it begins flowing into said one or more fluidic devices (another example of "just in time" heating). In one embodiment, the manifold is temperature controlled. In one embodiment, the manifold is temperature controlled by enclosing the manifold in an incubator (allowing for the microfluidic devices to be exposed to temperatures consistent with cell growth and viability, such as 37° C.+/−2 degrees, as well as proper humidity and $CO_2$ levels). In one embodiment, the incubator or the manifold comprises a temperature sensor. In one embodiment, resistance to flow is introduced through tubing (e.g. capillary tubing) connecting the flexible reservoirs to the manifold. In one embodiment, resistance can be manipulated by changing the cross-sectional diameter of the capillary tubing. By applying resistance to flow, greater control over flow is achieved. More specifically, by providing resistance one can achieve equal flow rates across multiple chips. By increasing resistance, one can reduce flow rate variability across multiple microfluidic devices. In one embodiment, the method further comprises cooling said working fluid. In one embodiment, said working fluid is cooled with a cooling conduit (surrounding the container, outside the container, internal to the container, or a combination of both) comprising a cooling fluid, wherein said cooling fluid does not mix with said working fluid or with said liquid. In one embodiment, said cooling conduit comprises stainless steel tubing. In one embodiment, said liquid is heated after it is displaced but prior to it flowing into said one or more fluidic devices (one example of "just in time" heating). In one embodiment, said liquid is heated after it is displaced and while it begins flowing into said one or more fluidic devices (another example of "just in time" heating).

It is not intended that the present invention be limited by the nature of the microfluidic device. In one embodiment, the microfluidic device comprises one or more microfluidic channels. In one embodiment, the microfluidic device comprises inlet and outlet ports, said inlet and outlet ports in fluidic communication with said one or more microfluidic channels.

In still another embodiment, the present invention contemplates a method of introducing reagent into microfluidic devices comprising: 1) providing an assembly, comprising a) one or more flexible cell culture media reservoirs and b) one or more flexible reagent reservoirs contained within c) a container, said container i) in fluidic communication with d) a pump and e) a working fluid reservoir and ii) comprising a working fluid (liquid or gas), said flexible cell culture reservoirs i) in fluidic communication with d) one or more microfluidic devices comprising cells on a surface and ii) comprising cell culture media (preferably degassed media), said one or more flexible reagent reservoirs i) in fluidic communication with one or more microfluidic devices and ii) comprising reagent, wherein there is no contact or mixing of said working fluid with said cell culture media; 2) pumping said working fluid into said container with said pump under conditions that the culture media in the flexible reservoirs is displaced and flows into said one or more microfluidic devices, thereby perfusing said cells, wherein reagent in said flexible reagent reservoirs is not displaced; and 3) pumping said working fluid into said container with said pump under conditions that the reagent in at least one flexible reagent reservoir is displaced and flows into said one or more microfluidic devices, thereby introducing reagent into said one or more microfluidic devices. In one embodiment, reagent is introduced in zero gravity or conditions of microgravity. In one embodiment, said surface is a microfluidic channel or portion thereof. In one embodiment, said surface is a membrane. In one embodiment, wherein said assembly further comprises valves to control the flow of said culture media out of said flexible cell culture media reservoirs and valves to control the flow of reagent out of said flexible reagent reservoirs (e.g. the method can comprise controlling the valves, such as by opening or closing valves so as to permit or block flow, respectively). In one embodiment, a valve prevents reagent in said flexible reagent reservoir from being displaced in step 2). In one embodiment, a valve permits reagent in at least one of said flexible reagent reservoir to be displaced in step 3). In one embodiment, said one or more microfluidic devices are outside said container. In one embodiment, said one or more microfluidic devices are housed in a manifold. In one embodiment, the manifold is configured to heat liquid prior to the liquid entering one or more microfluidic devices (one example of "just in time" heating). In one embodiment, said liquid is heated after it is displaced and while it begins flowing into said one or more fluidic devices (another example of "just in time" heating). In one embodiment, the manifold is temperature controlled. In one embodiment, the manifold is temperature controlled by enclosing the manifold in an incubator (allowing for the microfluidic devices to be exposed to temperatures consistent with cell growth and viability, such as 37° C.+/−2 degrees, as well as proper humidity and $CO_2$ levels). In one embodiment, the incubator or the manifold comprises a temperature sensor. In one embodiment, resistance to flow is introduced through tubing (e.g. capillary tubing) connecting the flexible reservoirs to the manifold. In one embodiment, resistance can be manipulated by changing the cross-sectional diameter of the capillary tubing. By applying resistance to flow, greater control over flow is achieved. More specifically, by providing resistance one can achieve equal flow rates across multiple chips. By increasing resistance, one can reduce flow rate variability across multiple microfluidic devices.

Again, it is not intended that the present invention be limited to only one type of container for containing the internal reservoirs. In one embodiment, said container is rigid. In one embodiment, said container is flexible. In one embodiment, said container is collapsible. In one embodiment, said container is insulated or placed within a second container that is insulated. In one embodiment, the insulation comprises foam. In one embodiment, the insulation comprises reflective material. In one embodiment, the insulation comprises vacuum sealing. In one embodiment, said insulation is achieved via spaces of vacuum pressure between container walls. In one embodiment, multiple the insulation comprises vacuum pressure between multiple container walls (2, 3, 4, etc.) In one embodiment, the insulation is achieved via double-walled vacuum insulation. In one embodiment, said container is sealed such that said working fluid can only enter or exit the container through conduits. In one embodiment, the working fluid surrounds at least one internal reservoir. In one embodiment, the working fluid surrounds a plurality of internal reservoirs. In one embodiment, there is more than one container, each container containing working fluid surrounding at least one internal reservoir.

Again, it is not intended that the present invention be limited by the nature of the microfluidic device. In one embodiment, the microfluidic device comprises one or more microfluidic channels. In one embodiment, the microfluidic device comprises inlet and outlet ports, said inlet and outlet ports in fluidic communication with said one or more microfluidic channels.

In one embodiment, the method further comprises cooling said working fluid. In one embodiment, said working fluid is cooled with a cooling conduit (surrounding the container, outside the container, internal to the container, or a combination of both) comprising a cooling fluid, wherein said cooling fluid does not mix with said working fluid or with said liquid. In one embodiment, said cooling conduit comprises stainless steel tubing. In one embodiment, said one or more microfluidic devices are outside said container. In one embodiment, said one or more microfluidic devices are housed in a manifold. In one embodiment, the manifold is configured to heat liquid prior to the liquid entering one or more microfluidic devices (one example of "just in time" heating). In one embodiment, said liquid is heated after it is displaced and while it begins flowing into said one or more fluidic devices (another example of "just in time" heating). In one embodiment, the manifold is temperature controlled. In one embodiment, the manifold is temperature controlled by enclosing the manifold in an incubator (allowing for the microfluidic devices to be exposed to temperatures consistent with cell growth and viability, such as 37° C.+/−2 degrees, as well as proper humidity and $CO_2$ levels). In one embodiment, the incubator or the manifold comprises a temperature sensor. In one embodiment, resistance to flow is introduced through tubing (e.g. capillary tubing) connecting the flexible reservoirs to the manifold. In one embodiment, resistance can be manipulated by changing the cross-sectional diameter of the capillary tubing. By applying resistance to flow, greater control over flow is achieved. More specifically, by providing resistance one can achieve equal flow rates across multiple chips. By increasing resistance, one can reduce flow rate variability across multiple microfluidic devices.

In still another embodiment, the present invention contemplates a method of collecting samples from fluid devices (including microfluidic devices), comprising: 1) providing an assembly, comprising a) one or more flexible reservoirs contained within b) a container, said container i) in fluidic communication with c) a pump and d) a working fluid reservoir and ii) comprising a working fluid (liquid or gas), said flexible reservoirs i) in fluidic communication with e) one or more fluidic devices and ii) comprising liquid (e.g. media such as cell culture media, and most preferably degassed media), said one or more fluidic devices i) in fluidic communication with a sampling conduit and (optionally) ii) comprising cells on a surface, wherein there is no mixing of said working fluid with said liquid; 2) pumping said working fluid into said container with said pump under conditions that the liquid in the flexible reservoirs is displaced and flows into said one or more fluidic devices, thereby causing fluid to exit said one or more fluidic devices and enter said sampling conduit; and 3) collecting samples from said sampling conduit. In one embodiment, the method further comprises 4) storing said samples in said sampling conduit (e.g. in a manner similar to how ice cores are stored, i.e. with the different chronological samples stored together in one continuous conduit). In one embodiment, samples enter said sampling conduit in zero gravity or microgravity conditions. In one embodiment, the method further comprises introducing gas (including but not limited to air) into said sampling conduit to separate said fluid into discrete volumes. In one embodiment, the sampling conduit is cooled by positioning it (or just storing it) inside the rigid reservoir (or some other body or fluid that controls the temperature or, optionally dissolves gases); this, of course, cools the samples as well. Cooling the samples ensures their longevity, and this is a convenient way of doing so that is possibly much more effective than the cooling of samples stored in plates. In one embodiment, one can also dial the separation gas (e.g. air) plug in the "ice core sampling" to be long enough to push the liquid sample from the manifold to the cold storage region, so that the sample gets cooled very quickly.

Again, a variety of container types is contemplated. In one embodiment, said container is rigid. In one embodiment, said container is flexible. In one embodiment, said container is collapsible. In one embodiment, said container is insulated or placed within a second container that is insulated. In one embodiment, the insulation comprises foam. In one embodiment, the insulation comprises reflective material. In one embodiment, the insulation comprises vacuum sealing. In one embodiment, said insulation is achieved via spaces of vacuum pressure between container walls. In one embodiment, multiple the insulation comprises vacuum pressure between multiple container walls (2, 3, 4, etc.) In one embodiment, the insulation is achieved via double-walled vacuum insulation. In one embodiment, said container is sealed such that said working fluid can only enter or exit the container through conduits. In one embodiment, the working fluid surrounds at least one internal reservoir. In one embodiment, the working fluid surrounds at plurality of internal reservoirs. In one embodiment, there is more than one container, each container containing working fluid surrounding at least one internal reservoir. In one embodiment, the method further comprises cooling said working fluid. In one embodiment, said working fluid is cooled with a cooling conduit (surrounding the container, outside the container, internal to the container, or a combination of both) comprising a cooling fluid, wherein said cooling fluid does not mix with said working fluid or with said liquid. In one embodiment, said cooling conduit comprises stainless steel tubing. In one embodiment, said liquid is heated after it is displaced but prior to it flowing (or while it is flowing) into said one or more fluidic devices.

Again, it is not intended that the present invention be limited by the nature of the microfluidic device. In one embodiment, the microfluidic device comprises one or more microfluidic channels. In one embodiment, the microfluidic device comprises inlet and outlet ports, said inlet and outlet ports in fluidic communication with said one or more microfluidic channels.

In still another embodiment, the present invention contemplates a method of recirculating culture media through microfluidic devices without reversing the direction of fluid flow, comprising: 1) providing an assembly, comprising a) one or more flexible reservoirs contained within b) a container, said container i) in fluidic communication with c) a pump and d) a working fluid reservoir and ii) comprising a working fluid, said flexible reservoirs i) in fluidic communication with e) one or more microfluidic devices and ii) comprising cell culture media (preferably degassed media), said one or more microfluidic devices comprising i) cells on a surface and ii) inlet and outlet ports, said inlet and outlet ports in fluidic communication with a recirculation pathway, wherein there is no mixing of said working fluid with said cell culture media (for example, the working fluid does not flow into or through the microfluidic devices); and 2) pumping said working fluid into said rigid container with said pump under conditions that the culture media in the flexible reservoirs is displaced and flows into said one or more microfluidic devices in a direction, thereby causing fluid to exit said outlet port of said one or more microfluidic devices and enter said recirculation pathway, moving in the direction of said inlet port of said one or more microfluidic devices. In one embodiment, said pumping causes said fluid moving in the direction of said inlet port to reach said inlet port, thereby recirculating said culture media without reversing the direction of fluid flow. In one embodiment, said culture media is recirculated in zero gravity or microgravity conditions. In one embodiment, said one or more microfluidic devices are housed on a manifold. In one embodiment, the manifold is configured to heat liquid prior to the liquid entering one or more microfluidic devices (e.g. "just in time" heating). In one embodiment, the manifold is temperature controlled. In one embodiment, the manifold is temperature controlled by enclosing the manifold in an incubator (allowing for the microfluidic devices to be exposed to temperatures consistent with cell growth and viability, such as 37° C.+/−2 degrees, as well as proper humidity and $CO_2$ levels). In one embodiment, the incubator or the manifold comprises a temperature sensor. In one embodiment, resistance to flow is introduced through tubing (e.g. capillary tubing) connecting the flexible reservoirs to the manifold. In one embodiment, resistance can be manipulated by changing the cross-sectional diameter of the capillary tubing. By applying resistance to flow, greater control over flow is achieved. More specifically, by providing resistance one can achieve equal flow rates across multiple chips. By increasing resistance, one can reduce flow rate variability across multiple microfluidic devices. In one embodiment, said recirculation pathway is positioned on said manifold.

Again, it is not intended that the present invention be limited to any one container type. In one embodiment, said container is rigid. In one embodiment, said container is flexible. In one embodiment, said container is collapsible. In one embodiment, said container is insulated or placed within a second container that is insulated. In one embodiment, the insulation comprises foam. In one embodiment, the insulation comprises reflective material. In one embodiment, the insulation comprises vacuum sealing. In one embodiment, said insulation is achieved via spaces of vacuum pressure between container walls. In one embodiment, multiple the insulation comprises vacuum pressure between multiple container walls (2, 3, 4, etc.) In one embodiment, the insulation is achieved via double-walled vacuum insulation. In one embodiment, said container is sealed such that said working fluid can only enter or exit the container through conduits. In one embodiment, the working fluid surrounds at least one internal reservoir. In one embodiment, the working fluid surrounds a plurality of internal reservoirs. In one embodiment, there is more than one container, each container containing working fluid surrounding at least one internal reservoir.

In one embodiment, the method further comprises cooling said working fluid. In one embodiment, said working fluid is cooled with a cooling conduit comprising a cooling fluid, wherein said cooling fluid does not mix with said working fluid or with said liquid. In one embodiment, said cooling conduit comprises stainless steel tubing.

It is not intended that the present invention be limited by the nature of the microfluidic device. In one embodiment, the microfluidic device comprises one or more microfluidic channels. In one embodiment, the microfluidic device comprises inlet and outlet ports, said inlet and outlet ports in fluidic communication with said one or more microfluidic channels. In one embodiment, said microfluidic channels comprise cells. In one embodiment, said cells are on a membrane.

In yet another embodiment, the present invention contemplates an assembly, comprising a) one or more flexible reservoirs contained within b) a rigid container (preferably sealed so that material enters or leaves only through conduits), said rigid container comprising a working fluid (gas or liquid), said flexible reservoirs i) in fluidic communication with c) one or more microfluidic devices and ii) comprising cell culture media (preferably degassed media), wherein there is no mixing of (and preferably no contact between) said working fluid with said cell culture media. In one embodiment, said one or more microfluidic devices are outside said rigid container. In one embodiment, said one or more microfluidic devices are housed in a manifold. In one embodiment, said one or more microfluidic devices comprise living cells on a surface. In one embodiment, said surface is a microfluidic channel or portion thereof. In one embodiment, said surface is a membrane. In one embodiment, said rigid container is in fluidic communication with a pump and a working fluid reservoir. In one embodiment, said pump and working fluid reservoir are outside of said rigid container. In one embodiment, said pump is a displacement pump. It is not intended that the present invention be limited by the nature of the microfluidic device. In one embodiment, the microfluidic device comprises one or more microfluidic channels. In one embodiment, the microfluidic device comprises inlet and outlet ports, said inlet and outlet ports in fluidic communication with said one or more microfluidic channels.

In yet another embodiment, the present invention contemplates an assembly, comprising a) a plurality of flexible reservoirs contained within b) a rigid container (preferably sealed so that material enters or leaves only through conduits), said rigid container i) in fluidic communication with c) a pump and d) a working fluid reservoir and ii) comprising a working fluid (gas or liquid), said flexible reservoirs i) in fluidic communication with e) one or more microfluidic devices and ii) comprising cell culture media (preferably degassed media), wherein there is no mixing of (and preferably no contact between) said working fluid with said cell culture media. In one embodiment, said one or more microfluidic devices are outside said sealed rigid container. In one embodiment, said one or more microfluidic devices are housed in a manifold. In one embodiment, said one or more microfluidic devices comprise living cells on a surface. In one embodiment, said surface is a microfluidic channel or portion thereof. In one embodiment, said surface is a membrane. In one embodiment, the assembly further comprises valves to control the flow of said culture media out of said flexible reservoirs (or the flow of said culture media into or out of said microfluidic devices). In one embodiment, the manifold comprises valves associated with each microfluidic device. In one embodiment, the manifold comprises one or more fluid connectors associated with each microfluidic device, said fluid connectors allowing for fluidic communication through conduits with said internal reservoirs. In one embodiment, said pump and working fluid reservoir are outside of said sealed rigid container. In one embodiment, said pump is a displacement pump. In one embodiment, each microfluidic device is in fluidic communication with a sampling conduit and a waste reservoir. It is not intended that the present invention be limited by the nature of the microfluidic device. In one embodiment, the microfluidic device comprises one or more microfluidic channels. In one embodiment, the microfluidic device comprises inlet and outlet ports, said inlet and outlet ports in fluidic communication with said one or more microfluidic channels.

In yet another embodiment, the present invention contemplates an assembly, comprising a) one or more flexible cell culture media reservoirs and b) one or more flexible reagent reservoirs contained within c) a rigid container (preferably sealed so that material enters or leaves only through conduits), said sealed rigid container i) in fluidic communication with d) a pump and e) a working fluid reservoir and ii) comprising a working fluid (liquid or gas), said flexible cell culture reservoirs i) in fluidic communication with d) one or more microfluidic devices and ii) comprising cell culture media (preferably degassed media), said one or more flexible reagent reservoirs i) in fluidic communication with one or more microfluidic devices and ii) comprising reagent, wherein there is no contact or mixing of said working fluid with said cell culture media. In one embodiment, said one or more microfluidic devices are outside said sealed rigid container. In one embodiment, said one or more microfluidic devices are housed in a manifold. In one embodiment, said one or more microfluidic devices comprise living cells on a surface. In one embodiment, said surface is a microfluidic channel or portion thereof. In one embodiment, said surface is a membrane. In one embodiment, the assembly further comprises valves to control the flow of said culture media out of said flexible reservoirs. In one embodiment, the manifold comprises one or more valves associated with each microfluidic device. In one embodiment, the manifold comprises one or more fluid connectors associated with each microfluidic device, said fluid connectors allowing for fluidic communication through conduits with said internal reservoirs. In one embodiment, said pump and working fluid reservoir are outside of said sealed rigid container. In one embodiment, said pump is a displacement pump. In one embodiment, each microfluidic device is in fluidic communication with a sampling conduit and a waste reservoir. In one embodiment, said reagent is selected from the group consisting of a lysate reagent, a fixative reagent and a staining reagent. In one embodiment, the assembly further comprises a cooling conduit comprising a cooling fluid, wherein said cooling fluid does not mix with said working fluid or with said cell culture media. In one embodiment, said cooling conduit comprises stainless steel tubing. In one embodiment, the assembly further comprises a flow rate sensor configured to detect the flow rate of culture fluid.

It is not intended that the present invention be limited by the nature of the microfluidic device. In one embodiment, the microfluidic device comprises one or more microfluidic channels. In one embodiment, the microfluidic device comprises inlet and outlet ports, said inlet and outlet ports in fluidic communication with said one or more microfluidic channels.

In still another embodiment, the present invention contemplates a method of perfusing cells in microfluidic devices, comprising: 1) providing an assembly, comprising a) one or more flexible reservoirs contained within b) a rigid container (that is preferably sealed so as to allow for the entry and exit of material only through conduits), said rigid container i) in fluidic communication with c) a pump and d) a working fluid reservoir and ii) comprising a working fluid (gas or liquid), said flexible reservoirs i) in fluidic communication with e) one or more microfluidic devices comprising cells on a surface, and ii) comprising cell culture media, wherein there is no mixing of (and preferably no contact between) said working fluid with said cell culture media (preferably degassed media); and 2) pumping said working fluid into said rigid container with said pump under conditions that the culture media in the flexible reservoirs is displaced and flows into said one or more microfluidic devices, thereby perfusing said cells. In one embodiment, said cells are perfused in zero gravity or microgravity conditions. In one embodiment, said working fluid is pumped into said container at a flow rate and the displaced liquid flows into said one or more fluidic devices at a flow rate. In one embodiment, the flow rate of the working fluid is the same as the flow rate of the liquid. In one embodiment, the flow rate of the working fluid is the not same as the flow rate of the liquid. In one embodiment, resistance to flow is introduced through tubing (e.g. capillary tubing) connecting the flexible reservoirs to the one or more fluidic devices (or a manifold containing the one or more fluidic devices). In one embodiment, resistance can be manipulated by changing the cross-sectional diameter of the capillary tubing. By applying resistance to flow, greater control over flow is achieved. More specifically, by providing resistance one can achieve equal flow rates across multiple chips. By increasing resistance, one can reduce flow rate variability across multiple microfluidic devices. In one embodiment, wherein said assembly comprises valves to control the flow out of the reservoirs (e.g. the method can comprise controlling the valves, such as by opening or closing valves so as to permit or block flow, respectively). In one embodiment, said one or more microfluidic devices are outside said sealed rigid container. In one embodiment, said one or more microfluidic devices are housed in a manifold. In one embodiment, the manifold comprises one or more valves associated with each microfluidic device. In one embodiment, the manifold comprises one or more fluid connectors associated with each microfluidic device, said fluid connectors allowing for fluidic communication through conduits with said internal reservoirs. In one embodiment, said surface is a microfluidic channel or portion thereof. In one embodiment, said surface is a membrane. In one embodiment, the method further comprises heating said culture media that is displaced prior to it flowing into (or while it is entering) said one or more microfluidic devices.

It is not intended that the present invention be limited by the nature of the microfluidic device. In one embodiment, the microfluidic device comprises one or more microfluidic channels. In one embodiment, the microfluidic device comprises inlet and outlet ports, said inlet and outlet ports in fluidic communication with said one or more microfluidic channels.

In still another embodiment, the present invention contemplates A method of introducing reagent into microfluidic devices comprising: 1) providing an assembly, comprising a) one or more flexible cell culture media reservoirs and b) one or more flexible reagent reservoirs contained within c) a rigid container (which is preferably sealed so that material enters and exits only through conduits), said rigid container i) in fluidic communication with d) a pump and e) a working fluid reservoir and ii) comprising a working fluid (liquid or gas), said flexible cell culture reservoirs i) in fluidic communication with d) one or more microfluidic devices comprising cells on a surface and ii) comprising cell culture media (preferably degassed media), said one or more flexible reagent reservoirs i) in fluidic communication with one or more microfluidic devices and ii) comprising reagent, wherein there is no mixing of (and preferably no contact between) said working fluid with said cell culture media; 2) pumping said working fluid into said rigid container with said pump under conditions that the culture media in the flexible reservoirs is displaced and flows into said one or more microfluidic devices, thereby perfusing said cells, wherein reagent in said flexible reagent reservoirs is not displaced; and 3) pumping said working fluid into said rigid container with said pump under conditions that the reagent in at least one flexible reagent reservoir is displaced and flows into said one or more microfluidic devices, thereby introducing reagent into said one or more microfluidic devices. In one embodiment, said reagent is introduced in zero gravity or microgravity conditions. In one embodiment, said working fluid is pumped into said container at a flow rate and the displaced liquid flows into said one or more fluidic devices at a flow rate. In one embodiment, the flow rate of the working fluid is the same as the flow rate of the liquid. In one embodiment, the flow rate of the working fluid is the not same as the flow rate of the liquid. In one embodiment, resistance to flow is introduced through tubing (e.g. capillary tubing) connecting the flexible reservoirs to the one or more fluidic devices (or a manifold containing the one or more fluidic devices). In one embodiment, resistance can be manipulated by changing the cross-sectional diameter of the capillary tubing. By applying resistance to flow, greater control over flow is achieved. More specifically, by providing resistance one can achieve equal flow rates across multiple chips. By increasing resistance, one can reduce flow rate variability across multiple microfluidic devices. In one embodiment, said assembly further comprises valves to control the flow of said culture media out of said flexible cell culture media reservoirs and valves to control the flow of reagent out of said flexible reagent reservoirs (i.e. the method can further comprise controlling these valves). In one embodiment, a valve prevents reagent in said flexible reagent reservoir from being displaced in step 2). In one embodiment, a valve permits reagent in at least one of said flexible reagent reservoir to be displaced in step 3). In one embodiment, said one or more microfluidic devices are outside said sealed rigid container. In one embodiment, said one or more microfluidic devices are housed in a manifold. In one embodiment, the manifold comprises one or more valves associated with each microfluidic device. In one embodiment, the manifold comprises one or more fluid connectors associated with each microfluidic device, said fluid connectors allowing for fluidic communication through conduits with said internal reservoirs. In one embodiment, said surface is a microfluidic channel or portion thereof. In one embodiment, said surface is a membrane.

In still another embodiment, the present invention contemplates a method of collecting samples from microfluidic devices, comprising: 1) providing an assembly, comprising a) one or more flexible reservoirs contained within b) a rigid container (which is preferably sealed so that material enters and exits only through conduits), said rigid container i) in fluidic communication with c) a pump and d) a working fluid reservoir and ii) comprising a working fluid, said flexible reservoirs i) in fluidic communication with e) one or more microfluidic devices and ii) comprising cell culture media (preferably degassed media), said one or more microfluidic devices i) in fluidic communication with a sampling conduit and ii) comprising cells on a surface, wherein there is no mixing of (and preferably no contact between) said working fluid with said cell culture media; 2) pumping said working fluid into said rigid container with said pump under conditions that the culture media in the flexible reservoirs is displaced and flows into said one or more microfluidic devices, thereby causing fluid to exit said one or more microfluidic devices and enter said sampling conduit; and 3) collecting samples from said sampling conduit. In one embodiment, the method further comprises 4) storing said samples in said sampling conduit (e.g. in a manner similar to how ice cores are stored, i.e. with the different chronological samples stored together in one continuous conduit). In one embodiment, the method further comprises introducing gas (including but not limited to) air into said sampling conduit to separate said fluid into discrete volumes. In one embodiment, the method further comprises introducing liquid such that first and second samples are separated by liquid. In one embodiment, said first and second samples are separated by an immiscible fluid.

In yet another embodiment, the present invention contemplates a method of recirculating culture media through microfluidic devices without reversing the direction of fluid flow, comprising: 1) providing an assembly, comprising a) one or more flexible reservoirs contained within b) a rigid container (which is preferably sealed such that material enters or exits only through conduits), said rigid container i) in fluidic communication with c) a pump and d) a working fluid reservoir and ii) comprising a working fluid, said flexible reservoirs i) in fluidic communication with e) one or more microfluidic devices and ii) comprising cell culture media (preferably degassed media), said one or more microfluidic devices comprising i) cells on a surface and ii) inlet and outlet ports, said inlet and outlet ports in fluidic communication with a recirculation pathway, wherein there is no mixing of (and preferably no contact with) said working fluid with said cell culture media; and 2) pumping said working fluid into said rigid container with said pump under conditions that the culture media in the flexible reservoirs is displaced and flows into said one or more microfluidic devices in a direction, thereby causing fluid to exit said outlet port of said one or more microfluidic devices and enter said recirculation pathway, moving in the direction of said inlet port of said one or more microfluidic devices. In one embodiment, said pumping causes said fluid moving in the direction of said inlet port to reach said inlet port, thereby recirculating said culture media without reversing the direction of fluid flow. In one embodiment, said culture media is recirculated in zero gravity or microgravity conditions. In one embodiment, said culture media that is recirculated is mixed with fresh (not recirculated) media. In one embodiment, said one or more microfluidic devices are housed on a manifold. In one embodiment, said recirculation pathway is positioned on said manifold.

Definitions

The term "microfluidic" as used herein, relates to components where moving fluid is constrained in or directed through one or more channels wherein one or more dimensions are 1 mm or smaller (microscale). Microfluidic devices are described in the U.S. Pat. No. 8,647,861, and the International Patent App. No. PCT/US2014/071611, the contents of each are incorporated herein by reference (such microfluidic devices are also referred to herein as "chips"). Microfluidic channels may be larger than microscale in one or more directions, though the channel(s) will be on the microscale in at least one direction. In some instances, the geometry of a microfluidic channel may be configured to control the fluid flow rate through the channel (e.g. increase channel height to reduce shear). Microfluidic channels can be formed of various geometries to facilitate a wide range of flow rates through the channels.

The term "channels" as used herein, are pathways (whether straight, curved, single, multiple, in a network, etc.) through a medium (e.g., silicon) that allow for movement of liquids and gasses. Channels thus can connect other components, i.e., keep components "in communication" and more particularly, "in fluidic communication" and still more particularly, "in liquid communication." Such components include, but are not limited to, liquid-intake ports and gas vents. Microchannels are channels with dimensions less than 1 millimeter and greater than 1 micron.

The phrases "connected to," "coupled to," "in contact with," and "in communication with" as used herein, refer to any form of interaction between two or more entities, including mechanical, electrical, magnetic, electromagnetic, fluidic, and thermal interaction. For example, in one embodiment, channels in a microfluidic device are in fluidic communication with a fluid source such as a fluid reservoir. Two components may be coupled to each other even though they are not in direct contact with each other. For example, two components may be coupled to each other through an intermediate component (e.g. tubing or other conduit). Thus, a working fluid in a rigid container can be in fluidic communication with a working fluid reservoir via tubing or other conduit.

"Conduits" can be any device for delivering or conveying gas, fluid or electricity and include (but are not limited to) channels, ducts, pipes and tubes. For electricity, conduits are typically wiring or cables.

The term "solid substrate" as used herein, refers to a substrate that may be biological, nonbiological, organic, inorganic, or a combination of any of these, existing as particles, strands, precipitates, gels, sheets, tubing, spheres, containers, capillaries, pads, slices, films, plates, slides, etc.

The solid substrate is preferably flat but may take on alternative surface configurations. For example, the solid substrate may contain raised or depressed regions, such as microfluidic channels and/or inlet and outlet ports. For example, the substrate may be functionalized glass, Si, Ge, GaAs, GaP, SiO2, SiN4, modified silicon, nitrocellulose and nylon membranes, or any one of a variety of gels or polymers such as (poly)tetrafluoroethylene, (poly)vinylidendifluoride, polystyrene, polycarbonate, or combinations thereof. Other suitable solid substrate materials are be readily apparent to those of skill in the art. The surface of the solid substrate may also contain reactive groups, which could be carboxyl, amino, hydroxyl, thiol, or the like. More preferably, the surface will be optically transparent and will have surface Si—OH functionalities, such as are those found on silica surfaces.

The term "porous membrane" as used herein, refers to a material that is flexible. elastic, or a combination thereof with pores large enough to only permit exchange of gases and small chemicals, or large enough to permit migration and transchannel passage of large proteins, and/or portions thereof. The membrane may also be designed or surface patterned to include micro and/or nanoscopic patterns therein such as grooves and ridges, whereby any parameter or characteristic of the patterns may be designed to desired sizes, shapes, thicknesses, filling materials, and the like.

The term "chamber" as used herein, refers to an isolated region of a microchannel that is separated by a porous membrane. For example, the porous membrane may extend longitudinally down the midpoint of a microchannel thereby providing an upper chamber and a lower chamber.

The term "media" refers to a liquid for conveying a substance. In one embodiment, the substance is nutritive, such as in a culture medium.

Valves can control fluid flow. Diaphragm valves (or membrane valves) consists of a valve body with two or more ports, a diaphragm, and a "weir or saddle" or seat upon which the diaphragm closes the valve.

Some embodiments described herein involve "recirculating" media. In such embodiments, a given volume of media (e.g. all of it, a portion of it, etc.) is recirculated, whereas in non-recirculating perfusion, the media is perfused through the system and sent to directly to waste. Secreted factors and waste products in recirculating cultures are recirculated back to the cells, whereas in non-recirculating culture, the secreted factors and waste products are permanently removed.

The term "rigid" refers to the property of a material such that it is not flexible and will not bend.

The term "incubated box" refers to a container, whether the container is rigid, flexible or collapsible, that is designed in such a way as to limit thermal flow across the walls of the container.

The term "occlusion(s)" refers to blockages in conduits, and all the methods of transporting fluids contained in the definition of conduits.

Some embodiments described herein involve a "media flush." In such embodiments, a conduit, suspected to be suffering from one or more occlusions, may be independently flowed through with a flow rate higher than which was previously flowing through it in order to push out the occlusion. Once the occlusion is removed or displaced the flow rate in the conduit may return to the original flow rate optimized for the experiment.

The term "strain-relief part" refers to a fixture used for the function of lessening the stress on wires, conduits, etc. For example, a part that fixes conduits in place so that fluidic connections are more secure is a strain-relief part.

The term "discretization" refers to replacing a continuum of samples for example, with a finite set of separate points, or samples. Discretization may be used to describe separate samples with their own properties, as opposed to a collection of samples grouped together.

The term "discretized" refers to entities which have characterized by discretization, or characterized by separateness from each other.

The term "plugs" refers to discrete segments of fluid in a conduit that may be distinctly different from the fluid on either side of it in the conduit. For example, "sample plugs" may be separated from each other by plugs of inert fluids, liquids and/or gases, such as to be able to easily distinguish the "sample plugs" form the inert plugs and keep the "sample plugs" from mixing. The inert fluid, a gas and/or liquid, may be referred to as "plug media."

The term "plug sampling" refers to collecting specific volumes or plugs of experimental fluid and separating them in a conduit with plugs of inert fluids, gases and/or liquids. In this sample collection setup, separate experimental fluids to be collected are unable to mix.

The term "plug media" refers to the inert fluid between sample plugs in a conduit during the process of plug sampling.

The term "cross over between plugs" refers to when plug samples mix, when plug media mixes, and when plug samples and plug media mix with each other. "Cross over between plugs" may be intentional, unintentional, to be achieved or to be avoided.

While the present invention is not limited to any particular method of heating fluid, in one embodiment, "micromachined" or "microfabricated" heaters are contemplated. Such microfabricated heaters for microfluidic devices for lab-on-a-chip applications comprise channels using deposited conductors such as sputtered metal, alloys, polymers and composites thereof; or conductors prepared by ion implantation. Such heaters and methods for fabricating same are disclosed in U.S. Patent Application No. US20040178879A1, hereby incorporated by reference.

BRIEF DESCRIPTION OF THE FIGURES

FIG. 3A shows the results without resistance (uneven flow), while FIG. 3B shows the results with resistance (more even flow), as seen from output collection tubes.

FIG. 8A is a top view schematic showing six microfluidic devices (or chips) mounted on a manifold, each chip associated with multiple valves and fluidic connectors. FIG. 8B is a side view schematic showing six microfluidic devices (or chips) on a manifold with associated valves and fluid connectors, the manifold contained within an enclosure or "incubator box" for temperature control.

FIG. 9A is a schematic separating out the fluidics for the top microfluidic channel (or TC) in an embodiment of an assembly comprising both reagent reservoirs (a lysate reservoir and a fixative reservoir are shown as examples of reagent reservoirs) and media reservoirs housed within the rigid container, with valves (depicted as unshaded opposing arrows "> <") shown for controlling what fluid enters the chips, as well as the valves shown for controlling what fluid enters the sampling conduit and what fluid enters the waste reservoir. FIG. 9B is a schematic separating out the fluidics for the bottom microfluidic channel (or BC) in an embodiment comprising both reagent reservoirs (a lysate reservoir and a fixative reservoir are shown as examples of reagent reservoirs) and media reservoirs housed within the rigid container, with valves (depicted as unshaded opposing arrows "> <") shown for controlling what fluid enters the chips, as well as the valves shown for controlling what fluid enters the sampling conduit and what fluid enters the waste reservoir.

FIG. 10A is a schematic separating out the fluidics for the top microfluidic channel (or T) in an embodiment of an assembly comprising both reagent reservoirs (a lysate reservoir and a fixative reservoir are shown as examples of reagent reservoirs) and media reservoirs housed within the rigid container, with valves (depicted as unshaded opposing arrows "> <") shown for controlling what fluid enters the chips, as well as the valves shown for controlling what fluid enters the sampling conduit and what fluid enters the waste reservoir. FIG. 10B is a schematic separating out the fluidics for the bottom microfluidic channel (or B) in an embodiment comprising both reagent reservoirs (a lysate reservoir and a fixative reservoir are shown as examples of reagent reservoirs) and media reservoirs housed within the rigid container, with valves (depicted as unshaded opposing arrows "> <") shown for controlling what fluid enters the chips, as well as the valves shown for controlling what fluid enters the sampling conduit and what fluid enters the waste reservoir.

FIG. 13 shows a microprocessor or computer for controlling the operation of the assembly (e.g. the opening and closing of the valves, the environmental conditions of temperature, humidity etc.) and (an optional) air pump.

FIG. 15A is a drawing showing an outer basket concept. FIG. 15B shows an inner drum embodiment, where the tubing is wrapped around the drum.

FIG. 16A is a drawing of a 3D printed header. FIG. 16B is a top view drawing showing how the header engages that ends of the flexible bags or reservoirs. FIG. 16C is a side view drawing showing how the header engages and organizes the flexible bags or reservoirs.

FIG. 17 depicts one embodiment of a bag header engaging a plurality of flexible bags or reservoirs.

FIG. 20A is a side view and FIG. 20B is a top side view, showing the positioning of the working fluid reservoir.

FIG. 21A is a side view and FIG. 21B is a top side view, showing the positioning of the working fluid reservoir and the plurality of microfluidic devices or chips positioned on the manifold.

FIG. 22A is a side view and FIG. 22B is a top side view, showing the positioning of the working fluid reservoir and the plurality of microfluidic devices or chips positioned on the manifold.

FIG. 32 depicts a calculation summary of a mathematical heat transfer model of the internal hardware of the invention. In one embodiment of the invention, a cooling system may generate high levels of waste heat due to theorized inefficiencies. The internal hardware of the invention in that embodiment may have a limitation of how much waste heat it can reject due to the amount of power it can draw. The table illustrates mathematical calculations used to quantify the thermal situation within certain embodiments of the invention.

FIG. 33 shows that even flow across all of the independent, flexible reservoirs or IV bags may be achieved.

DESCRIPTION OF THE INVENTION

The present invention is related to the field of fluidic devices, and in particular, microfluidic cell culture systems. The present invention provides pumping, recirculation and sampling for a microfluidic device or devices. The present invention provides solutions to the control of microfluidics for both terrestrial and space applications, including the control over the movement of fluids in zero gravity or microgravity conditions.

With respect to space, an automated microfluidic research platform is contemplated for use to conduct experiments on the International Space Station (ISS), the platform comprising one or more of the assemblies described herein. Freed from the effects of gravity found on Earth, the International Space Station provides an environment where researchers can study human health in zero gravity or microgravity, allowing them to decouple the force of gravity from other effects that can impact cell function. Thus, embodiments described herein provide a unique research environment for enhancing knowledge to improve human health. The microfluidic devices in fluidic communication with other components of the assembly provide a living, micro-engineered environment that recreates the natural physiology and mechanical forces that cells experience within the human body.

A. Pumping and Moving Fluids

Figure 1:
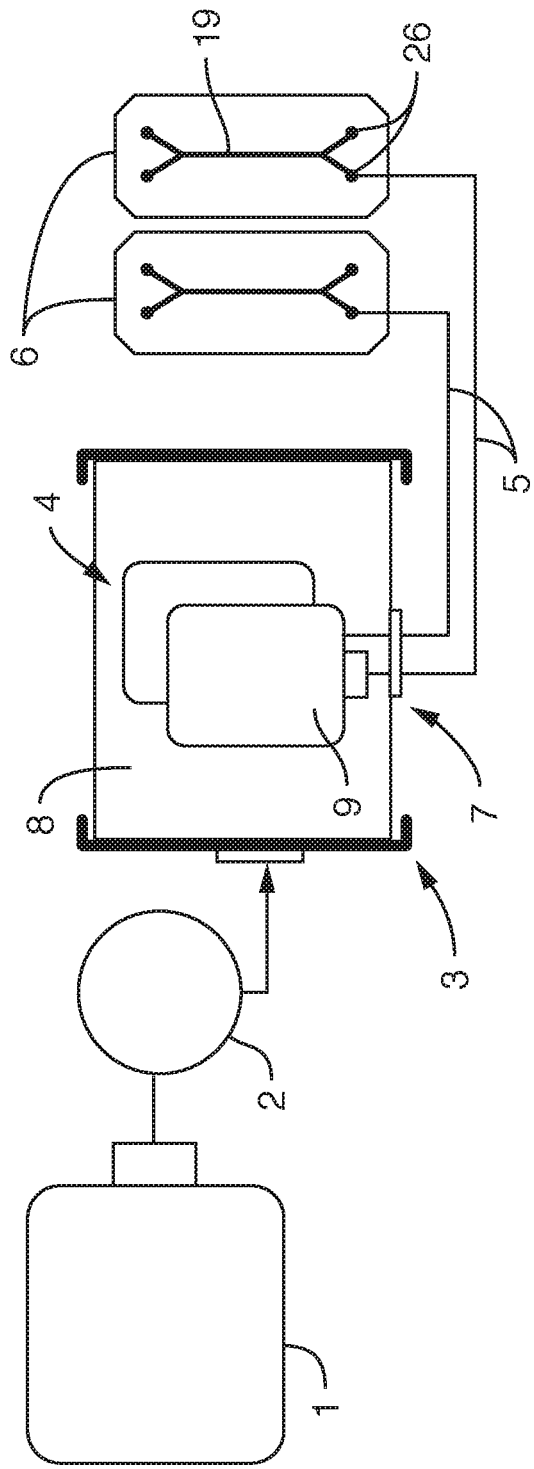
FIG. 1 is a schematic showing one embodiment of an assembly comprising a working fluid reservoir in fluidic communication with a pump in fluidic communication with a rigid container comprising working fluid that surrounds one or more flexible reservoirs, the flexible reservoirs in fluidic communication (via tubing or other conduit) with one or more microfluidic devices comprising inlet and outlet ports in fluidic communication with one or more microfluidic channels (in this case, a two channel microfluidic device).
Figure 28:
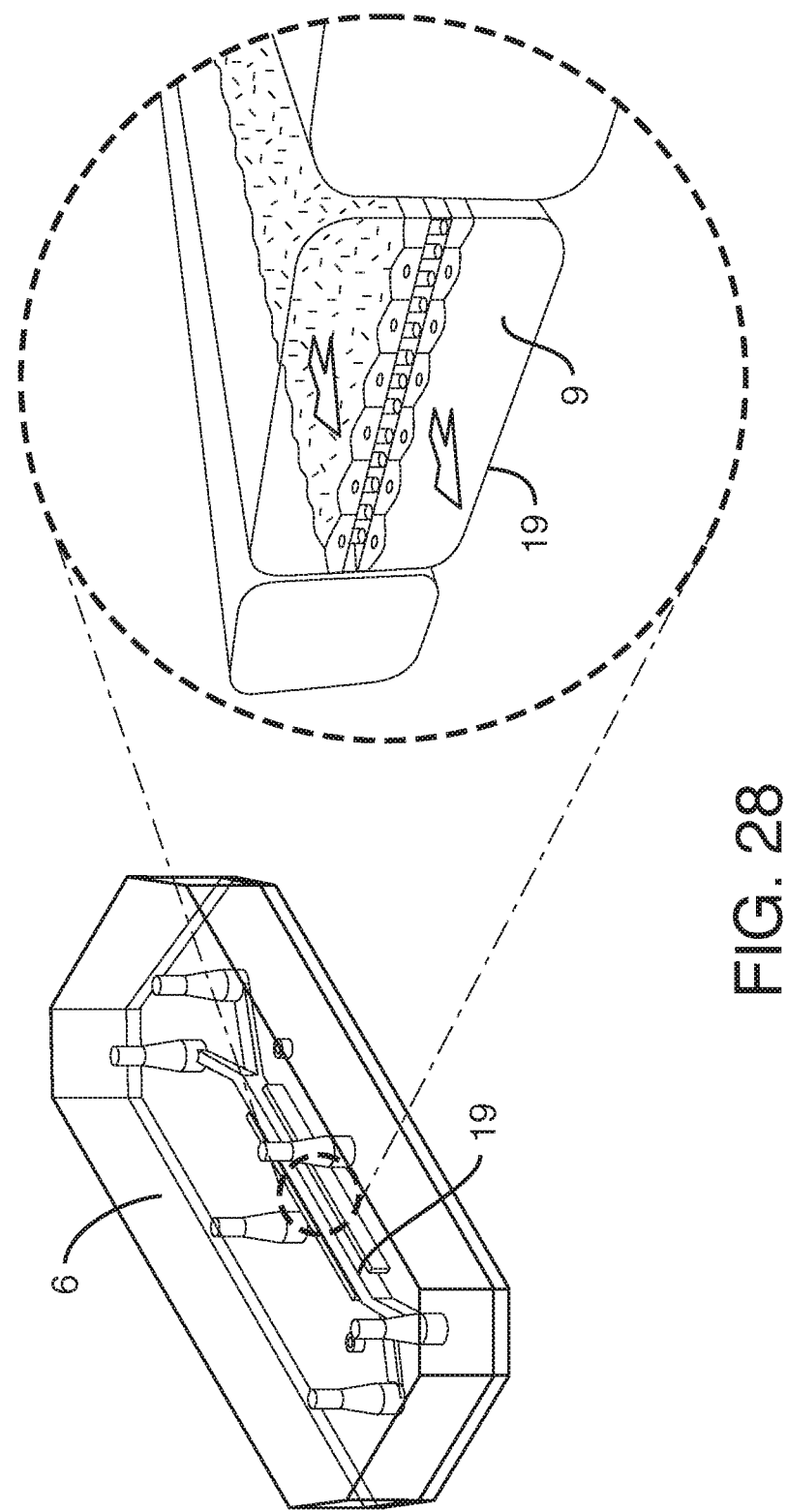
FIG. 28 shows an exemplary microfluidic device or "chip" comprising cells. By way of an example, the chip is comprised of two microchannels (Labeled 1&2) separated by a porous flexible-membrane. The material is functionalized with specific extracellular matrix proteins and cells are seeded into the different channels, e.g. endothelial cells are seeded in the bottom compartment and epithelial cells in the top compartment to emulate the basic functioning unit of an organ. Optionally, vacuum pressure can be applied to the side channels to mechanical stretch the membrane. Fluids can be continuously pumped through the channels to mimic shear forces, bring in nutrients, and wash away waste.
Figure 29A:
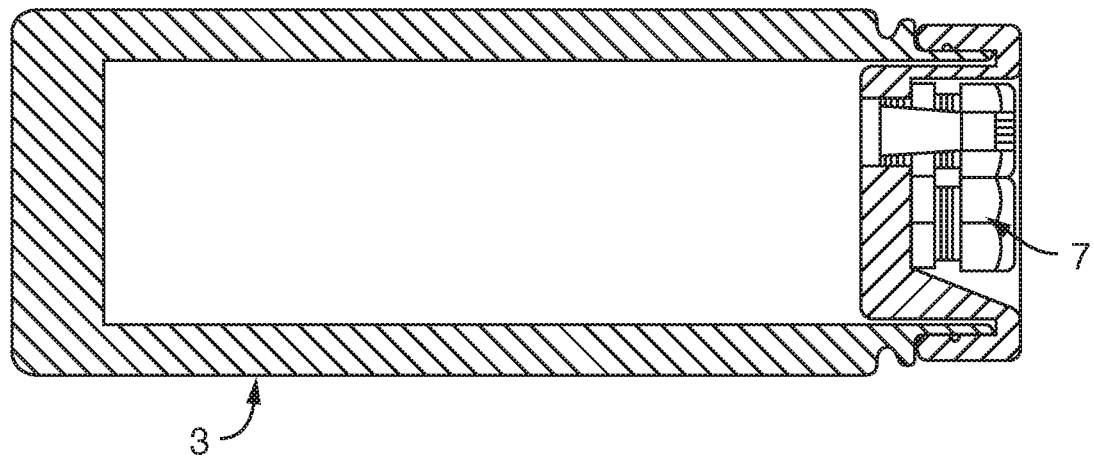
FIGS. 29A and 29B show one embodiment of a double-walled vacuum insulated rigid container for housing flexible media reservoirs or secondary rigid containers. The container had a custom lid integrating strain-relief parts.
Figure 29B:
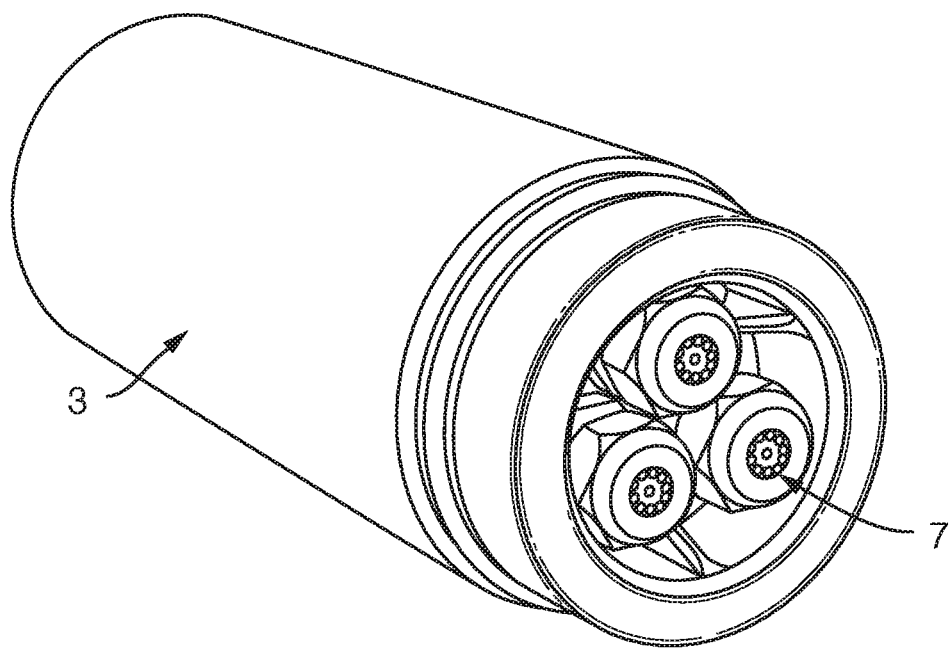
Figure 30:
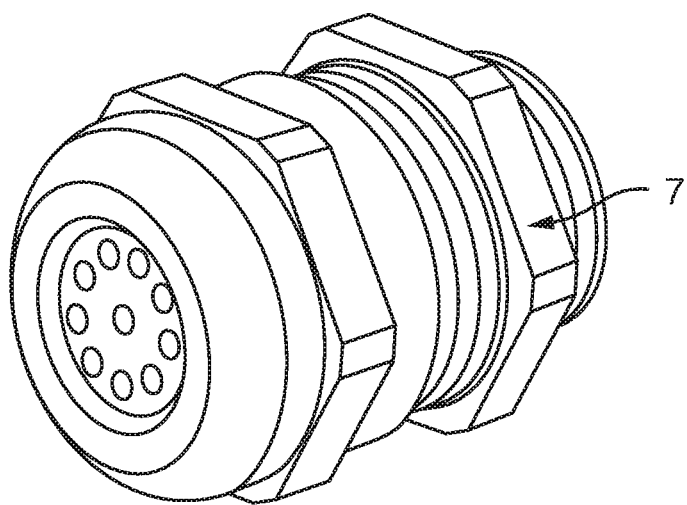
FIG. 30 shows a commercial off-the-shelf part for leak-proof routing of capillary tubes in and out of the rigid container as shown in FIGS. 29A an 29B.

Moving fluids, particular moving fluids in a controlled manner under microgravity conditions, is difficult. In one embodiment, the present invention contemplates an assembly (such as the embodiment shown in FIG. 1), comprising one or more (or a plurality of) flexible reservoirs (4) (such as the flexible IV bags shown in FIG. 14) contained within a container (5) (preferably a rigid reservoir), said container (5) in fluidic communication with a pump (2) and a working fluid reservoir (1) and comprising a working fluid (liquid or gas) (8), said flexible reservoirs (4) in fluidic communication with one or more fluidic devices (including but not limited to microfluidic devices (6) or "chips") and ii) comprising cell culture media, wherein there is no mixing of said working fluid with said cell culture media (preferably degassed media). It is not intended that the present invention be limited to nature or type of container (3) or nature or type of internal reservoirs (4). In one embodiment, said container is rigid. In one embodiment, said container is flexible. In one embodiment, said container is collapsible. In one embodiment, said container is insulated or is housed within a second insulated container. For cell cultures, such as in Organ Chips (6), it is beneficial maintain a temperature of about 37° C. for optimal cell maintenance. For cell media (9) it is beneficial to maintain a temperature of about 4° C. in order to avoid the degradation of key ingredients. Due to size constraints, these two components, optimally maintained at different temperatures, may have to reside next to each other. An insulated container (3) is one embodiment of maintaining these two separate temperatures. In one embodiment, the container comprises multiple (e.g. 2, 3, 4, etc.) vacuum insulated walls as seen in FIGS. 29A and 29B. In one embodiment the container is insulated with a material such as foam, reflective material, etc. In one embodiment the container is insulated with a fluid layer, either a gas or liquid. In one embodiment, said container (3) is sealed such that said working fluid can only enter or exit the container through conduits, such as a commercial off-the-shelf leak-proof capillary tube router (7) seen individually FIG. 30 and as part of the assembly in FIGS. 29A and 28B. In one embodiment, the working fluid (8) surrounds at least one internal reservoir (4). In one embodiment, the working fluid (8) surrounds a plurality of internal reservoirs (4). In one embodiment, there is more than one container (see FIGS. 11, 13, and 19-22), each container containing working fluid surrounding at least one internal reservoir. In one embodiment, said container (3) is rigid and said flexible reservoirs (4) can be compressed (e.g. with pressure via a working fluid) so that the fluid (9) in the bag exits the bag through tubing (5) (such as the embodiment shown in FIG. 2) or other conduit, and moves toward and into the fluidic devices, such as the microfluidic devices (6) shown in FIG. 1, entering and exiting the microfluidic devices via ports (26).

Figure 2:
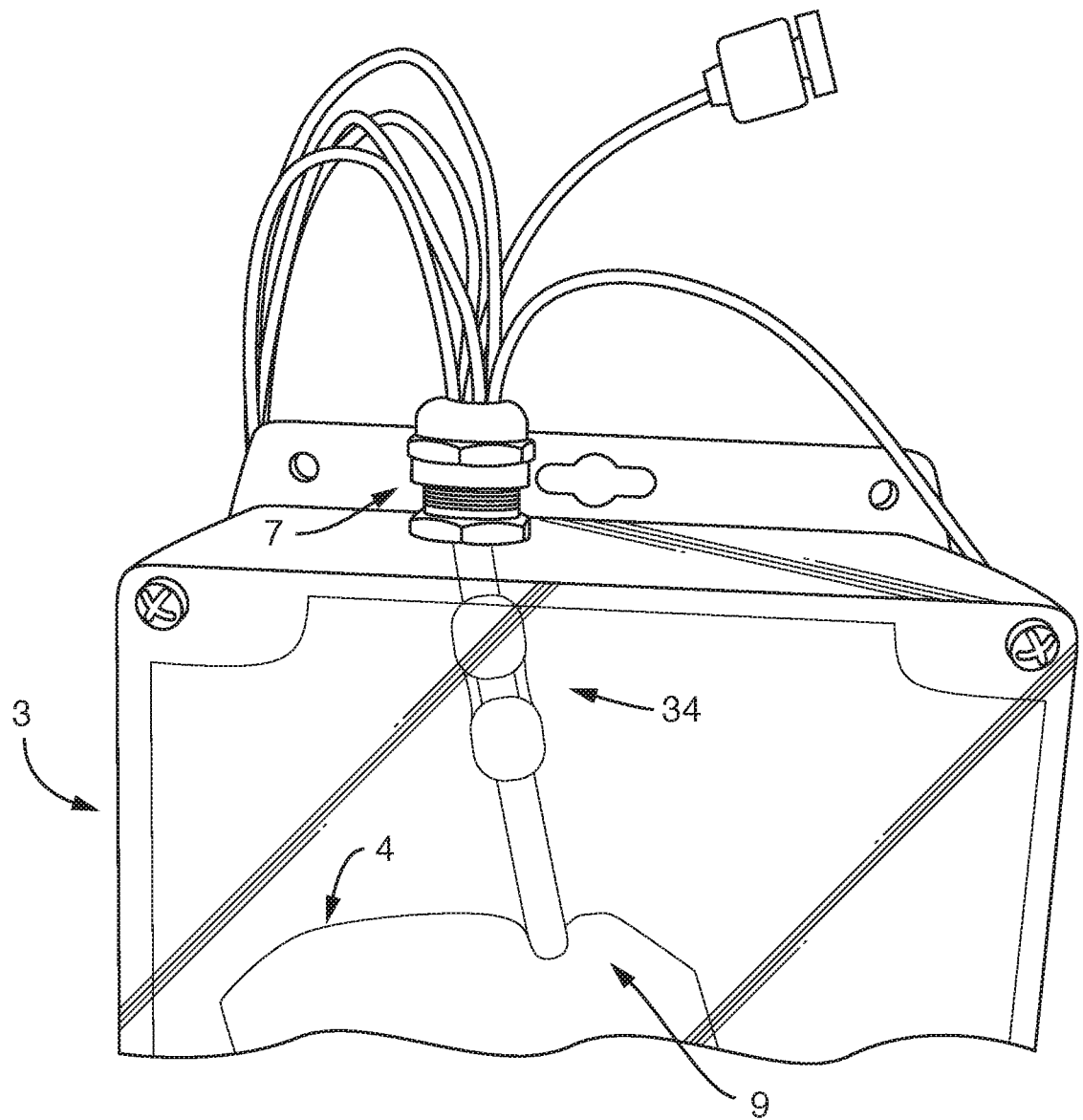
FIG. 2 depicts one embodiment of the pass-through between the rigid container and the outside world. It needs to make a fluid seal around all tubing entering and leaving the container. A grommet (or multi-hole strain relief fitting) connects the flexible reservoir(s) and working fluid to external components of the assembly (e.g. the pump, the working fluid reservoir(s), etc.). Such grommets are available commercially from SealCon, LLC, Centennial, Colorado U.S.A., which has five holes that are 1.6 mm in diameter. As well, fluidic connections, such as luer locks, may be used as seen in FIG. 2.

FIG. 2 depicts one embodiment of the pass-through between the rigid container and the outside world. The rigid container may make a fluid seal around all tubing entering and leaving the container. In one embodiment, a grommet (or multi-hole strain relief fitting) may connect the flexible reservoir(s) and working fluid to external components of the assembly (e.g. the pump, the working fluid reservoir(s), etc.). Such grommets are available commercially from Seal-Con, LLC, Centennial, Colorado U.S.A., which has five holes that are 1.6 mm in diameter. In one embodiment, fluidic connections (34), such as luer locks, may be used to connect the flexible reservoirs (4) to tubing (22).

Figure 9A:
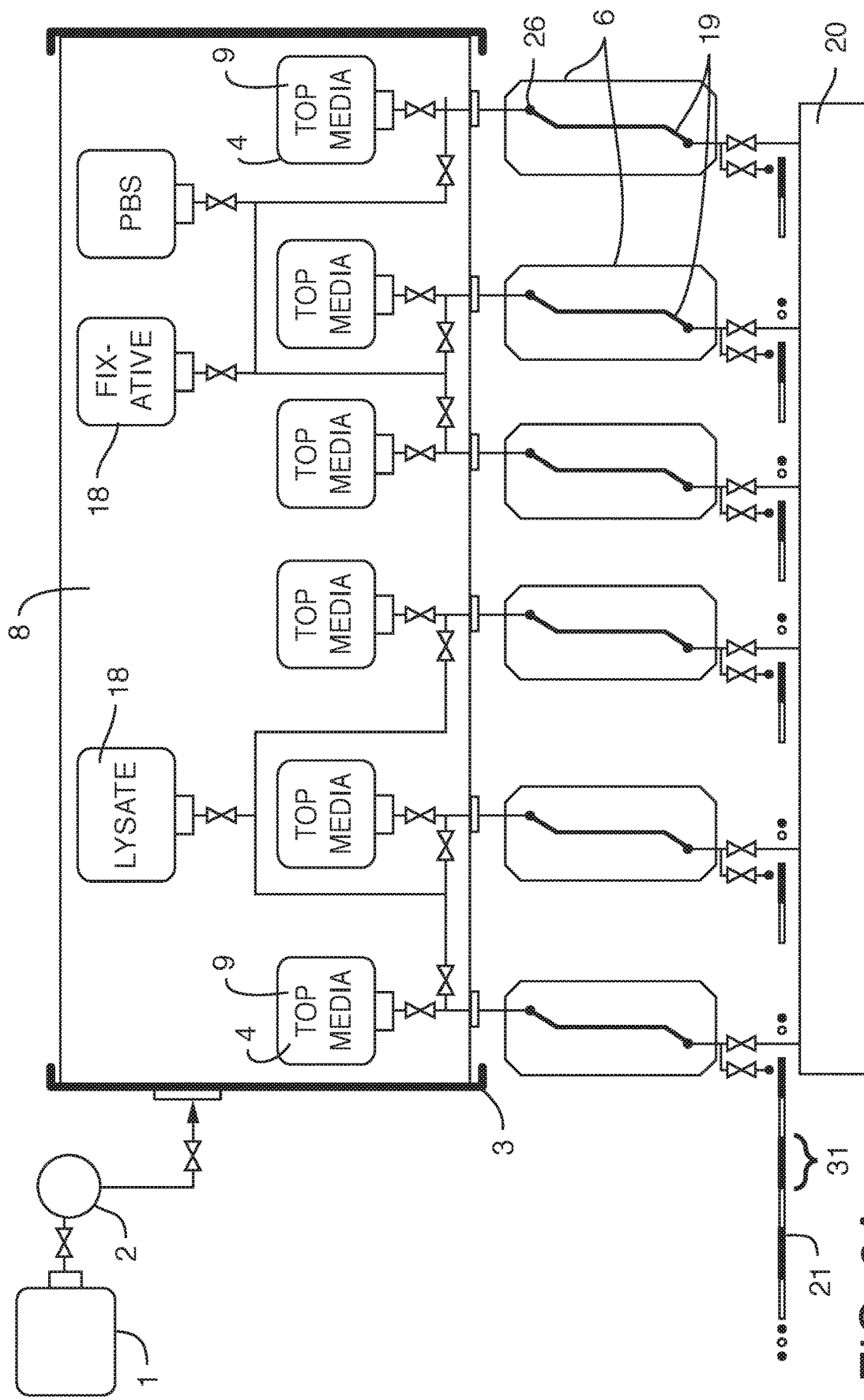
FIGS. 9A and 9B are schematics showing how the six microfluidic devices on a manifold (depicted in FIG. 8A) might be valved, the microfluidic devices (or chips) comprising inlet and outlet ports in fluidic communication with one or more microfluidic channels (in this case, a two-channel microfluidic device, i.e. a device with a top channel and a bottom channel).
Figure 9B:
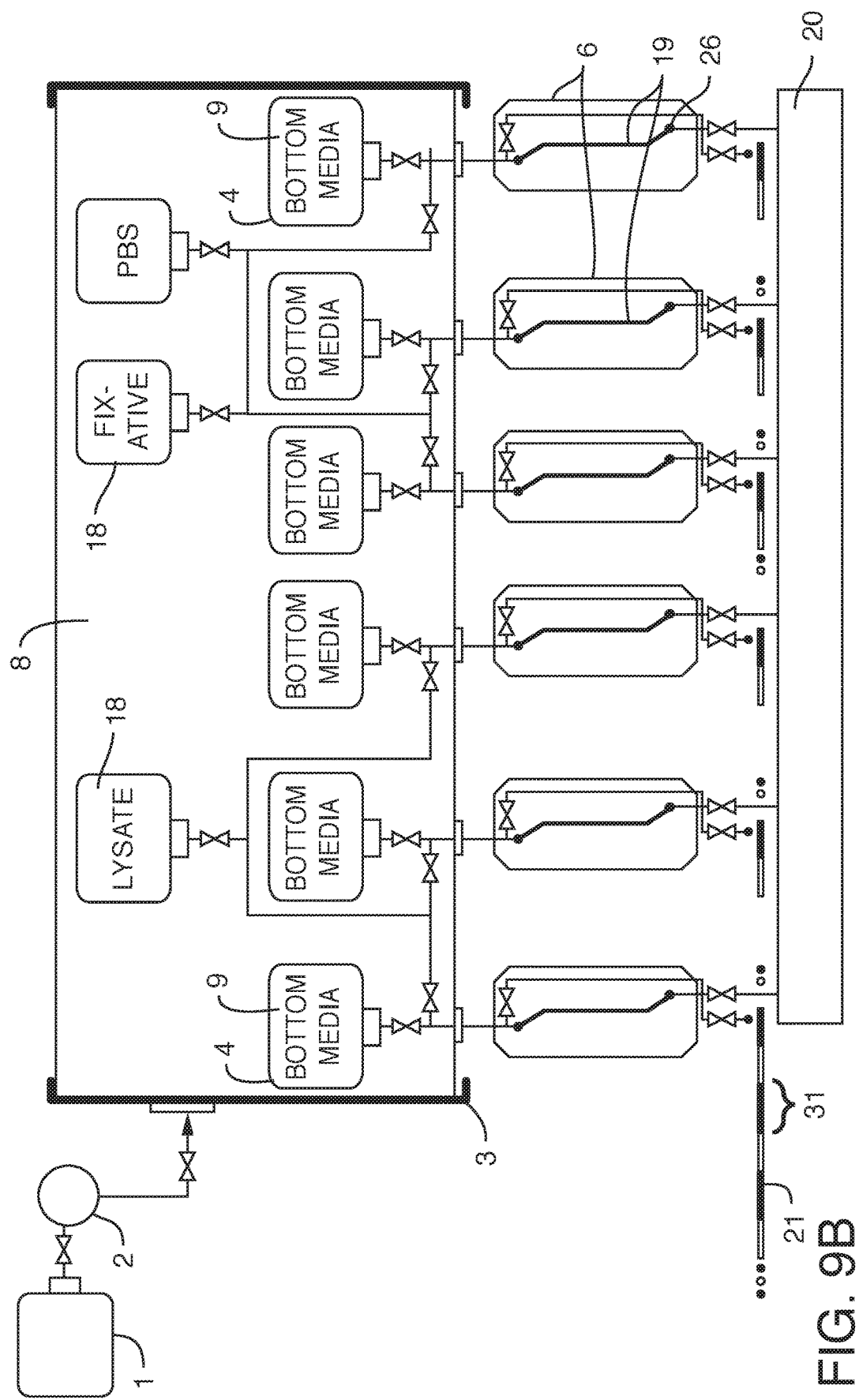

Whether fluid (9) exits the internal reservoir (4) can be controlled further with one or more valves (17) (see FIGS. 9 and 10). Where there is more than one internal reservoir (4), each internal reservoir (4) can comprise a valve (17) to control fluid flow (e.g. in one position the valve blocks the fluid, while in another position the valve permits fluid flow). One or more pressure sensors (14) can be added to the assembly (see FIG. 7) so that clogging of a conduit can be detected and remedied.

Figure 33:
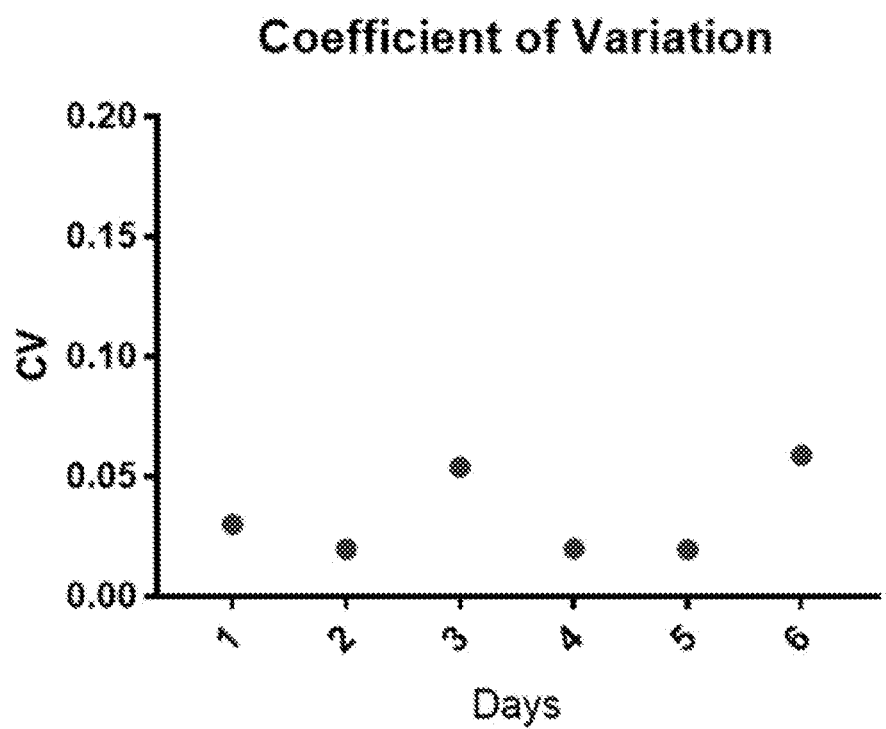
FIG. 33 depicts the coefficient of variation of the flow rate coming out of six flexible reservoirs or IV bags in a rigid reservoir.

In an exemplary embodiment, the invention presented herein has consistent flow rates in order to minimize experiment variability. FIG. 33 depicts the coefficient of variation of the flow rate coming out of six flexible reservoirs or IV bags in a rigid reservoir. FIG. 33 shows that even flow across all of the independent, flexible reservoirs or IV bags may be achieved when desired. However, it is not intended that the present invention be limited by equal flow across all of the flexible reservoirs. Per experiment requirements, flow may be the same or different amongst the one or more flexible reservoirs.

Figure 16C:
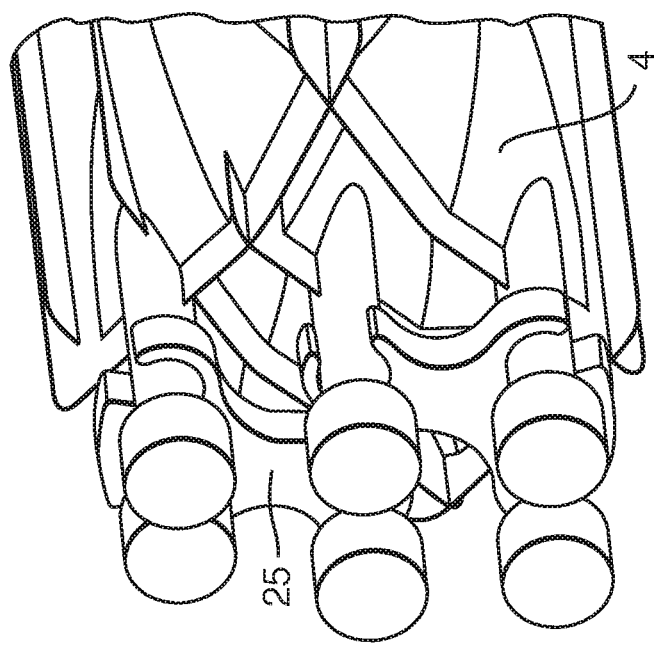
FIGS. 16A, 16B and 16C show one embodiment of a bag header.
Figure 16B:
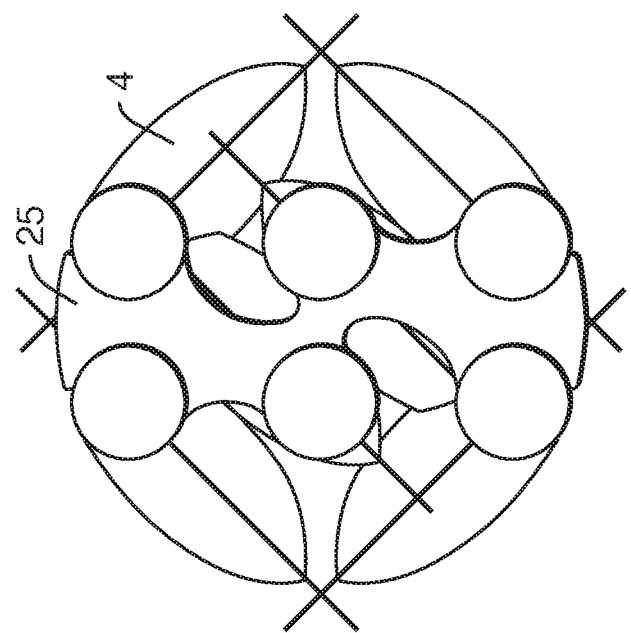
Figure 16A:
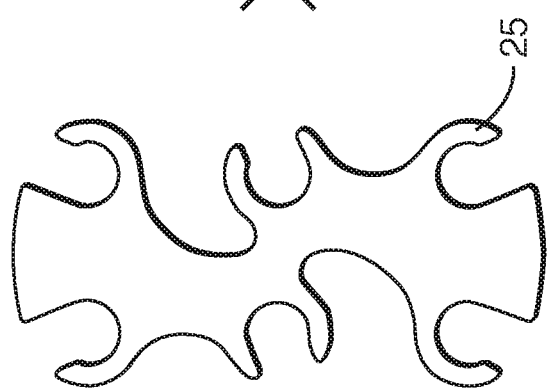

In one embodiment several internal reservoirs are held together using a bag header (25) as seen in FIG. 16A, FIG. 16B and FIG. 16C. The internal reservoirs (4) are oriented in the bag header (25) for the best tube packing density in order to fit into a system of limited size. In one embodiment the bag header (25) is made from stiff material, such as but not limited to plastic. The bag header (25) may be fabricated using 3D printing technology, injection molding, or other methods known by one having ordinary skill in the art. FIG. 17 depicts an alternative view of the internal reservoirs (4) held together using a bag header (25) with one internal reservoir (4) connected to tubing (22).

Figure 8A:
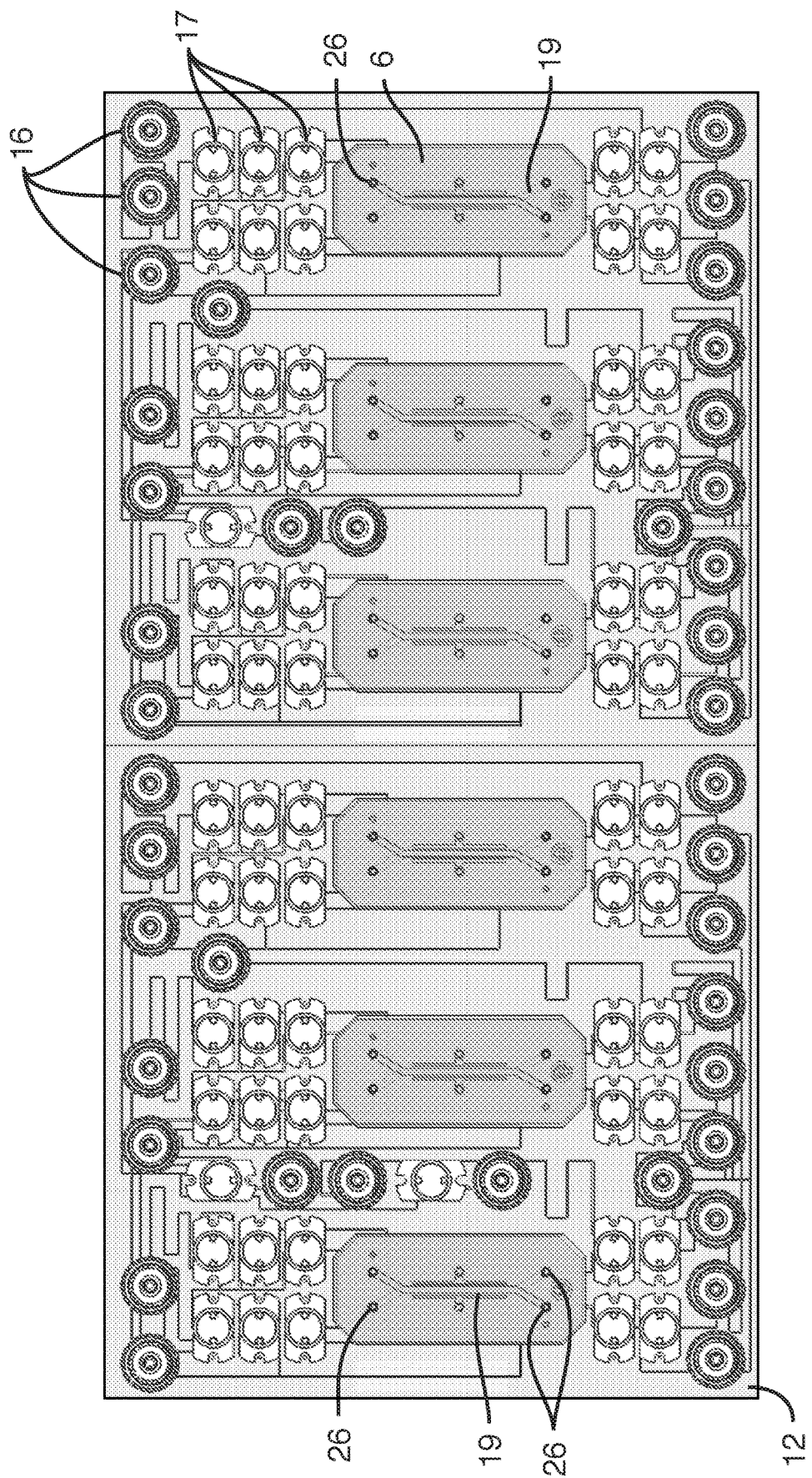
FIGS. 8A and 8B are schematics showing one embodiment of a manifold with microfluidic devices associated with fluidic connectors and valves, the microfluidic devices comprising inlet and outlet ports in fluidic communication with one or more microfluidic channels (in this case, a two-channel microfluidic device).
Figure 8B:
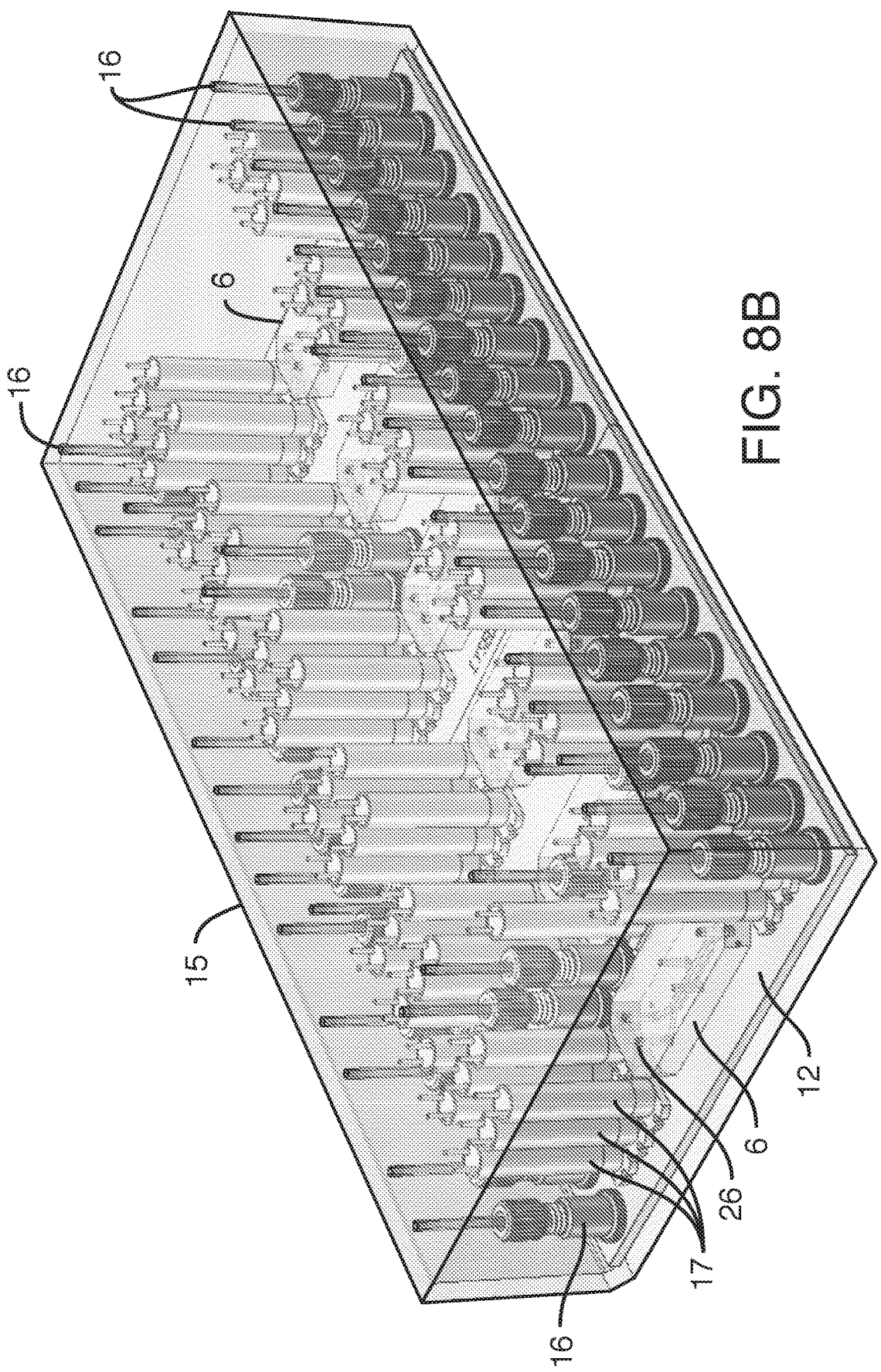

It is not intended that the present invention be limited to the positioning of the microfluidic devices. In a preferred embodiment, said one or more microfluidic devices are outside said container. In one embodiment, said one or more microfluidic devices are housed in a manifold (12) (see FIG. 6, FIGS. 8A and B, FIGS. 10A and B, FIGS. 11, 13, 21B, and 22B) along with one or more valves (17), such as diaphragm valves, and fluidic connectors (16), connecting to external fluid conduits, so that the microfluidic devices (6) on the manifold (12) are in fluidic communication with the reservoirs internal to the container, as well as in fluidic communication with any sampling conduits or recirculation pathways. In one embodiment, the manifold (12) comprises pins to align or even to attach the microfluidic devices (6) to the manifold (12). The manifold can comprise a plurality of microfluidic devices (6), each with their own associated valves (17) and fluidic connectors (16) (FIGS. 8A and 8B). In one embodiment, the manifold (12) is configured to heat liquid (9) prior to the liquid entering one or more microfluidic devices (6) (one example of "just in time" heating). In one embodiment, said liquid (9) is heated after it is displaced and while it begins flowing into said one or more fluidic devices (another example of "just in time" heating). In one embodiment, the manifold (12) is temperature controlled. In one embodiment, the manifold is temperature controlled by enclosing the manifold (12) in an enclosure (FIG. 8B) such as an incubator box (15) (allowing for the microfluidic devices to be exposed to temperatures consistent with cell growth and viability, such as 37° C.+/−2 degrees, as well as proper humidity and $CO_2$ levels). In one embodiment, the incubator box (15) or the manifold (12) itself comprises a temperature sensor.

Figure 13:
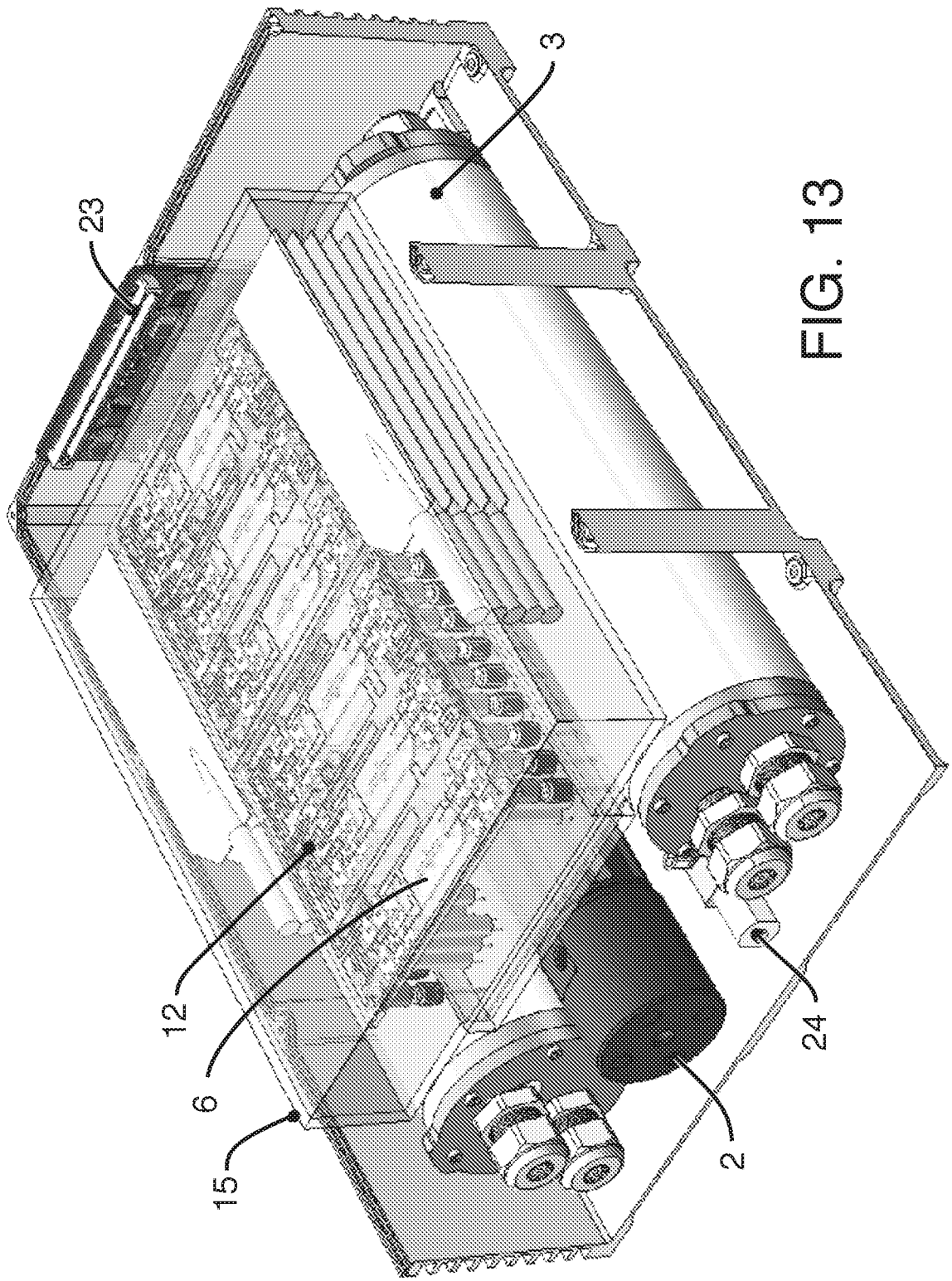
FIG. 13 is a top side view schematic of one embodiment of an assembly comprising two rigid containers (housing flexible reservoirs, not shown) in fluidic communication with a pump for pumping the working fluid and the manifold housing the microfluidic devices, the manifold contained within an enclosure or incubated box.
Figure 14:
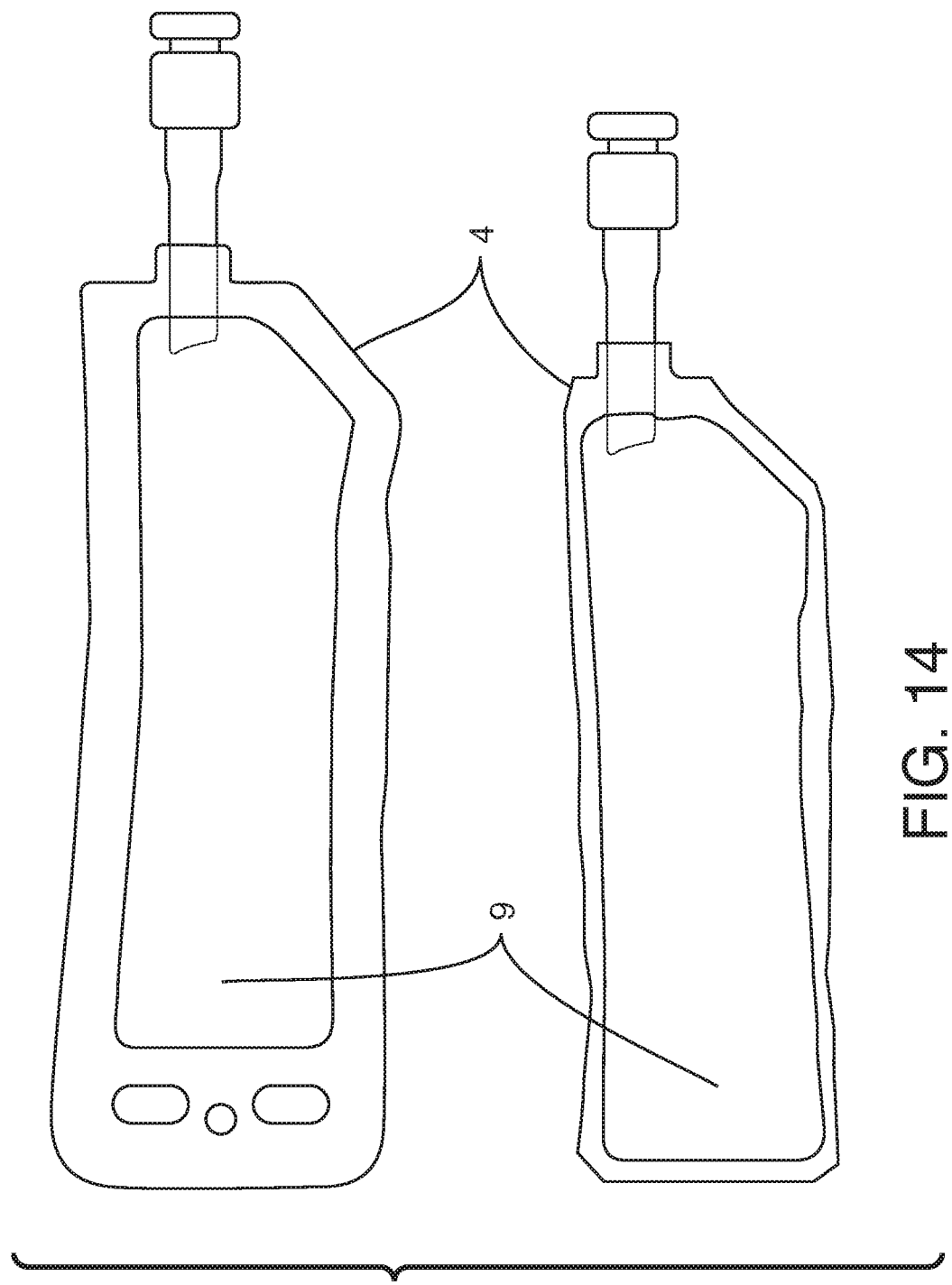
FIG. 14 is a schematic of IV bags suitable (in one embodiment) as flexible reservoirs, including one with trimmed edges.

In one embodiment, an assembly (as seen in FIG. 13) comprises two rigid containers in fluidic communication with a pump for pumping the working fluid and the manifold housing the microfluidic devices, the manifold contained within an enclosure or incubated box. FIG. 13 also shows an embodiment where a microprocessor or computer (23) is used for controlling the operation of the assembly (e.g. the opening and closing of the valves, the environmental conditions of temperature, humidity etc.) and (an optional) air pump (24).

Figure 4:
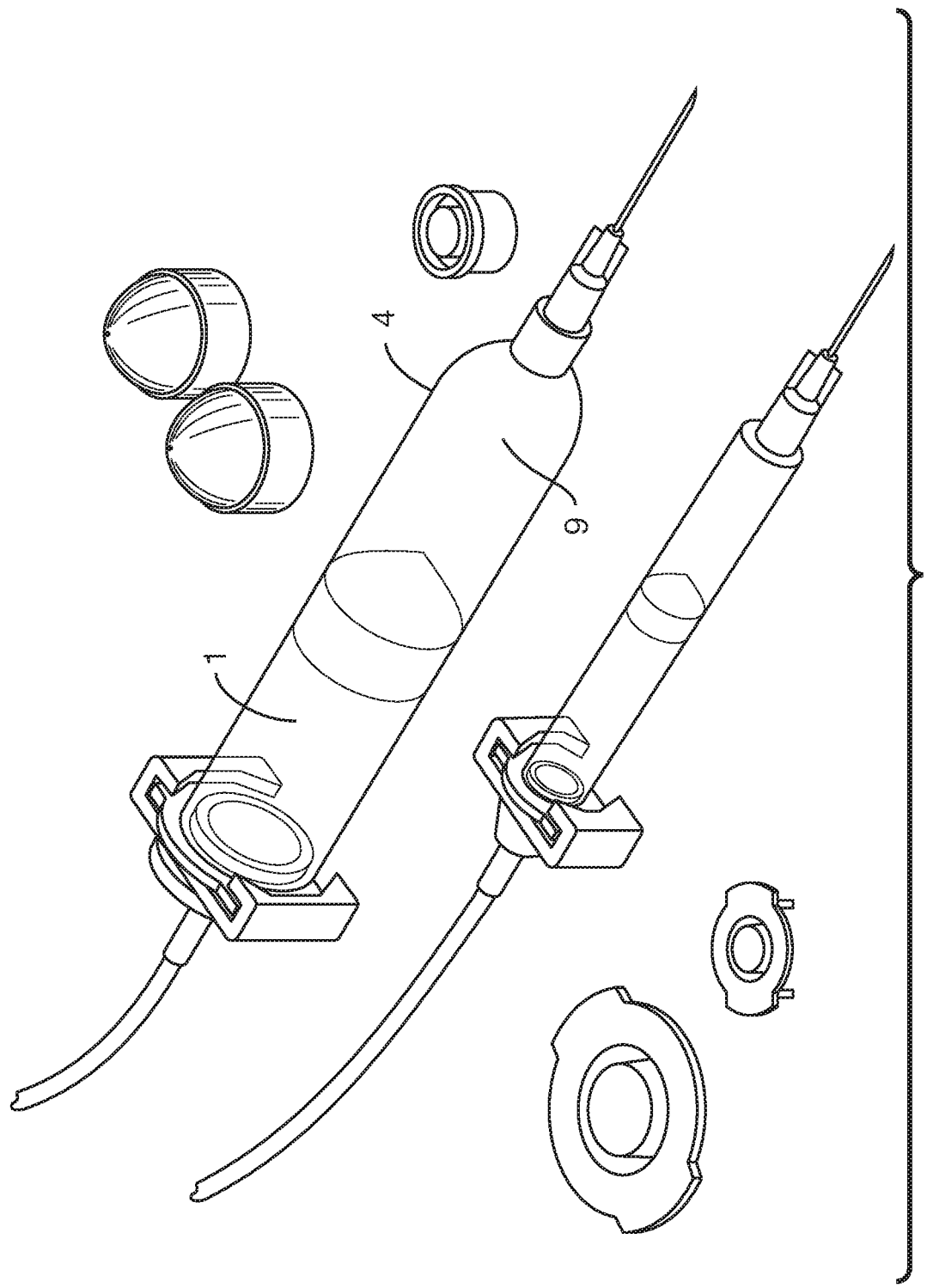
FIG. 4 shows an alternative pump configuration involving a syringe/piston arrangement as part of the total assembly. Thus, the rigid container has a deformable portion (i.e. the piston or plunger).

FIG. 4 shows an alternative pump configuration involving a syringe/piston arrangement as part of the total assembly. Thus, the rigid container (4) has a deformable portion (i.e. the piston or plunger). In this embodiment, the working fluid reservoir (1) is on the opposite side of the deformable portion as the media (9).

Figure 3A:
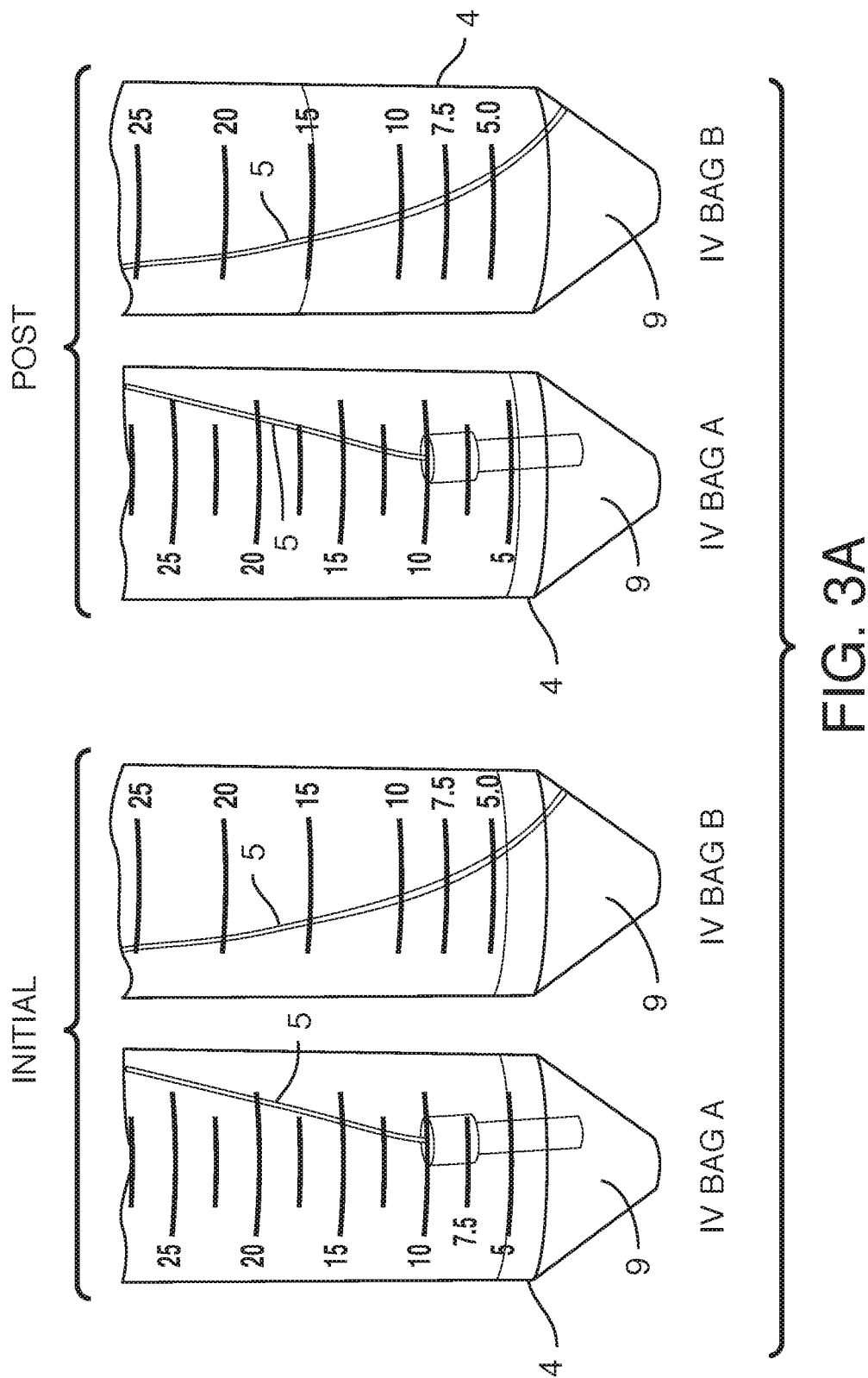
FIGS. 3A and 3B are schematics showing the output flow rates with two reservoirs in the same rigid container of an assembly.
Figure 3B:
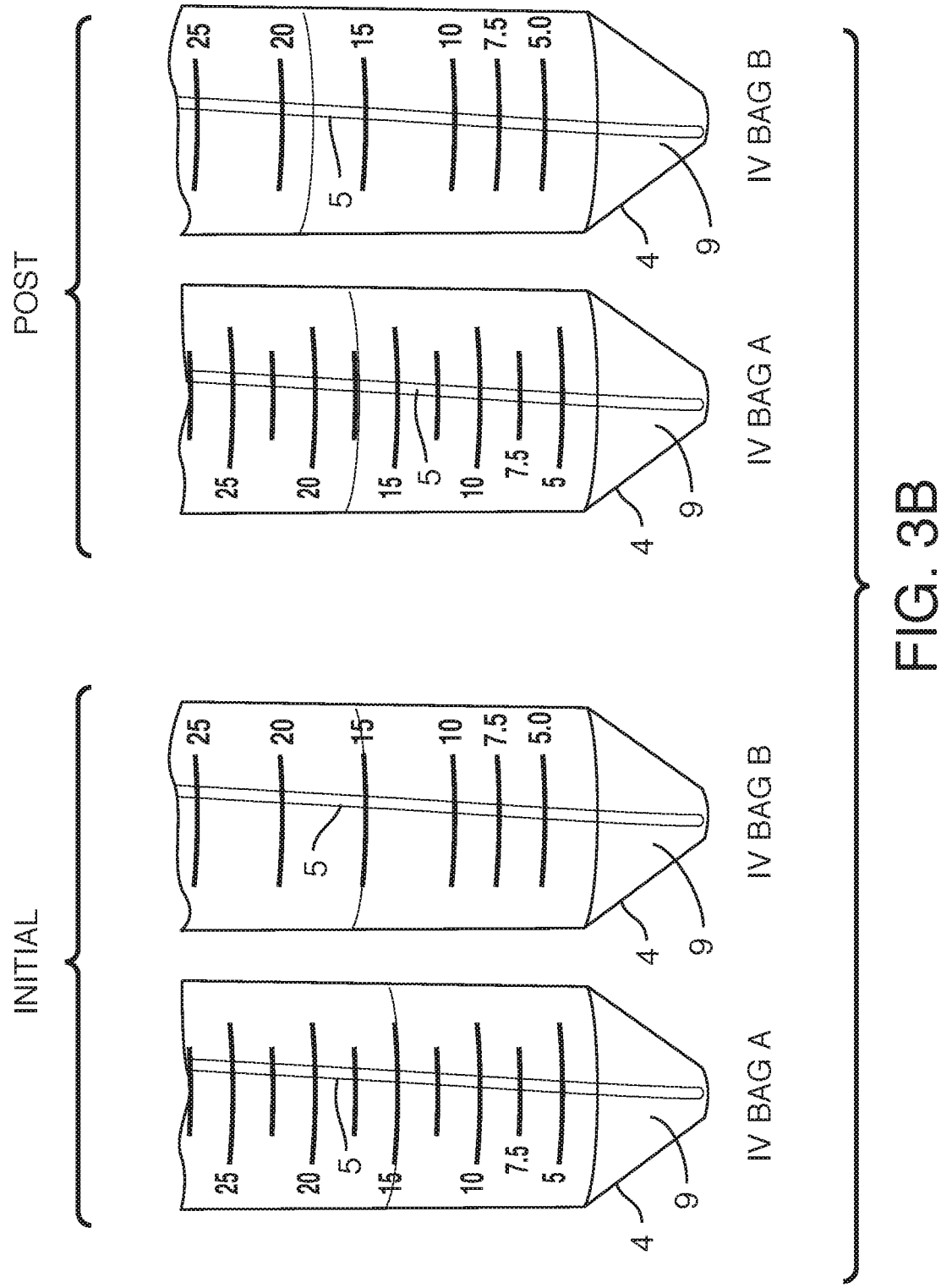

In one embodiment, resistance to flow is introduced through tubing connecting the flexible reservoirs to the manifold (FIG. 12), including but not limited to capillary tubing (22). In one embodiment, resistance can be manipulated by changing the cross-sectional diameter of the capillary tubing (22). By applying resistance to flow, greater control over flow is achieved. More specifically, by providing resistance one can achieve equal flow rates across multiple chips. By increasing resistance, one can reduce flow rate variability across multiple microfluidic devices (compare FIG. 3A with FIG. 3B).

It is not intended that the present invention be limited by the precise design of the fluidic or microfluidic devices (6). In one embodiment, the microfluidic devices have one or more microfluidic channels (19) which are channels with one or more dimensions that are 1 mm or smaller, and more typically 0.1 mm or smaller. The microfluidic device can also have (optionally) membranes. It is preferred that the microfluidic device comprises inlet and outlet ports (26) so that liquid (9) can enter and exit the microfluidic channels (19). In one embodiment, said one or more microfluidic devices (6) comprise living cells (32) on a surface (e.g. see FIG. 28). In one embodiment, said surface is a microfluidic channel (19) or portion thereof. In one embodiment, said surface is a membrane.

In one embodiment, the container is used to cool the working fluid. In one embodiment, the working fluid is used to cool (e.g. the internal reservoirs). In yet another embodiment (FIG. 5), the working fluid (8) is cooled using a cooling conduit (11) which can be aligned with the container (3) in a variety of ways (e.g. surrounding the container, outside the container, internal to the container, or a combination of both). The conduit (11) comprising a cooling fluid which can be in a cooling fluid reservoir (10), wherein said cooling fluid does not mix with said working fluid or with said liquid of the internal reservoirs (e.g. with the media).

Figure 5:
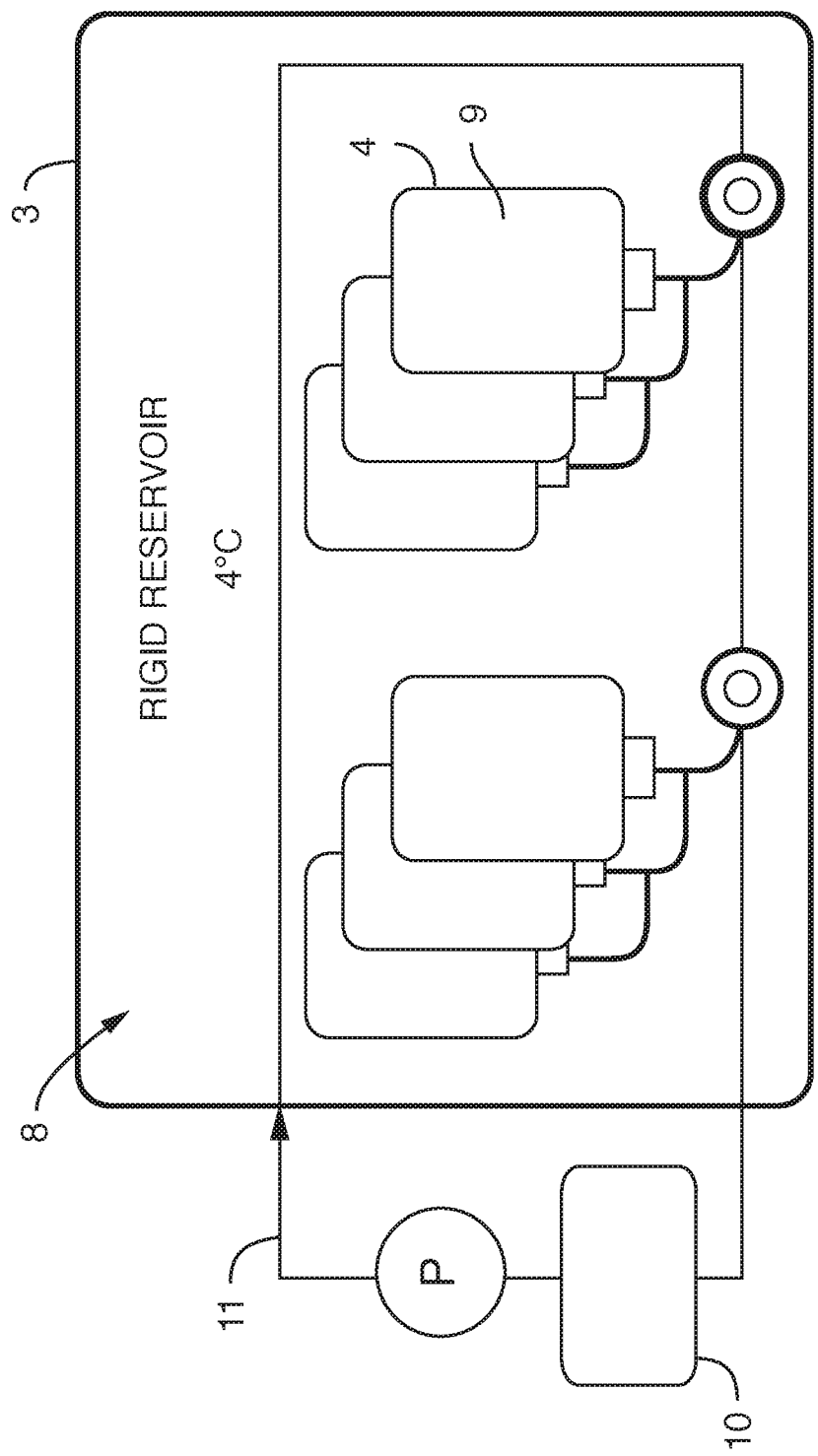
FIG. 5 is a schematic showing one embodiment of a cooling system using a cooling fluid that is independent from the other fluids (e.g. independent from the working fluid or liquid in the flexible reservoirs). There is no mixing between fluids in this assembly. Cooling fluid from a cooling fluid reservoir flows through a conduit (e.g. stainless-steel tubing—which is a good heat exchanger). The conduit can be outside or inside the rigid container (or both).
Figure 6:
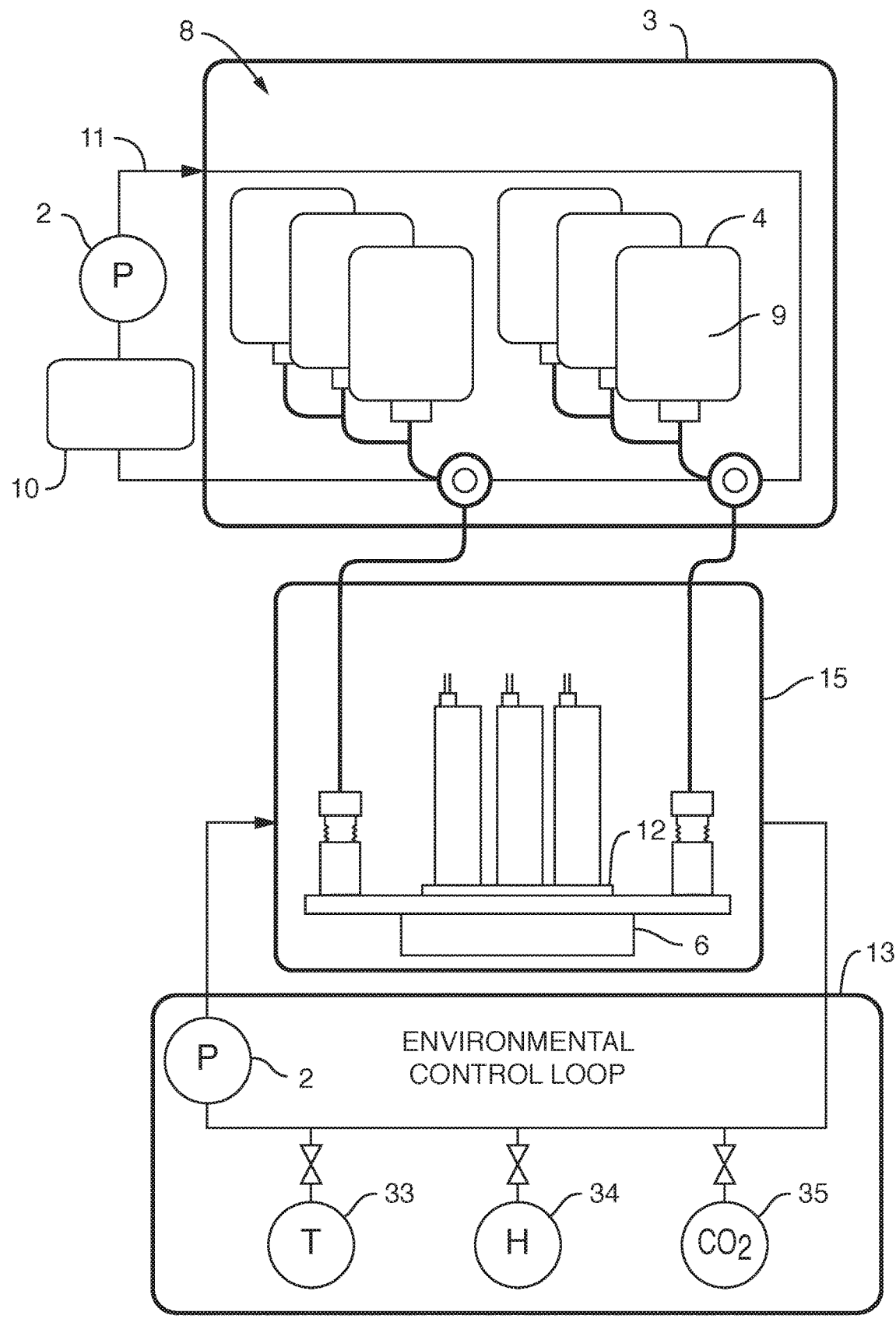
FIG. 6 is a schematic showing one embodiment of the system architecture for one embodiment of an assembly. In this case, the assembly with the cooling system shown in FIG. 5 is depicted in fluidic communication with a manifold and manifold enclosure (or incubator box), the manifold comprising one or more microfluidic devices or "chips" associated with fluid connectors and valves. The manifold enclosure functions as an incubator when governed by an environmental control loop, which controls temperature (T), humidity (H), and carbon dioxide levels ($CO_2$).

FIG. 6 is a schematic showing one embodiment of the system architecture for one embodiment of an assembly. In this case, the assembly with the cooling system shown in FIG. 5 is depicted in fluidic communication with a manifold and manifold enclosure (or incubator box), the manifold comprising one or more microfluidic devices or "chips" associated with fluid connectors and valves. The manifold enclosure functions as an incubator when governed by an environmental control loop (13), which controls temperature (T) (33), humidity (H) (34), and carbon dioxide levels ($CO_2$) (35).

The thermoelectric cooling system generates a significant amount of heat due to inefficiencies, and as such increases the need for an insulated container in which the media is to be stored. Without insulation the heating and cooling systems would require a significant amount of energy in order to maintain desired temperature gradients across the entire system. A mathematical representation of the thermal environment was built in order to quantify the temperature gradients across the system. FIG. 32 summarizes the mathematical calculations used in the temperature gradient representation.

In yet another embodiment, the present invention contemplates an assembly where there are two or more internal reservoirs (4) in a single container (3), but where different liquid (9) is in at least one reservoir (i.e. different from at least one other reservoir). For example, in one embodiment (FIG. 9), the present invention contemplates an assembly, comprising one or more flexible cell culture media reservoirs (4) and one or more flexible reagent reservoirs (18) contained within a container (3), said container i) in fluidic communication with a pump (2) and a working fluid reservoir (1) and ii) comprising a working fluid (8), said flexible cell culture reservoirs i) in fluidic communication with one or more fluidic devices (including but not limited to) microfluidic devices (6) and ii) comprising cell culture media (preferably degassed media), said one or more flexible reagent reservoirs (18) in fluidic communication with said one or more fluidic devices (including but not limited to microfluidic devices) and comprising reagent, wherein there is no mixing of said working fluid with said cell culture media. In one embodiment, said container (3) is sealed such that said working fluid can only enter or exit the container through conduits. In one embodiment, the working fluid (8) surrounds at least one internal reservoir (4). In one embodiment, said one or more fluidic devices are outside said container (3). In one embodiment, said one or more fluidic devices are microfluidic devices (6) housed in a manifold (12). In one embodiment, the manifold is configured to heat liquid prior to the liquid entering one or more microfluidic devices (one example of "just in time" heating). In one embodiment, said liquid is heated after it is displaced and while it begins flowing into said one or more fluidic devices (another example of "just in time" heating). In one embodiment, the manifold (12) is temperature controlled. In one embodiment (FIG. 8B), the manifold is temperature controlled by enclosing the manifold (12) in an enclosure or incubator box (15), allowing for the microfluidic devices to be exposed to temperatures consistent with cell growth and viability, such as 37° C.+/−2 degrees, as well as proper humidity and $CO_2$ levels). In one embodiment, the incubator box (15) or the manifold (12) comprises a temperature sensor. In one embodiment, said one or more microfluidic devices comprise living cells on a surface (FIG. 28). In one embodiment, said surface is a microfluidic channel (e.g. channel wherein one or more dimensions are 1 mm or smaller, and more typically 0.1 mm or smaller) or portion thereof. In one embodiment, said surface is a membrane. In one embodiment, the microfluidic device comprises inlet and outlet ports, said inlet and outlet ports in fluidic communication with said one or more microfluidic channels. In one embodiment, said microfluidic channels comprise cells. In one embodiment, said cells are on a membrane. In one embodiment (FIGS. 9 and 10), each microfluidic device (6) is in fluidic communication with a sampling conduit (21) and a waste reservoir (20). In one embodiment, said reagent in said reagent reservoir (18) is selected from the group consisting of a lysate reagent, a fixative reagent and a staining reagent. In one embodiment (FIG. 7), the assembly further comprises a flow rate sensor configured to detect the flow rate of culture fluid. In one embodiment, the assembly further comprises a pressure sensor configured to detect clogging and or blocking of flow of the culture fluid.

Figure 10A:
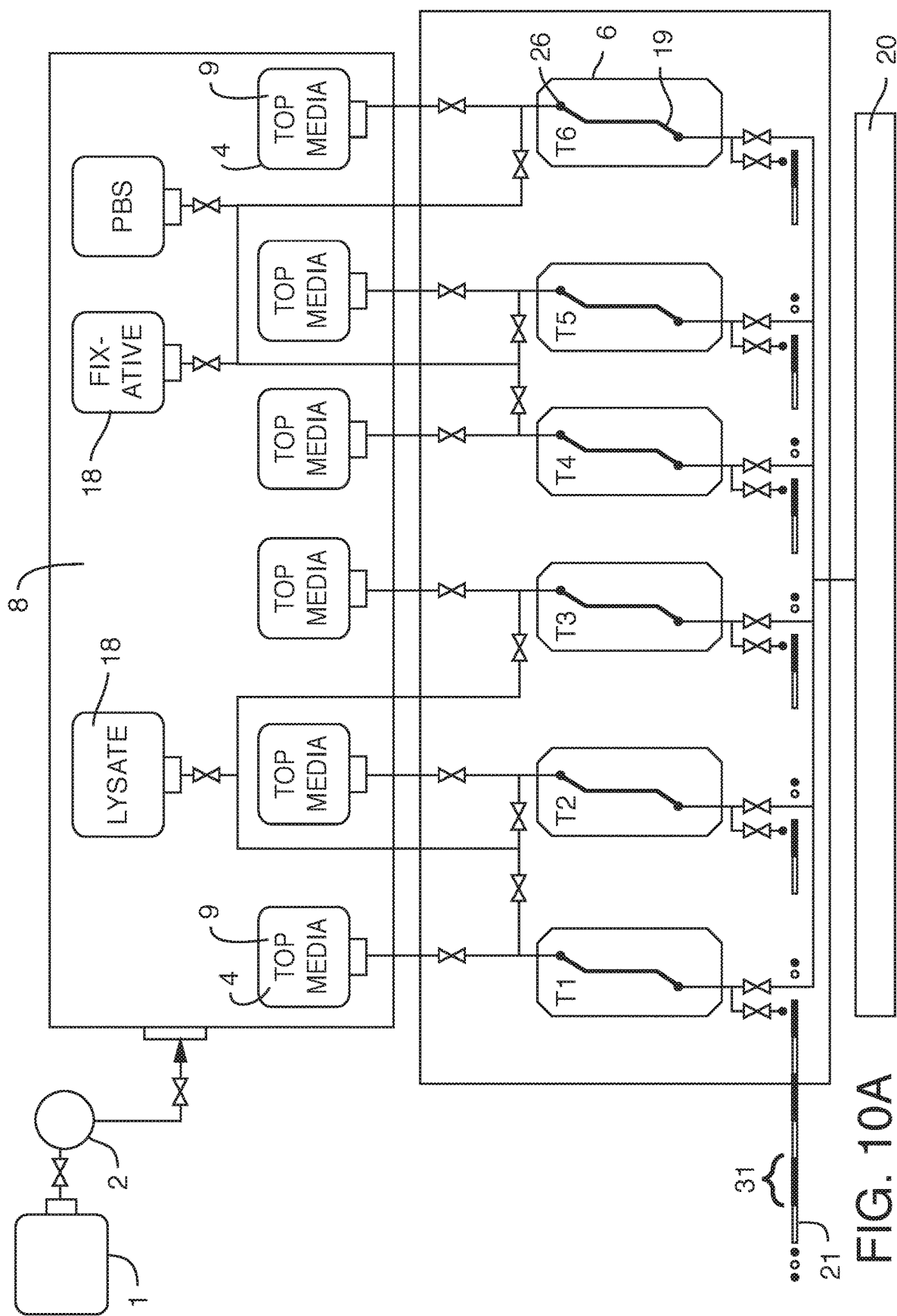
FIGS. 10A and 10B are schematics showing how the six microfluidic devices on a manifold (depicted in FIG. 8A) might be valved, the microfluidic devices (or chips) comprising inlet and outlet ports in fluidic communication with one or more microfluidic channels (in this case, a two-channel microfluidic device, i.e. a device with a top channel and a bottom channel).
Figure 10B:
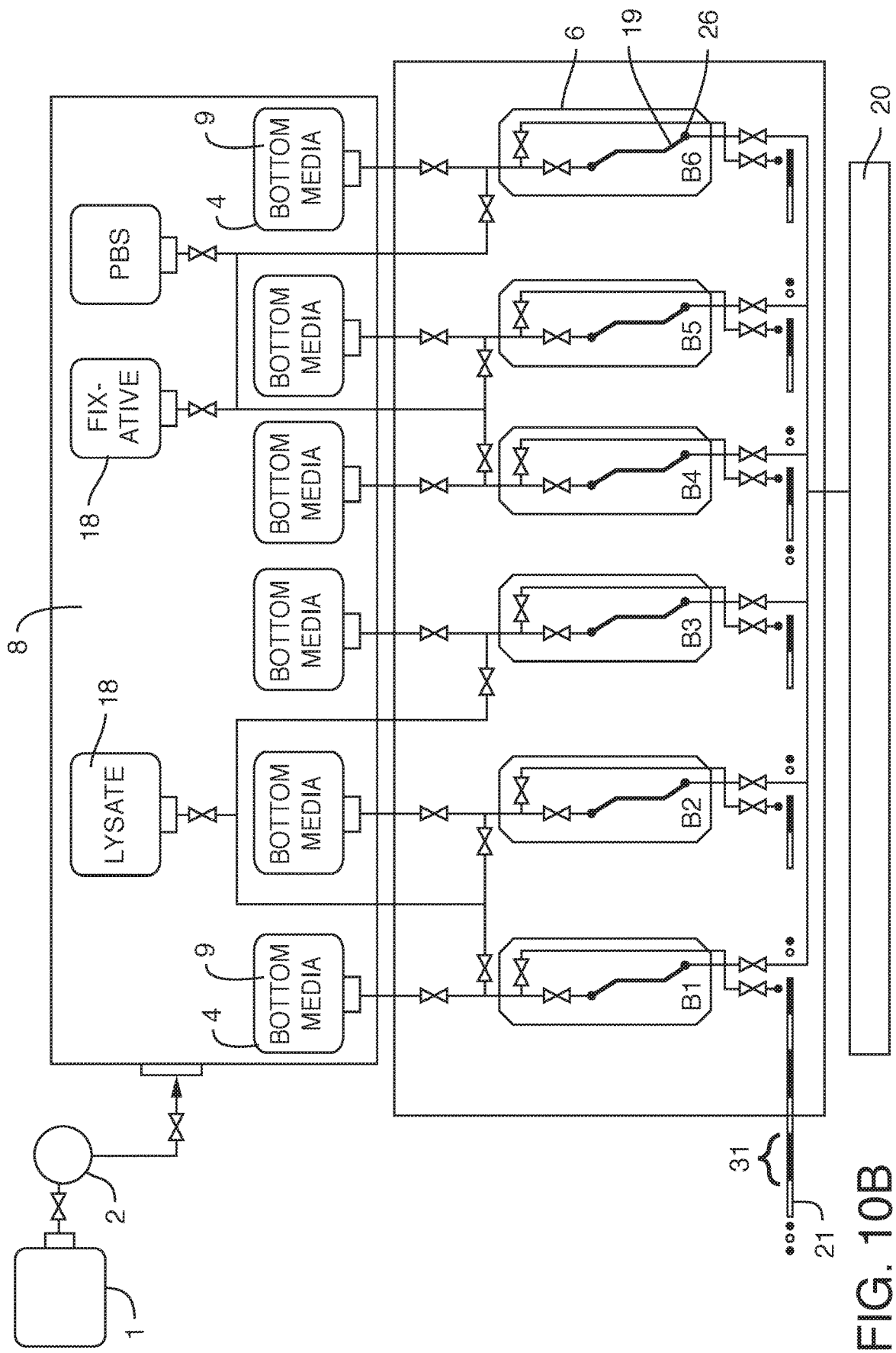
Figure 11:
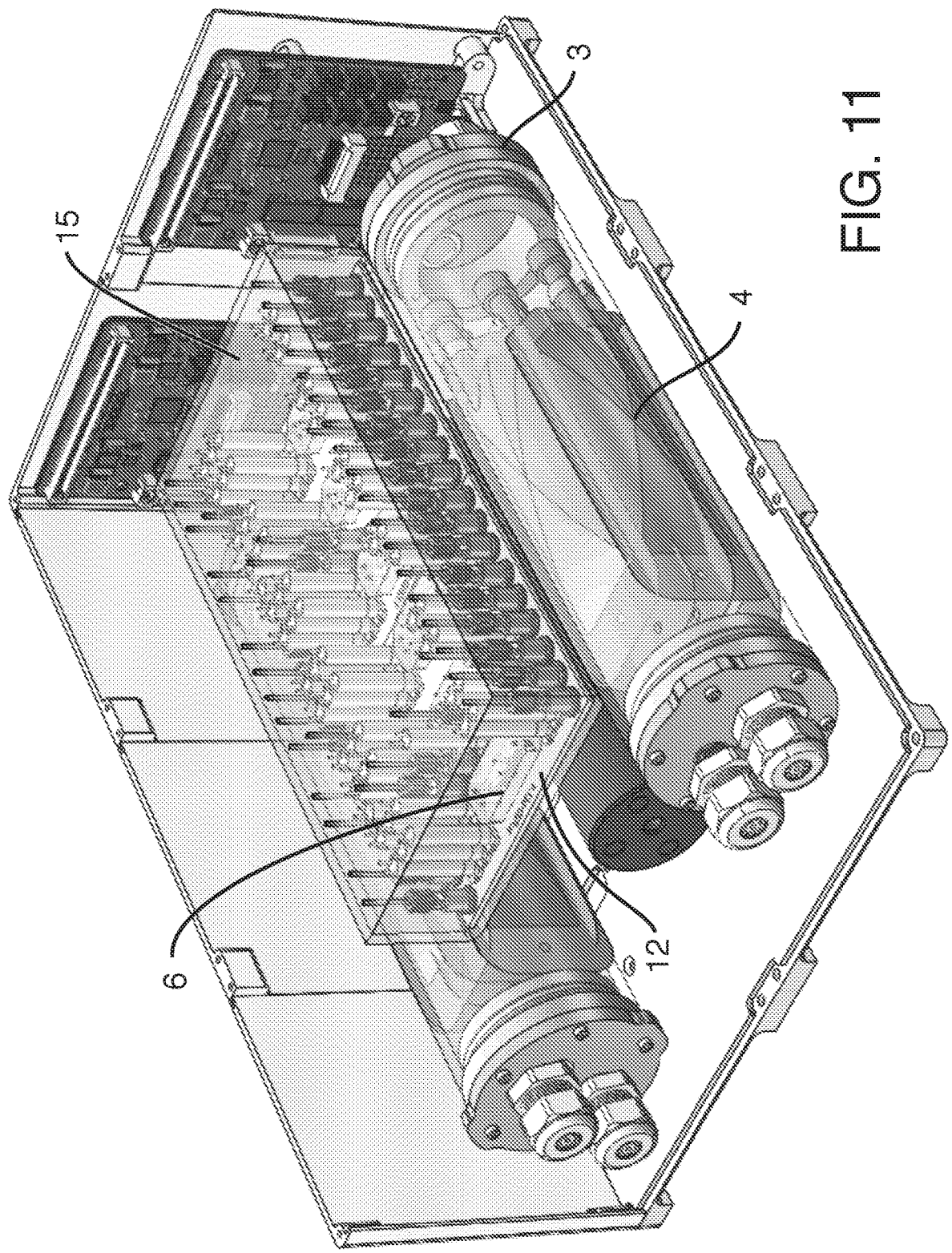
FIG. 11 is a top side view schematic of one embodiment of an assembly comprising flexible reservoirs within two rigid containers, the flexible reservoirs in fluidic communication with six microfluidic devices or chips on a manifold, the manifold enclosed by an incubator box.

FIGS. 10A and 10B are schematics showing how, in one embodiment, the six microfluidic devices on a manifold (depicted in FIG. 8A) might be valved, the microfluidic devices (or chips) comprising inlet and outlet ports in fluidic communication with one or more microfluidic channels (in this case, a two-channel microfluidic device, i.e. a device with a top channel and a bottom channel). FIG. 10A is a schematic separating out the fluidics for the top microfluidic channel (or T) in an embodiment of an assembly comprising both reagent reservoirs (a lysate reservoir and a fixative reservoir are shown as examples of reagent reservoirs) and media reservoirs housed within the rigid container, with valves (depicted as unshaded opposing arrows "><") shown for controlling what fluid enters the chips, as well as the valves shown for controlling what fluid enters the sampling conduit and what fluid enters the waste reservoir. FIG. 10B is a schematic separating out the fluidics for the bottom microfluidic channel (or B) in an embodiment comprising both reagent reservoirs (a lysate reservoir and a fixative reservoir are shown as examples of reagent reservoirs) and media reservoirs housed within the rigid container, with valves (depicted as unshaded opposing arrows "><") shown for controlling what fluid enters the chips, as well as the valves shown for controlling what fluid enters the sampling conduit and what fluid enters the waste reservoir.

In operation, a working fluid (liquid or air) can then be pumped into the rigid container, causing displacement of the media in the flexible reservoirs into the downstream fluidics. Without limiting the invention in any manner to any particular mechanism, it is believed that the working fluid pumped into the "hard" reservoir puts pressure on flow fluid in "soft" reservoir. In one embodiment, the working fluid can be pumped into the rigid container using a displacement pump, an arrangement that allows for the flow rate of the working fluid to match the flow rate of the media, even if an occlusion changes the fluidic resistance downstream of the reservoirs. Positive displacement pumps have an expanding cavity on the suction side and a decreasing cavity on the discharge side. Liquid flows into the pumps as the cavity on the suction side expands and the liquid flows out of the discharge as the cavity collapses.

Multiple reservoirs can be used. Moreover, they need not be flexible; they can also be rigid reservoirs such as a syringe with a movable piston or surface. In any event, multiple reservoirs can be incorporated into a single container (preferably rigid container), and their flow rates can be set by a single pump moving the working fluid. This allows you to pump as many individual fluid reservoirs using a single pump. Resistance in the downstream fluidics allows one to get the individual reservoirs bags to flow at the same flow rate.

Figure 18:
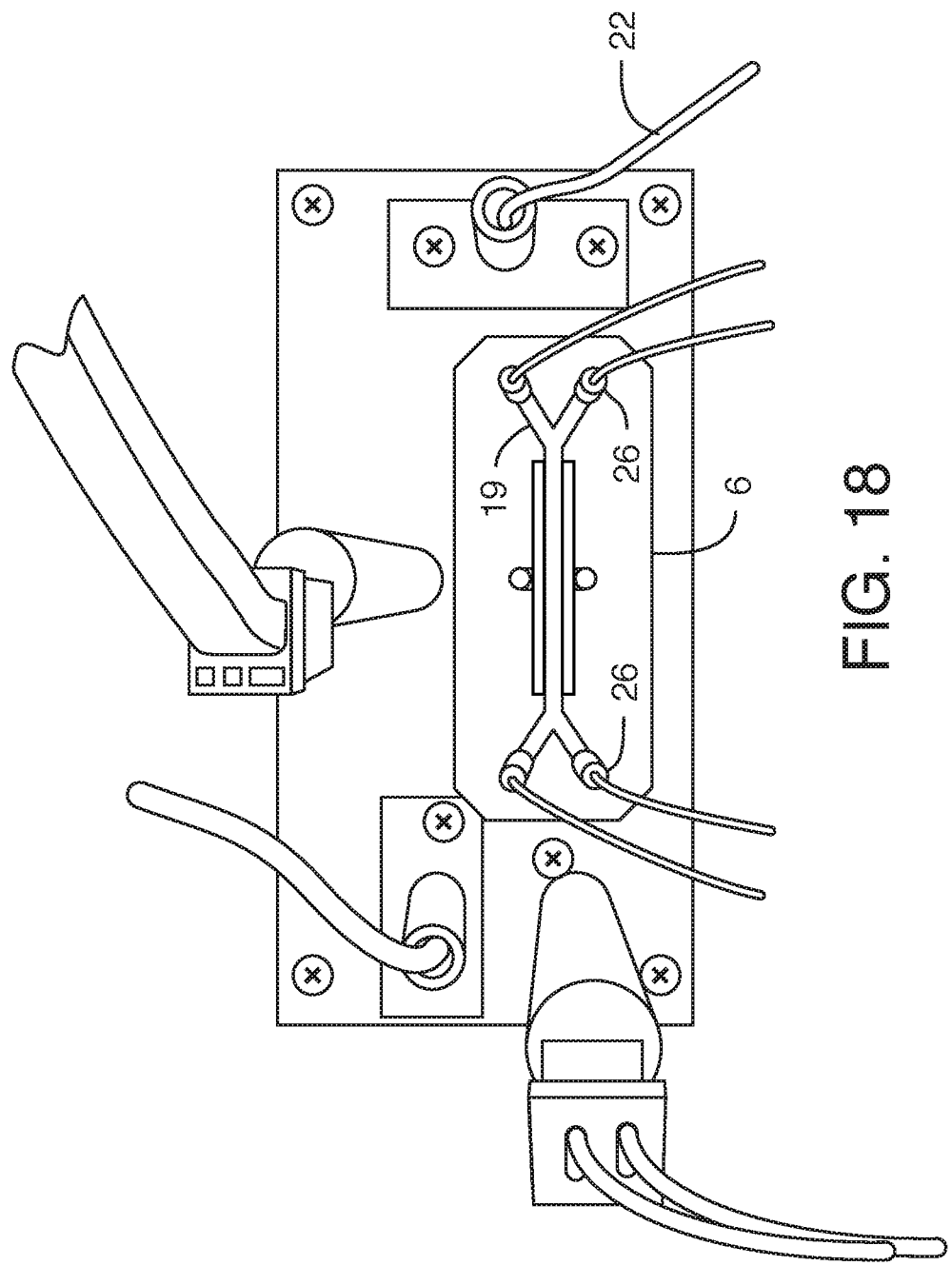
FIG. 18 shows one embodiment of a manifold engaging a microfluidic device for purposes of testing the ability to recirculate media through a recirculation pathway on the manifold.

The working fluid does not mix (indeed, it is preferred there is no contact) with the cell culture media, making selection of pumps and flow sensors (27) easier. Fluid can be pressurized for applications such as reducing bubble size without increasing the gas concentration of the media.
Multiple media and reagent bags with valves can be incorporated into the same rigid container. The working fluid pump can always be operating, while the media/reagent being actively pumped can be controlled by the valves. This means one can control the flow of multiple fluid inputs to a device using a single pump. Additionally, one can have multiple rigid containers being fed by a single working fluid pump and a series of valves controlling the relative flow rates of incoming working fluids.

Where recirculation is desired, a given volume of culture media (e.g. all of it, a portion of it, etc.) is recirculated, whereas in non-recirculating perfusion, the culture media is perfused through the system and sent to directly to waste. Secreted factors and waste products in recirculating cultures are diluted into the total culture media volume (although this can be avoided by the use of a second reservoir, and the second reservoir can be avoided by using tubing). FIG. 18 shows one embodiment of a manifold engaging a microfluidic device for purposes of testing the ability to recirculate media through a recirculation pathway on the manifold.

Figure 7:
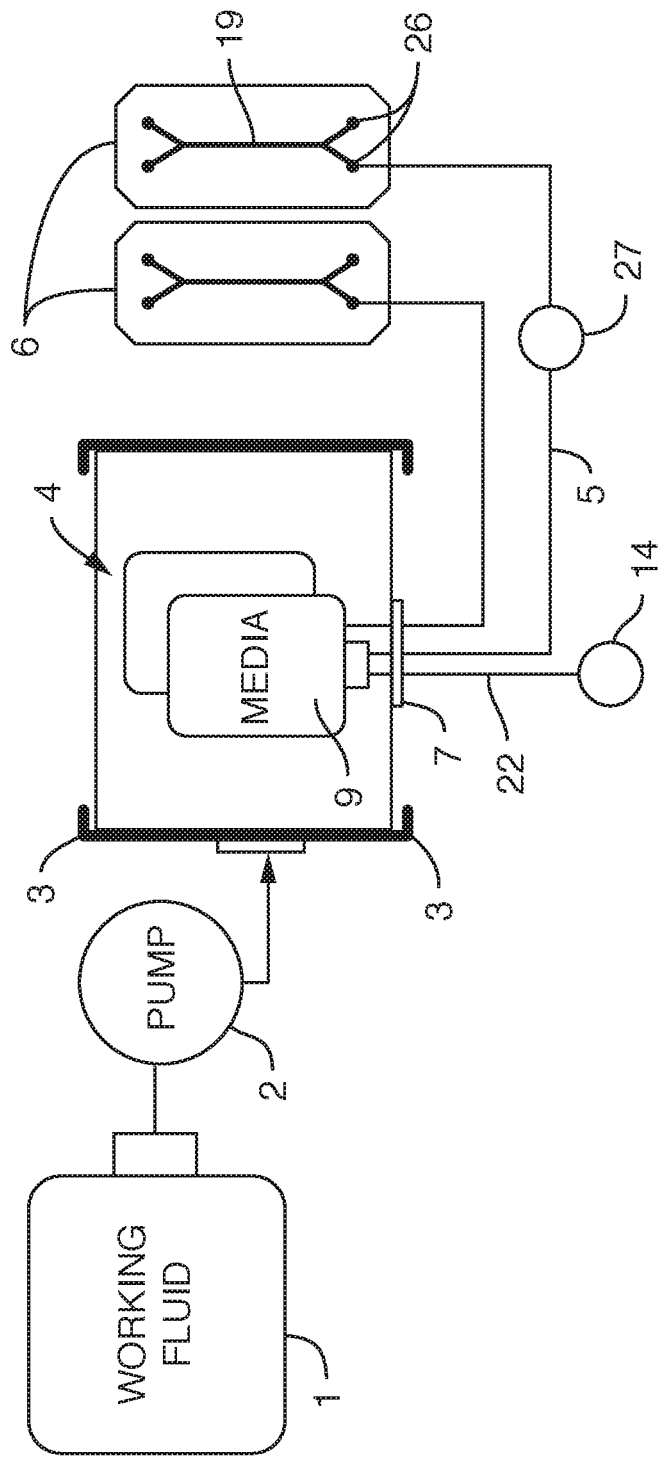
FIG. 7 is a schematic showing one embodiment of a rigid container housing a flexible reservoir or bag, with the tubing passed through a grommet (or multi-hole strain relief fitting), some tubing connected to a flow rate sensor and/or pressure gauge.
Figure 31:
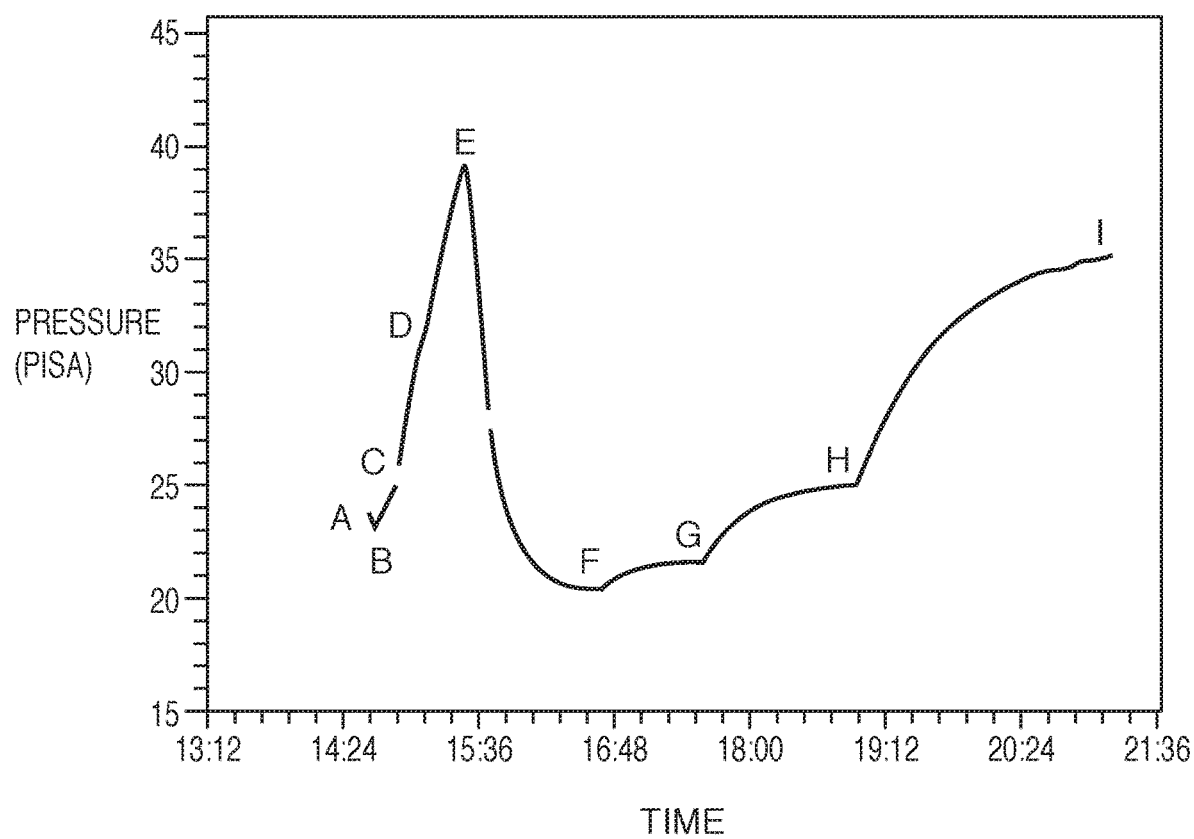
FIG. 31 depicts the rigid container pressure as different media reservoir outlet channels are closed in order to demonstrate an ability to sense occlusions in the channels. The path from A to E shows pressure building in the rigid reservoir with all media reservoirs outlets closed. At E, the media valves are opened and media flows, relieving pressure until it almost reaches equilibrium at point F. At point F one of the media channels is closed to simulate a blockage (i.e. from a bubble), and a rise in pressure between F and G is seen. At point G another channel is closed and another pressure rise can be seen between points G and H. Finally, the final media channel is closed at point H, and it can be seen that there is a pressure rise between points H and I. The change in pressure increase, or delta, is an indication of how many channels are occluded.

It is important to have feedback on fluid flow to know if an occlusion (bubble, particle, etc.) has stopped or slowed the flow. These occlusions may be sensed and corrected for by flushing the occlusion out with a higher flow rate. In one embodiment, a flow sensor (27) is integrated into the flow lines. However, the choice of flow sensor (27) depends on the desired properties. For example, one can have a sensor that is biocompatible, inexpensive, disposable, as well as has a low dead-volume, easy electrical connections, etc. As an alternative to an integrated flow sensor (27), one embodiment, as depicted in FIG. 7, is an integrated pressure sensor (14) into the rigid container (3). The pressure sensor could monitor the pumping pressure of the working fluid and be able to sense if an occlusion has occurred. At steady state, the working fluid pump (2) infuses working fluid at a constant flow rate. The pumping of working fluid generates a pressure in the rigid reservoir (3) that is also constant at steady state. However, if there is a blockage in any of the fluid channels then the pressure within the container will increase as seen in FIG. 31. If additional channels are occluded, the pressure in the container will continue to increase in a step-wise fashion. An increase in pressure, as read by a pressure sensor (14), may be solved by closing all media channels but one and flushing media through at a high flow rate. The process may be repeated for each individual channel until the higher pressure abates.

FIG. 31 shows the rigid container (3) pressure as different media reservoir outlet channels are closed in order to demonstrate an ability to sense occlusions in the channels. The path from A to E shows pressure building in the rigid reservoir with all media reservoirs outlets closed. At E, the media valves are opened and media flows, relieving pressure until it almost reaches equilibrium at point F. At point F one of the media channels is closed to simulate a blockage (i.e. from a bubble), and a rise in pressure between F and G is seen. At point G another channel is closed and another pressure rise can be seen between points G and H. Finally, the final media channel is closed at point H, and it can be seen that there is a pressure rise between points H and I. The change in pressure increase, or delta, is an indication of how many channels are occluded.

The media flush to clear blockages may be done automatically, or the pressure signal rise may trigger an alarm to the user, who may then decide whether or not to initiate a flushing sequence. In a preferred embodiment capillary tubing (22) may be routed from inside the rigid container to the outside of the container where it is then attached to a gauge pressure sensor (14). In one embodiment the capillary tubing (22) is routed through a commercial off-the-shelf, leak-proof, strain-relief part.

B. Sampling Effluent

Figure 12:
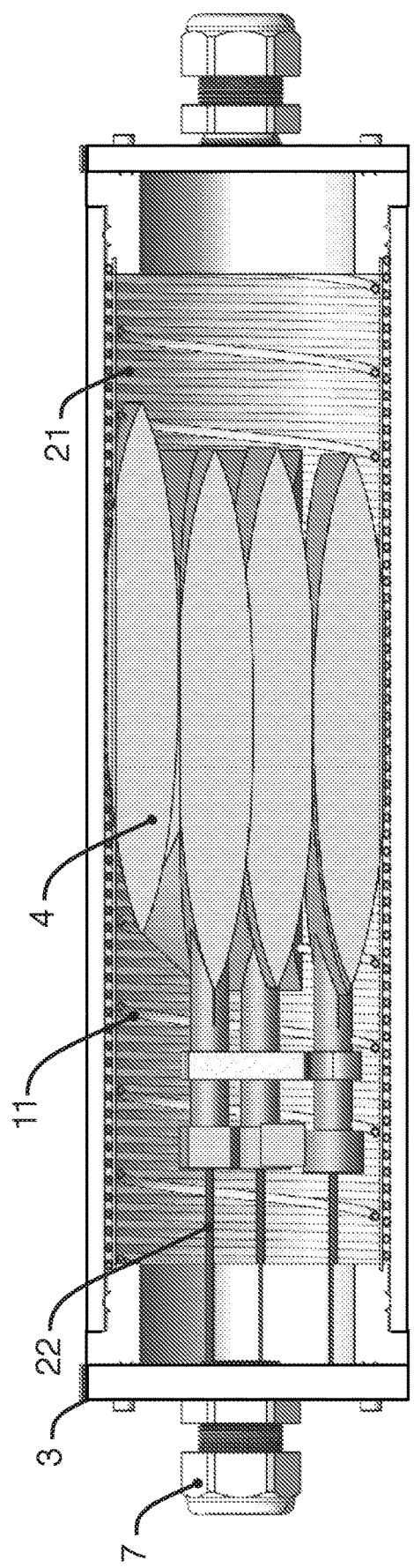
FIG. 12 is a side view schematic of a plurality of flexible reservoirs within one of the rigid containers shown in FIG. 11. Each flexible reservoir is in fluidic communication with capillary tubing which passes through the grommet. The rigid container is associated with cooling tubing.
Figure 15A:
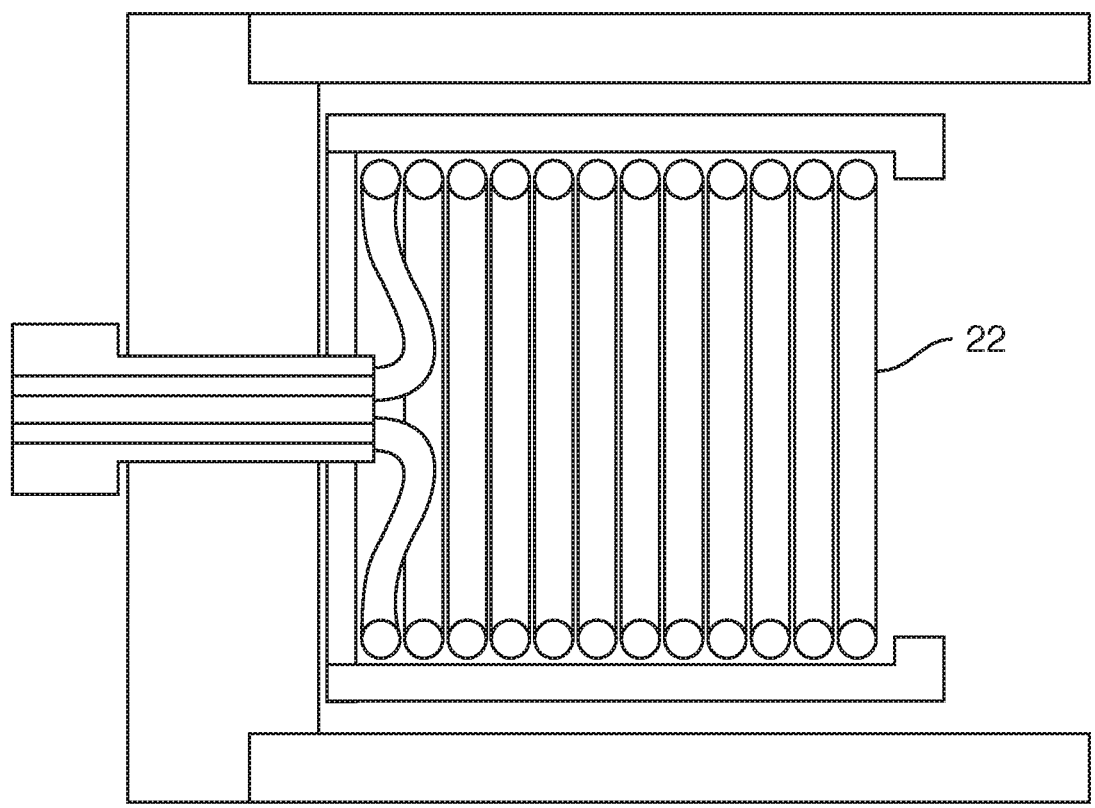
FIGS. 15A and 15B show different concepts for handling tubing in the various assembly embodiments discussed herein, including but not limited to the tubing shown in FIG. 12.
Figure 15B:
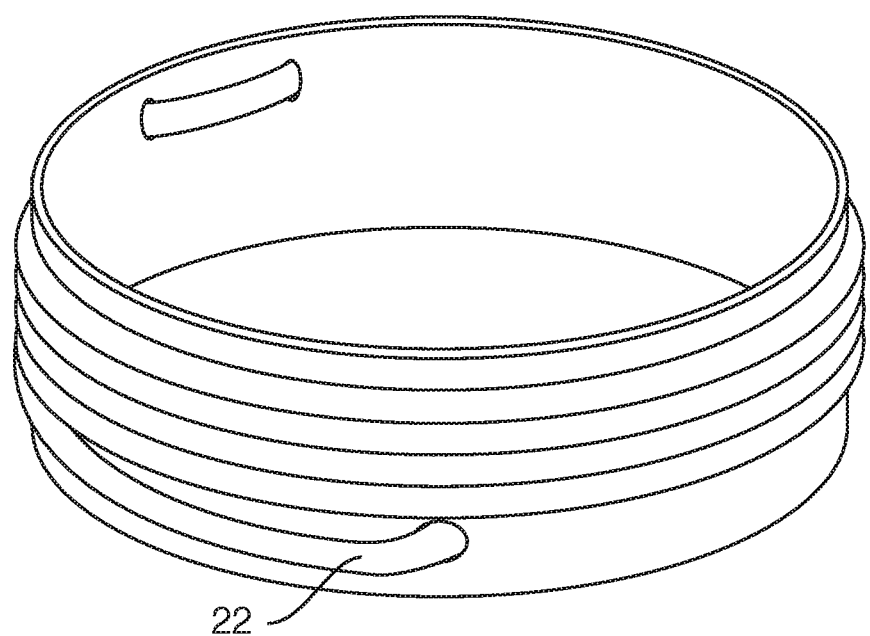

The invention further relates to sampling. In one embodiment, samples are obtained from effluent, i.e. sampling the fluid exiting a microfluidic device as described herein. Thus, the microfluidic devices are in fluidic communication with a sampling conduit for collecting (or removing) samples of effluent fluids, where effluent fluids may or may not include detached cells, secreted proteins and the like. In one embodiment, the microfluidic device comprises a top channel and bottom channel separated by a membrane. In some embodiments, effluent may be collected from media leaving the top channel. In some embodiments, effluent may be collected from media leaving the bottom channel. In some embodiments, effluent sampling is by hand. In some embodiments, the invention comprises an effluent sampling system. In one embodiment, the material exiting each microchannel outlet can be sent to one of three places: 1) the waste reservoir, 2) the recirculation pathway, or 3) the sampling conduit (which is, in a preferred embodiment, microbore capillary tubing ubiquitous in mass spectrometers due to their low compound absorption/adsorption and their low dead-volume). When the sample valve is switched "on" effluent from the chip (9) flows into the sample conduit until the desired volume is collected. The sample volume is driven by the pump flow rate, and the required volume for a given time point (driven by assays) sets the time needed for sample collection. After the appropriate volume of sample (9) has been collected, the sample valve is switched off and gas (or immiscible fluid) (30) is injected into the sampling conduit to ensure each sample is discrete in time and does not diffuse into samples from other time points. The sampling methodology will allow for high-temporal sampling resolution, without the size and added complexity of hundreds of sample reservoirs or bulky switching valves. It also allows for the sample reservoir/tubing to be routed to a separate thermal compartment in an adjacent CubeLab that will allow for storage of the effluent at 4° C. See, FIGS. 9A and B, FIGS. 10A and B, and FIG. 23 for illustrations of various embodiment showing sampling conduits in fluidic communication with microfluidic devices for sample collections (and testing). In one embodiment the sample handling tubing (22) in various assembly embodiments discussed herein, including but not limited to the tubing shown in FIG. 12, is wound using various techniques including those in FIG. 15A and FIG. 15B. FIG. 15A demonstrates one embodiment of tubing (22) wound in an outer basket. FIG. 15B shows an inner drum embodiment, where the tubing (22) is wrapped around the drum.

Samples, including effluent cell culture media from experiments (9), may be collected over time, for example, different time-points separated by seconds, up to minutes, up to hours, up to days apart depending upon the desired readout for an experiment. Samples may be labeled in part as sample 1, sample 2, etc., see FIGS. 24-26. One embodiment for separating sequential sample collection is to induce an air plug (30) in between the desired sample amounts (31). Sample amounts (31) may be in nanoliters, ul up to ml in amounts. One embodiment, the sampling is based on the ice core approach. For example, in one embodiment, sampling is continuous sampling (i.e. no gaps (30) to reduce or eliminate mixing between samples (31)). For microfluidics mixing is limited by laminar flow, and only diffusive mixing occurs. In one embodiment, sampling is discontinuous (use gaps (30) to avoid mixing). In one embodiment, a T-junction is used to introduce a gas (but could also be used to introduce other immiscible fluids).

In one embodiment, samples enter said sampling conduit in zero gravity or microgravity conditions.

In one embodiment, said samples are stored in said sampling conduit (e.g. in a manner similar to how ice cores are stored, i.e. with the different chronological samples stored together in one continuous conduit). In one embodiment, the sampling conduit is cooled by the working fluid. In one embodiment, the sampling conduit is stored cold in the rigid container. In one embodiment, the stored samples are later tested, e.g. the samples are either removed from (e.g. pushed out of) the sampling conduit or tested within the sampling conduit. In one embodiment a filter (28) is at the end of the capillary tubing (22) in which the samples are stored in order to maintain sterility.

C. Readouts on Effluent Sampling.

It is not intended that the present invention be limited by the nature of the testing done on samples. Exemplary readouts on effluent sampling can include but are not limited to: DNA analysis, RNA analysis; immunohistochemistry; detection of cytokine signals, etc. In one embodiment, the analysis will compare results between hypergravity, microgravity, and terrestrial conditions in addition to response to compounds, such as drugs, for reversing undesirable responses to a change in cell conditions.

D. System Assembly

The system may be assembled in any configuration, such that the overall processes are carried out effectively, and also such that the overall assembly fits in a designated amount of space.

Figure 19:
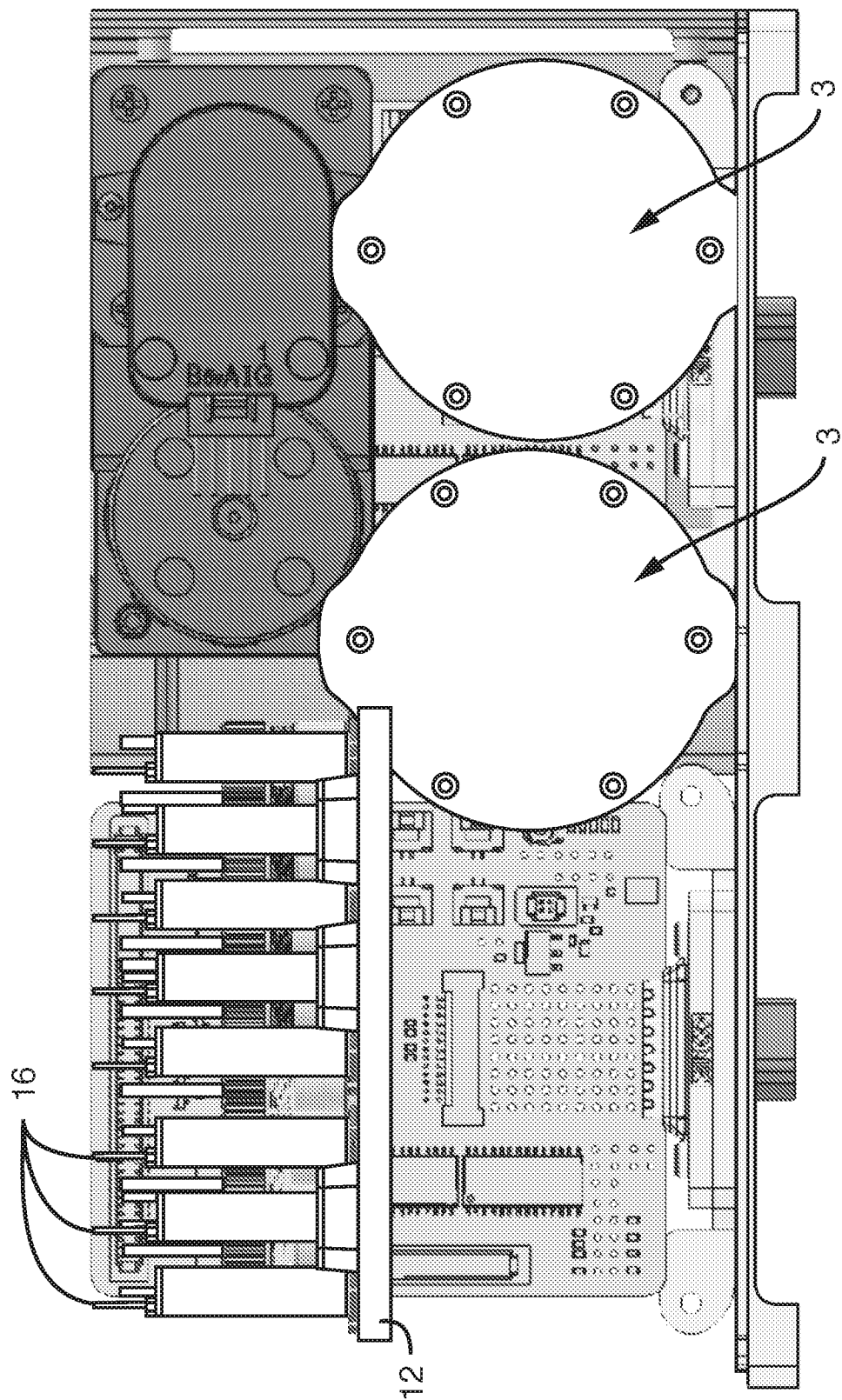
FIG. 19 is a schematic showing one embodiment for arranging one embodiment of an assembly, the assembly comprising two rigid containers and a manifold comprising microfluidic devices and associated fluid connectors, where the containers are below and to the right of the manifold.

FIG. 19 is a schematic showing one embodiment for arranging one embodiment of an assembly, the assembly comprising two rigid containers and a manifold comprising microfluidic devices and associated fluid connectors, where the containers are below and to the right of the manifold.

Figure 20A:
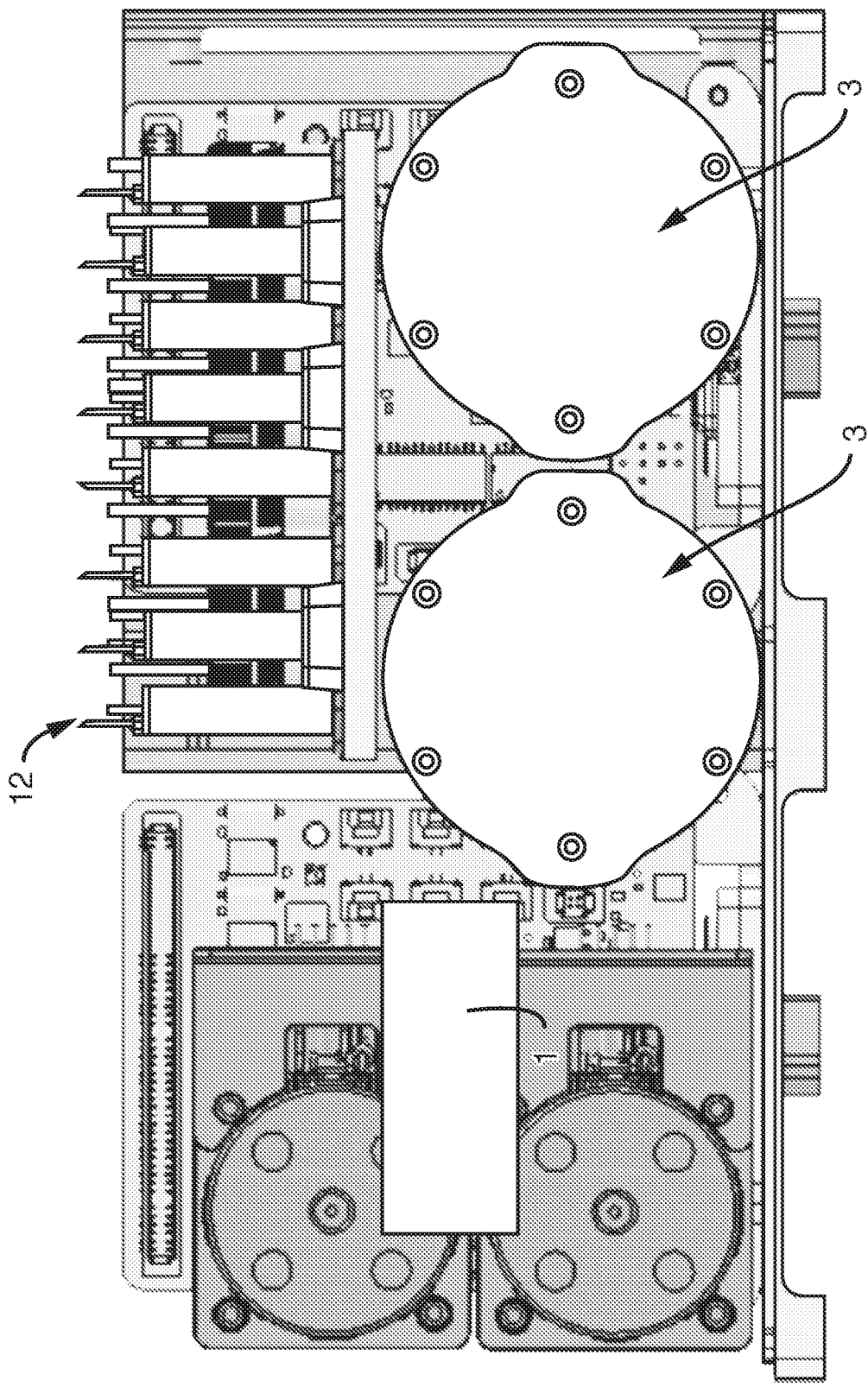
FIGS. 20A and 20B are schematics showing one embodiment for arranging one embodiment of an assembly, the assembly comprising two rigid containers and a manifold comprising microfluidic devices and associated fluid connectors, where the manifold is directly above the two rigid containers.
Figure 20B:
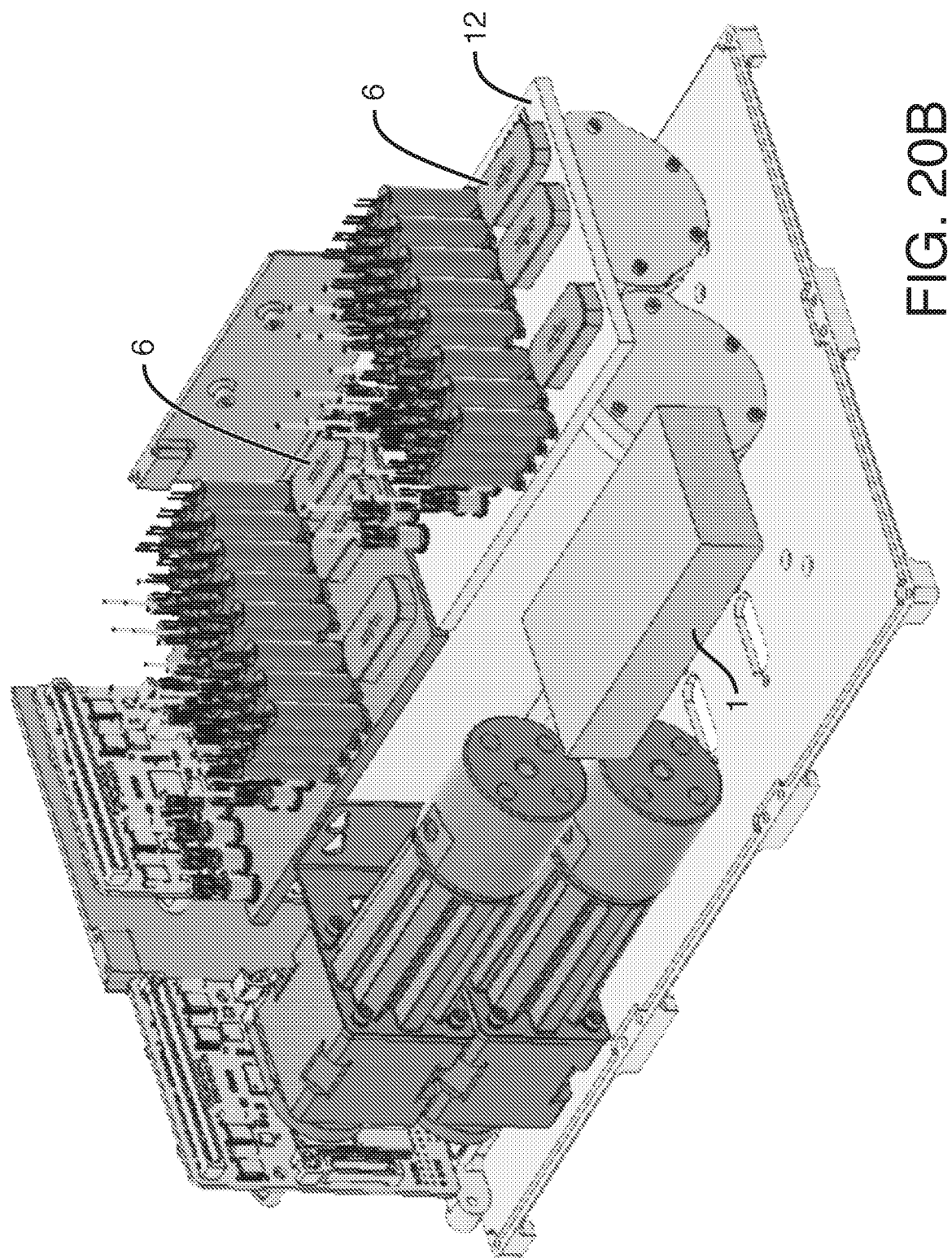

FIGS. 20A and 20B are schematics showing one embodiment for arranging one embodiment of an assembly, the assembly comprising two rigid containers and a manifold comprising microfluidic devices and associated fluid connectors, where the manifold is directly above the two rigid containers. FIG. 20A is a side view and FIG. 20B is a top side view, showing the positioning of the working fluid reservoir.

Figure 21A:
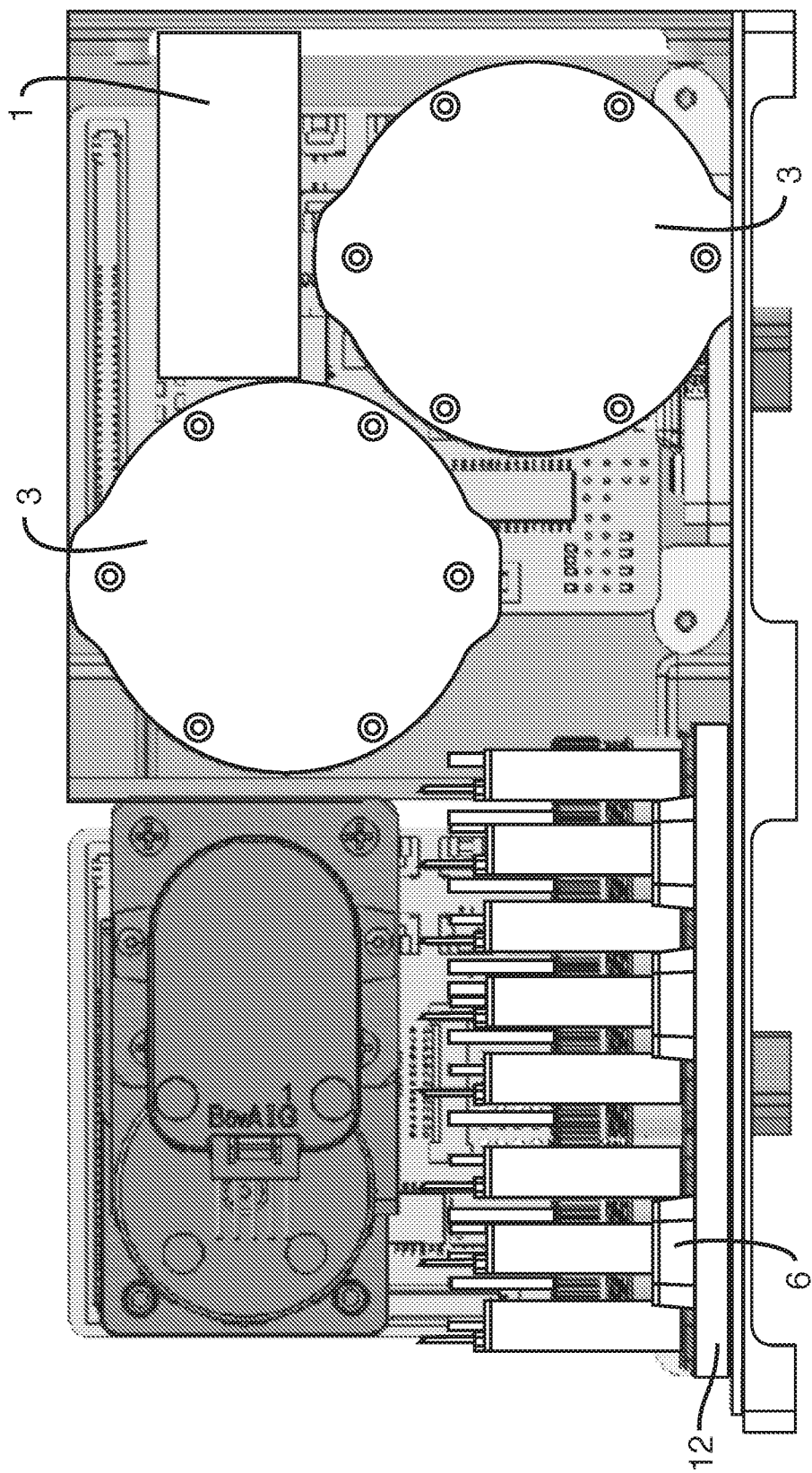
FIGS. 21A and 21B are schematics showing one embodiment for arranging one embodiment of an assembly, the assembly comprising two rigid containers (one slightly above the other and to the side) and a manifold comprising microfluidic devices and associated fluid connectors, where the manifold is on the same level as the lower container, but to the side.
Figure 21B:
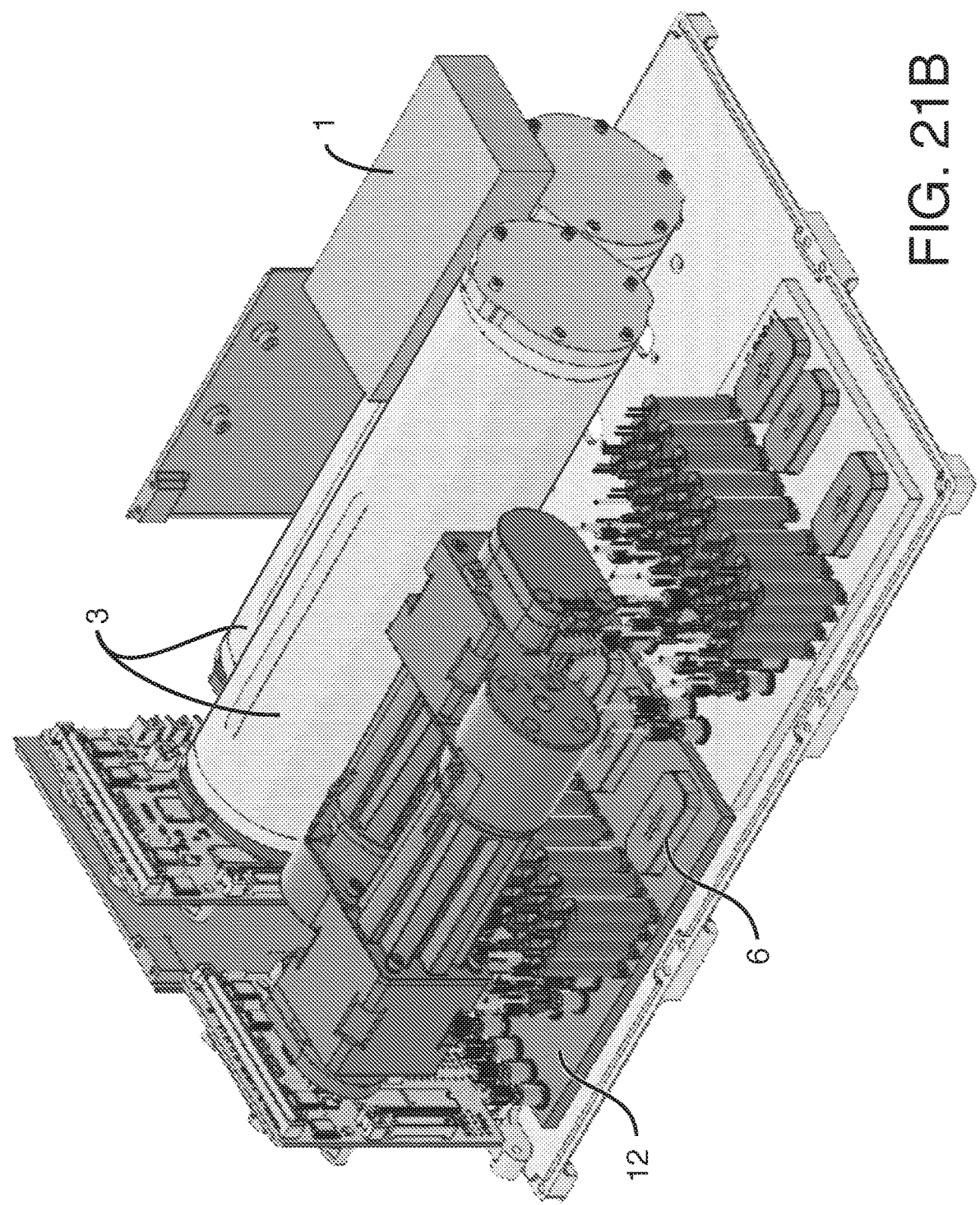

FIGS. 21A and 21B are schematics showing one embodiment for arranging one embodiment of an assembly, the assembly comprising two rigid containers (one slightly above the other and to the side) and a manifold comprising microfluidic devices and associated fluid connectors, where the manifold is on the same level as the lower container, but to the side. FIG. 21A is a side view and FIG. 21B is a top side view, showing the positioning of the working fluid reservoir and the plurality of microfluidic devices or chips positioned on the manifold.

Figure 22A:
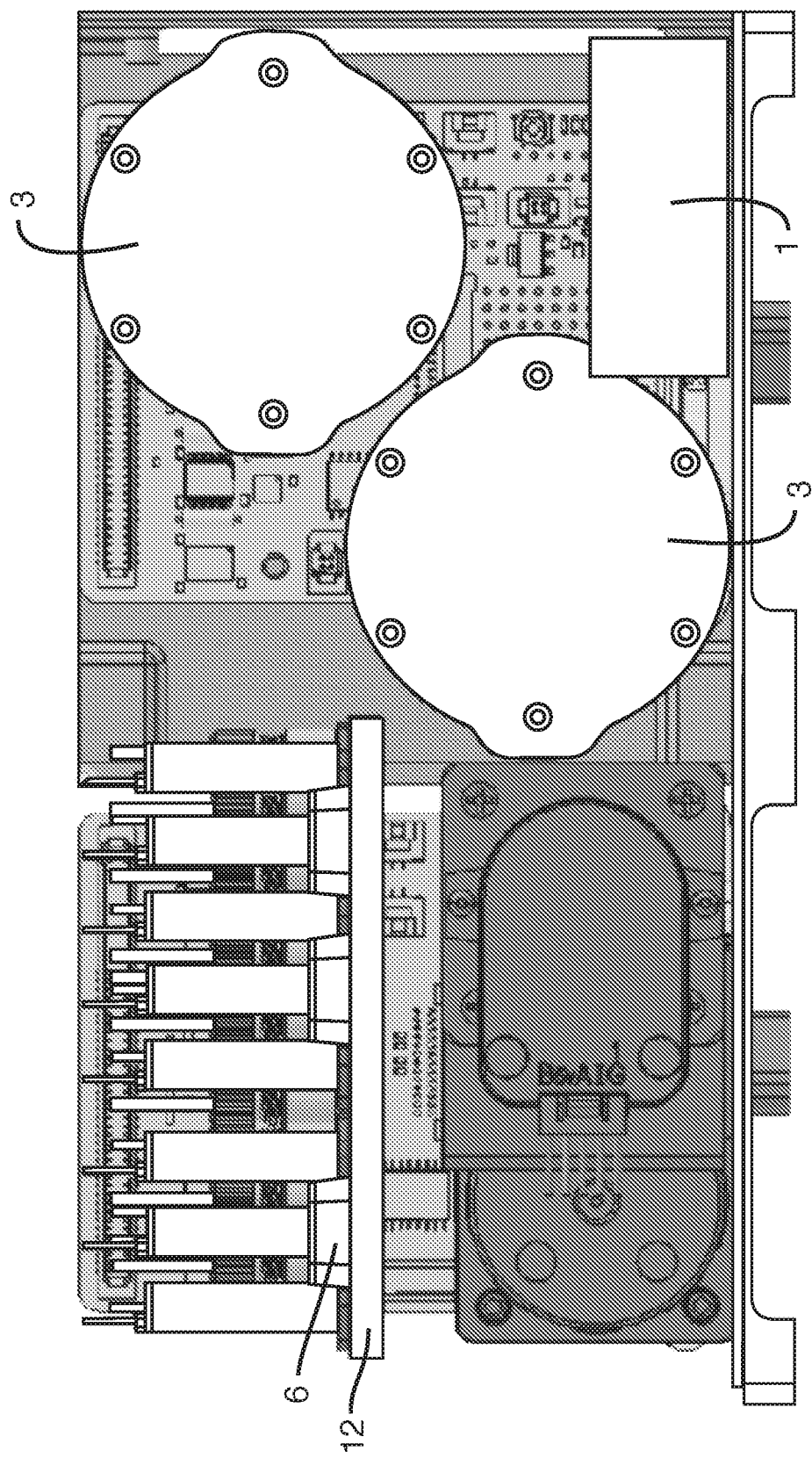
FIGS. 22A and 22B are schematics showing one embodiment for arranging one embodiment of an assembly, the assembly comprising two rigid containers (one slightly above the other and to the side) and a manifold comprising microfluidic devices and associated fluid connectors, where the manifold is on the same level as the upper container, but to the side.
Figure 22B:
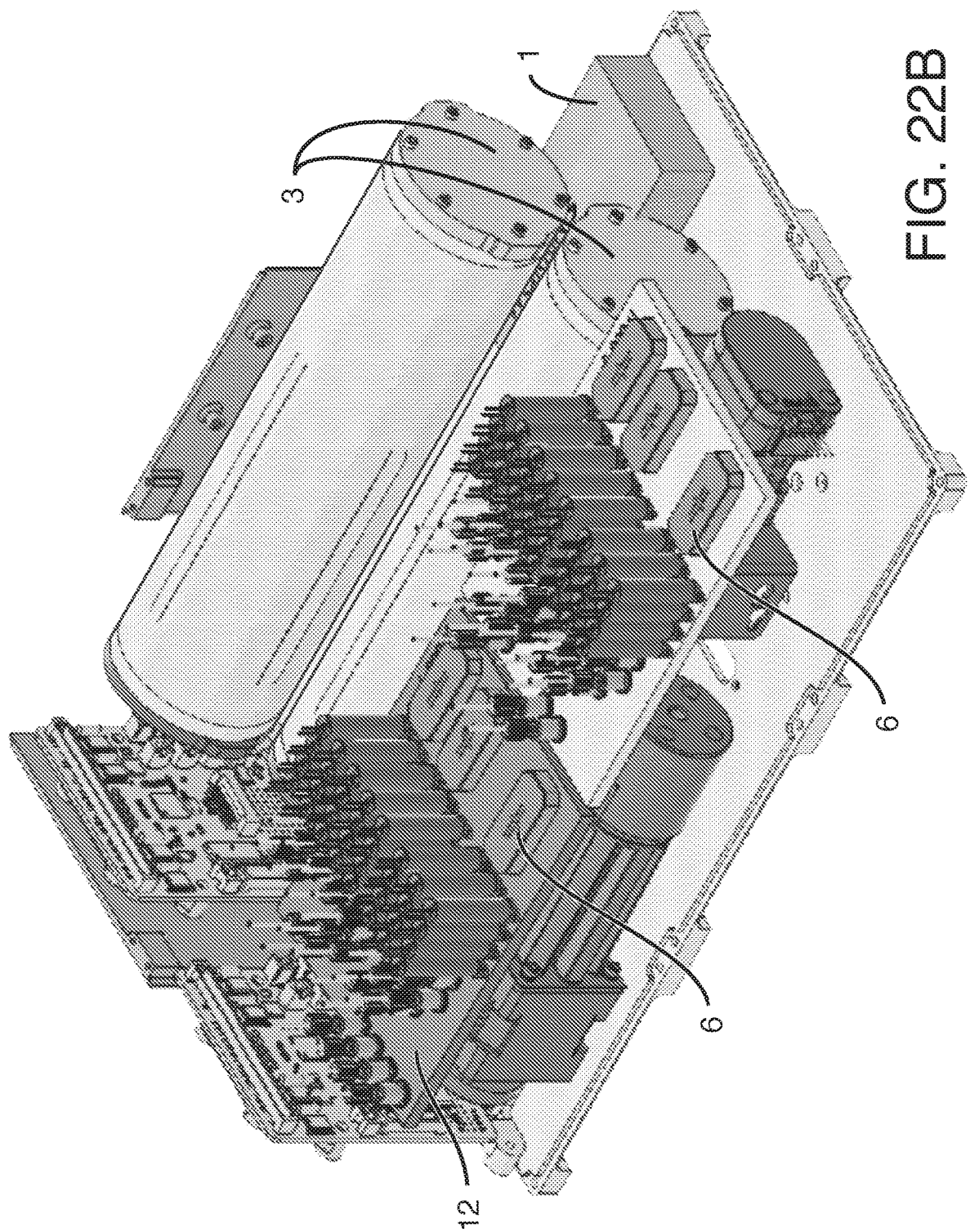
Figure 23:
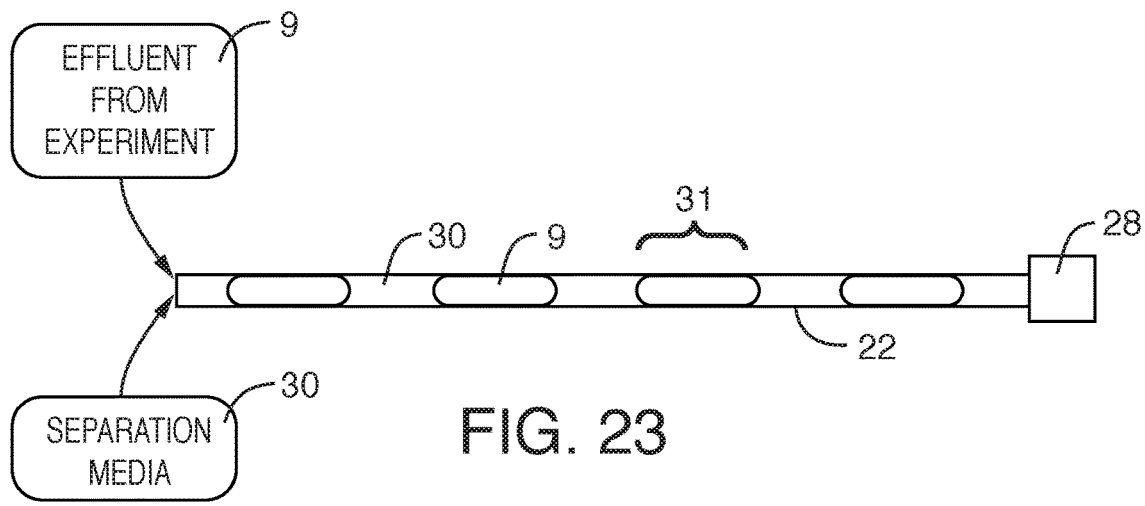
FIG. 23 is a schematic showing one embodiment of a sampling conduit where separation media (gas or liquid) is used to create discrete samples or "plugs." The other components of the assembly are not shown.

FIGS. 22A and 22B are schematics showing one embodiment for arranging one embodiment of an assembly, the assembly comprising two rigid containers (one slightly above the other and to the side) and a manifold comprising microfluidic devices and associated fluid connectors, where the manifold is on the same level as the upper container, but to the side. FIG. 22A is a side view and FIG. 22B is a top side view, showing the positioning of the working fluid reservoir and the plurality of microfluidic devices or chips positioned on the manifold. Experimental A. Plug Sampling Concept Experiment In an experiment, the ice core sampling concept was tested, which is illustrated in FIG. 23, where a separation media (gas or liquid) is used to create discrete samples or "plugs." The plugs, stored in chronological order, stay separate due to capillary pressure. The tubing containing the plugs may be stored at a lower temperature during the experiment in order to maintain sample fidelity and then frozen after the experiment for later analysis. The other components of the assembly are not shown.

Figure 24:
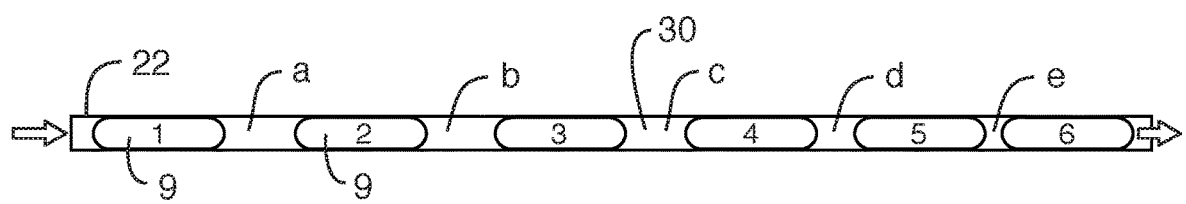
FIG. 24 is a schematic showing one embodiment of a sampling conduit (first round) test setup where dye is used to distinguish samples from the separation media (gas or liquid).

FIG. 24 is a schematic showing one embodiment of a sampling conduit (first round) test setup where dye is used to distinguish samples from the separation media (gas or liquid). It was desired to know if neighboring plugs would bleed into one another. The samples were manually pulled into the 1 mm internal diameter capillary tubing using a 1 mL syringe with 10μ graduations. Plugs of cell effluent, cell media that had been in contact with the cells, (9) were alternately administered with Lucifer Yellow fluorescent dye and no dye, frozen for 24-48 hours before being thawed. By alternating plug media and measuring fluorescence of samples the degree of discretization could be analyzed. The cell media used in this experiment, PBS, does not fluoresce. Sample plugs were manually pushed out into individual wells on a 96 well plate using identical 1 mL syringes. A plate reader was then used to measure fluorescence. If there was bleed over, the fluorescent signal in the plugs that did not have dye was measured. A high raw intensity value as measured on a plate reader means higher fluorescent signal. Plug volumes were decreased from 100 μL (a) to 20 μL (e).

Figure 25:
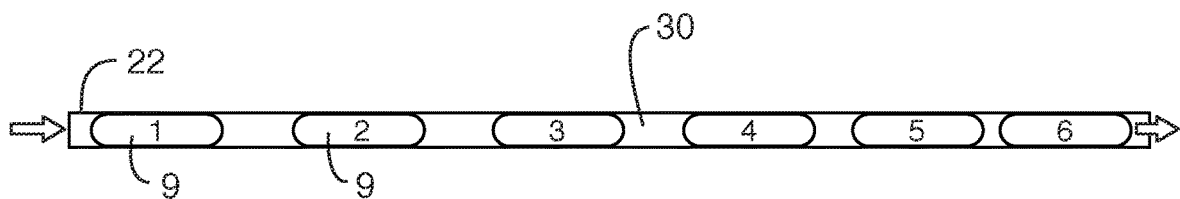
FIG. 25 is a schematic showing first round results using a sampling conduit where dye was used to distinguish samples. The results showed successful discretization of fluorescent and non-fluorescent samples in 0.040 ID PEEK capillary tubing.

FIG. 25 is a schematic showing first round results from the test setup in FIG. 24 using a sampling conduit where dye was used to distinguish samples. The results showed successful discretization of fluorescent and non-fluorescent samples in 0.040 ID PEEK capillary tubing. Samples containing fluorescence had fluorescence signals between 253-399, while samples not containing fluorescence had fluorescence signals between 0-35. Control wells containing 100% Lucifer Yellow and 40% Lucifer Yellow had fluorescence measurements of 371 and 143 respectively. The results indicate that there was not a high amount of cross over between plugs.

Figure 26:
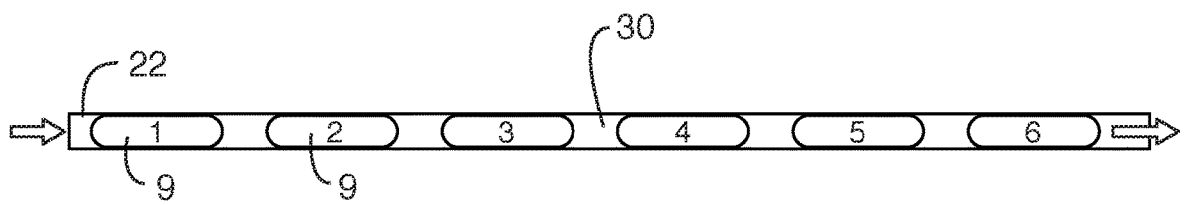
FIG. 26 is a schematic showing one embodiment of a sampling conduit (second round) test setup where dye is used to distinguish samples from the separation media (gas or liquid).

FIG. 26 is a schematic showing one embodiment of a sampling conduit (second round) test setup where dye is used to distinguish samples from the separation media (gas or liquid). Instead of manually pulling the plugs into the tubing using a syringe the plugs were automatically pulled into the capillary tubing using a 5 mL syringe on a syringe pump. The capillary tubes with discretized sample plugs and air plugs were placed in a −80° C. freezer for about 4 days before fluorescence analysis. The tubing used in the experiment was 1/32" internal diameter, 1/16" outer diameter FEP capillary tubing. Two different tubes were used during the experiment. Sample plugs were automatically pushed into individual wells on a 96 well plate using identical 5 mL syringes on a syringe pump. A plate reader was used to measure fluorescence. The plate reader data was normalized to measured volume of sample in the plate.

Figure 27:
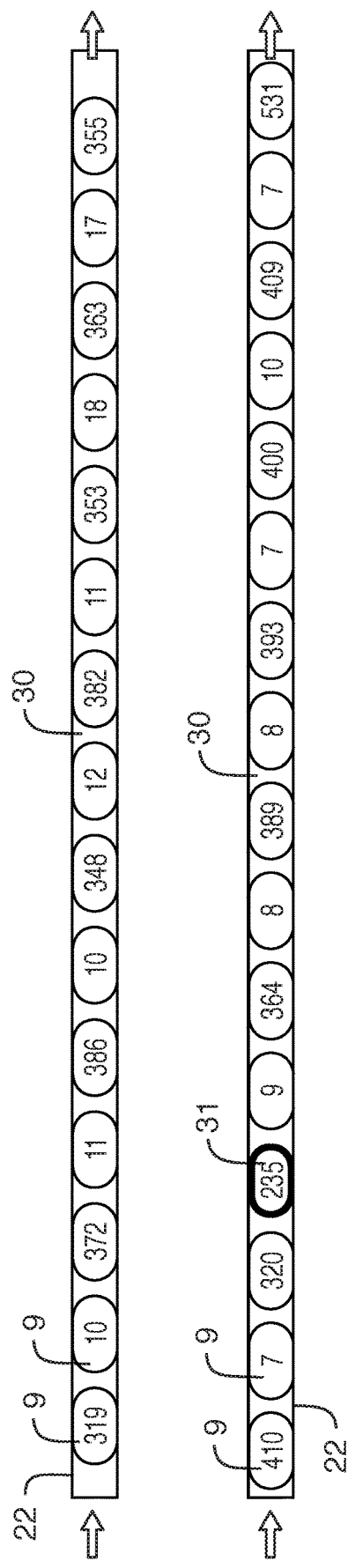
FIG. 27 is a schematic showing second round results using a sampling conduit where dye was used to distinguish samples. The results showed successful discretization of fluorescent and non-fluorescent samples in 0.031 ID FEP capillary tubing.

FIG. 27 is a schematic showing second round results using a sampling conduit where dye was used to distinguish samples. The results showed successful discretization of fluorescent and non-fluorescent samples in 0.031 ID FEP capillary tubing. In the first sample run samples containing fluorescence had fluorescence signals between 319-382, while samples not containing fluorescence had fluorescence signals between 10-18. In the second sample run samples containing fluorescence had fluorescence signals between 310-531, while samples not containing fluorescence had fluorescence signals between 7-10. In the second sample run one plug (31) leading to a low error percentage of the system. Five control wells contained only Lucifer Yellow and five control wells contained only the cell culture media DPBS. The Lucifer Yellow control wells had fluorescence values between 378-443. The DPBS had fluorescence values between 4-5.

B. Thermal Environment Modeling

In a second experiment a mathematical representation of the thermal environment across the entire system was built to determine if two highly different temperatures, namely the 4° C. *media* temperature and the 37° C. Organs-on-Chip temperature, could coexist in such a small system. The mathematical calculations are summarized in FIG. 32. The model showed that the biggest increase in efficiency could be achieved by better insulating the container housing the flexible reservoirs and the working fluid. Adding foam insulation to the container improved efficiency modestly, but the mathematical model showed that a double-walled vacuum insulation would improve efficiency significantly enough in order to be able to achieve both temperature environments in the same small system. Heat gains for the rigid reservoir with quarter inch thick foam insulation was calculated to be 2.2 Watts. The heat gains decreased to 0.4 Watts when the foam insulation was replaced by double-walled vacuum insulation. There was a 50-fold improvement in efficiency.

Various double-walled vacuum containers that fit the size constraints were considered, however the most successful option was a double-walled vacuum flask. A custom cap was designed that would allow for the tubing routing in and out of the thermos. Fluid tubing was routed through a commercial off-the-shelf waterproof strain-relief fitting.

We claim:

1. A method of moving liquid, comprising:
   a) providing an assembly, comprising one or more liquid reservoirs contained within a container, said container in fluidic communication with e a first working fluid reservoir and a second working fluid reservoir, said first working fluid reservoir comprising a first working fluid, said second working fluid reservoir comprising a second working fluid, said container further comprising a portion of said second working fluid, said one or more liquid reservoirs in fluidic communication with one or more fluidic devices, and comprising liquid, wherein there is no mixing of said working fluid with said liquid; and
   b) introducing said first working fluid from said first working fluid reservoir into said container under conditions that said pressure is imparted on said second working fluid such that liquid in said one or more reservoirs is displaced and flows into said one or more fluidic devices, thereby moving said liquid.

2. The method of claim 1, wherein said container is rigid or flexible.

3. The method of claim 1, wherein said container is collapsible.

4. The assembly of claim 1, wherein said container is insulated.

5. The method of claim 1, wherein said container is sealed such that said working fluid can only enter or exit the container through conduits.

6. The method of claim 1, wherein said one or more reservoirs are flexible.

7. The method of claim 1, wherein said one or more reservoirs comprise at least one deformable portion.

8. The method of claim 1, wherein said first working fluid comprises gas.

9. The method of claim 1, further comprising cooling said first or second working fluid, or both.

10. The method of claim 9, wherein said working fluid is cooled with a cooling conduit comprising a cooling fluid, wherein said cooling fluid does not mix with said working fluid or with said liquid.

11. The method of claim 10, wherein said cooling conduit comprises stainless steel tubing.

12. The method of claim 1, wherein said liquid is heated after it is displaced but prior to it flowing into said one or more fluidic devices.

13. A method of introducing reagent into microfluidic devices comprising:
   a) providing an assembly, comprising one or more flexible cell culture media reservoirs and one or more flexible reagent reservoirs contained within a container, said container in fluidic communication with a pump and a working fluid reservoir and comprising a working fluid, said flexible cell culture reservoirs in fluidic communication with one or more microfluidic devices comprising cells on a surface and comprising cell culture media, said one or more flexible reagent reservoirs in fluidic communication with one or more microfluidic devices and comprising reagent, wherein there is no contact or mixing of said working fluid with said cell culture media;

b) pumping said working fluid into said container with said pump under conditions that the culture media in the flexible reservoirs is displaced and flows into said one or more microfluidic devices, thereby perfusing said cells, wherein reagent in said flexible reagent reservoirs is not displaced; and c) pumping said working fluid into said container with said pump under conditions that the reagent in at least one flexible reagent reservoir is displaced and flows into said one or more microfluidic devices, thereby introducing reagent into said one or more microfluidic devices.

14. The method of claim 13, wherein said assembly further comprises valves to control the flow of said culture media out of said flexible cell culture media reservoirs and valves to control the flow of reagent out of said flexible reagent reservoirs.

15. The method of claim 14, wherein a valve prevents reagent in said flexible reagent reservoir from being displaced in step 2).

16. The method of claim 14, wherein a valve permits reagent in at least one of said flexible reagent reservoir to be displaced in step 3).

17. The method of claim 13, wherein said one or more microfluidic devices are outside said container.

18. The method of claim 13, wherein said one or more microfluidic devices are housed in a manifold.

19. The method of claim 13, wherein said surface is a microfluidic channel or portion thereof.

20. The method of claim 13, wherein said surface is a membrane.

21. The method of claim 13, wherein said container is rigid or flexible.

22. The method of claim 13, wherein said container is collapsible.

23. The method of claim 13, wherein said container is insulated.

24. The method of claim 13, wherein said container is sealed such that said working fluid can only enter or exit the container through conduits.

25. The method of claim 13, further comprising cooling said working fluid.

26. The method of claim 25, wherein said working fluid is cooled with a cooling conduit comprising a cooling fluid, wherein said cooling fluid does not mix with said working fluid or with said liquid.

27. The method of claim 26, wherein said cooling conduit comprises stainless steel tubing.

28. The method of claim 13, wherein said liquid is heated after it is displaced but prior to it flowing into said one or more fluidic devices.

29. A method of collecting samples from microfluidic devices, comprising:

a) providing an assembly, comprising one or more reservoirs contained within a container, said container in fluidic communication with a pump and a working fluid reservoir and comprising a working fluid, said reservoirs in fluidic communication with one or more microfluidic devices and comprising cell culture media, said one or more microfluidic devices in fluidic communication with a sampling conduit and comprising cells on a surface, wherein there is no mixing of said working fluid with said cell culture media;

b) pumping said working fluid into said container with said pump under conditions that the culture media in the reservoirs is displaced and flows into said one or more microfluidic devices, thereby causing fluid to exit said one or more microfluidic devices and enter said sampling conduit; and c) collecting samples from said sampling conduit.

30. The method of claim 29, further comprising introducing gas into said sampling conduit to separate said fluid into discrete volumes.

31. The method of claim 29, wherein said container is rigid or flexible.

32. The method of claim 29, wherein said container is collapsible.

33. The method of claim 29, wherein said container is insulated.

34. The method of claim 29, wherein said container is sealed such that said working fluid can only enter or exit the container through conduits.

35. The method of claim 29, further comprising cooling said working fluid.

36. The method of claim 35, wherein said working fluid is cooled with a cooling conduit comprising a cooling fluid, wherein said cooling fluid does not mix with said working fluid or with said liquid.

37. The method of claim 36, wherein said cooling conduit comprises stainless steel tubing.

38. The method of claim 29, wherein said liquid is heated after it is displaced but prior to it flowing into said one or more fluidic devices.

39. A method of recirculating culture media through microfluidic devices without reversing the direction of fluid flow, comprising:

a) providing an assembly, comprising one or more reservoirs contained within a container, said container in fluidic communication with a pump and a working fluid reservoir and comprising a working fluid, said reservoirs in fluidic communication with one or more microfluidic devices and comprising cell culture media, said one or more microfluidic devices comprising cells on a surface and inlet and outlet ports, said inlet and outlet ports in fluidic communication with a recirculation pathway, wherein there is no mixing of said working fluid with said cell culture media; and b) pumping said working fluid into said container with said pump under conditions that the culture media in the reservoirs is displaced and flows into said one or more microfluidic devices in a direction, thereby causing fluid to exit said outlet port of said one or more microfluidic devices and enter said recirculation pathway, moving in the direction of said inlet port of said one or more microfluidic devices.

40. The method of claim 39, wherein said pumping causes said fluid moving in the direction of said inlet port to reach said inlet port, thereby recirculating said culture media without reversing the direction of fluid flow.

41. The method of claim 39, wherein said one or more microfluidic devices are housed on a manifold.

42. The method of claim 41, wherein said recirculation pathway is positioned on said manifold.

43. The method of claim 39, wherein said container is rigid or flexible.

44. The method of claim 39, wherein said container is collapsible.

45. The method of claim 39, wherein said container is insulated.

46. The method of claim 39, wherein said container is sealed such that said working fluid can only enter or exit the container through conduits.

47. The method of claim 39, further comprising cooling said working fluid.

48. The method of claim 47, wherein said working fluid is cooled with a cooling conduit comprising a cooling fluid, wherein said cooling fluid does not mix with said working fluid or with said liquid.

49. The method of claim 48, wherein said cooling conduit comprises stainless steel tubing.

50. The method of claim 39, wherein said liquid is heated after it is displaced but prior to it flowing into said one or more fluidic devices.

* * * * *